(12) United States Patent
Ip et al.

(10) Patent No.: US 11,690,810 B2
(45) Date of Patent: Jul. 4, 2023

(54) COMBINATION TREATMENT OF BACTERIAL INFECTION

(71) Applicant: The Chinese University of Hong Kong, Hong Kong (CN)

(72) Inventors: Margaret Ip, Hong Kong (CN); Kwok Pui Fung, Hong Kong (CN); Ping Chung Leung, Hong Kong (CN); Clara Bik San Lau, Hong Kong (CN); Quan Bin Han, Hong Kong (CN); Chung Lap Chan, Hong Kong (CN); Chit Tsui, Hong Kong (CN); Quande Wang, Xiangtan (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/684,073

(22) Filed: Nov. 14, 2019

(65) Prior Publication Data

US 2020/0155641 A1 May 21, 2020

Related U.S. Application Data

(60) Provisional application No. 62/767,122, filed on Nov. 14, 2018.

(51) Int. Cl.

| A61K 31/12 | (2006.01) |
| A61K 38/14 | (2006.01) |
| A61P 31/04 | (2006.01) |
| A61K 31/353 | (2006.01) |
| A61K 31/575 | (2006.01) |
| A61K 31/7036 | (2006.01) |
| A61K 31/192 | (2006.01) |
| A61K 31/352 | (2006.01) |
| A61K 31/43 | (2006.01) |
| A61K 31/58 | (2006.01) |
| A61K 45/06 | (2006.01) |

(52) U.S. Cl.
CPC ............ *A61K 31/12* (2013.01); *A61K 31/192* (2013.01); *A61K 31/352* (2013.01); *A61K 31/353* (2013.01); *A61K 31/43* (2013.01); *A61K 31/575* (2013.01); *A61K 31/58* (2013.01); *A61K 31/7036* (2013.01); *A61K 38/14* (2013.01); *A61P 31/04* (2018.01); *A61K 45/06* (2013.01)

(58) Field of Classification Search
None
See application file for complete search history.

(56) References Cited

U.S. PATENT DOCUMENTS

| 5,358,713 A * | 10/1994 | Shimamura | A23F 3/16 424/729 |
| 2006/0235076 A1* | 10/2006 | Higuchi | A61K 36/48 514/543 |
| 2018/0263917 A1* | 9/2018 | Rubin | A61K 31/4439 |

OTHER PUBLICATIONS

Chan et al. ("Quick identification of kuraridin, a noncytotoxic anti-MRSA (methicillin-resistant *Staphylococcus aures*) agent from *Sophora flavescens* using high-speed counter-current chromatography", Journal of Chromatography B, vol. 880 (2012), p. 157-162) . (Year: 2012).*
Chan, et al., "Quick identification of kuraridin, a noncytotoxic anti-MRSA (methicillin-resistant *Staphylococcus aureus*) agent from *Sophora flavescens* using high-speed counter-current chromatography", Journal of Chromatography B, vol. 880, pp. 157-162 (2012).

* cited by examiner

*Primary Examiner* — Sin J Lee
(74) *Attorney, Agent, or Firm* — Kilpatrick Townsend & Stockton LLP

(57) ABSTRACT

The present invention resides in the discovery that combined use of kuraridin (or any one of its analogs) and epicatechin gallate (ECG) can provide heightened level of antimicrobial activity, especially for the suppression of bacteria of the *Staphylococcus aureus* and Staphylococcal species. Compositions, kits, and methods for the combination use are disclosed.

20 Claims, 72 Drawing Sheets

Combined effects of epicatechin gallate (ECG) (8-32 μg/ml) and kuraridin (16 μg/ml) on IL-6 production from stimulated PBMC Combined effects of epicatechin gallate (ECG) (8-32 µg/ml) and kuraridin (16 µg/ml) on IFNγ production from stimulated macrophage Combined effects of epicatechin gallate (ECG) (8-32 µg/ml) and kuraridin (16 µg/ml) on IL-10 production from macrophage

COMBINATION TREATMENT OF BACTERIAL INFECTION

RELATED APPLICATION

This application claims priority to U.S. Provisional Patent Application No. 62/767,122, filed Nov. 14, 2018, the contents of which are hereby incorporated in the entirety for all purposes.

BACKGROUND OF THE INVENTION

Resistance to antimicrobials in microorganisms is a very significant and growing problem. At the present time, there are very limited options in the treatment of antibiotic-resistant microorganisms such as methicillin-resistant *Staphylococcus aureus* (MRSA). There exists an urgent need for developing new and effective methods for treating diseases and conditions caused or exacerbated by these antibiotic-resistant microorganisms. Based on the previous studies published by various research groups, six promising candidates from Traditional Chinese Medicines (TCM), namely kuraridin from Sophorae Flavescentis Radix (苦参), baicalein from Scutellariae Radix (黄芩), berberine from Coptidis Rhizoma (黄連), tanshinone from Salviae Miltiorrhizae Radix et Rhizoma (丹参), gallic acid from Moutan Cortex (丹皮) and epicatechin gallate from green tea (綠茶) were selected for further testing in this study in an effort to develop an efficacious non-toxic herbal and antibiotics combination for MRSA treatment with antibacterial and anti-inflammatory activities. The discovery disclosed herein fulfills the need for new and effective means for treating bacterial infections, especially antibiotic-resistant bacterial infections, and other related needs.

BRIEF SUMMARY OF THE INVENTION

The invention relates to novel methods and compositions useful for suppressing the growth or proliferation of bacteria, especially antibiotic-resistant bacteria, such as methicillin-resistant *Staphylococcus aureus* (MRSA). Thus, in the first aspect, the present invention provides a novel method for suppressing bacteria growth, the method comprising contacting the bacteria with two or more anti-bacterial agents selected from the group consisting of baicalein, berberine, gallic acid, kuraridin (or any one of its analogs set forth in Table 7, e.g., analog WQD175 or WQD165), epicatechin gallate (ECG), and tanshinone, each in an effective amount.

In some embodiments, the two or more anti-bacterial agents comprise kuraridin (or any one of its analogs set forth in Table 7, e.g., analog WQD175 or WQD165) and ECG. In some embodiments, the method further comprises contacting the bacteria with an effective amount of an antibiotic. The antibiotic can be a bactericidal antibiotic or a bacteriostatic antibiotic. For example, the antibiotic is amoxicillin, fusidic acid, gentamycin, or vancomycin. In some embodiments, when the method involves combination use of ECG and kuraridin (or any one of its analogs set forth in Table 7, e.g., analog WQD175 or WQD165), optionally further with vancomycin. For example, in one combination use ECG concentration is at least about 0.25-8 µg/ml and kuraridin (or any one of its analogs set forth in Table 7, e.g., analog WQD175 or WQD165) concentration is at least about 1-4 µg/ml. In another combination use, ECG concentration is about 2 µg/ml, kuraridin (or any one of its analogs set forth in Table 7, e.g., analog WQD175 or WQD165) concentration is at least about 2 µg/ml, and vancomycin concentration is about 0.5 µg/ml.

In some embodiments, the bacteria being suppressed are antibiotic-resistant, e.g., MRSA. In some embodiments, the bacteria are within a living organism, such as a human being suffering from a bacterial infection. In the context of human use, the claimed method in some cases includes the step of administering to a human patient kuraridin (or any one of its analogs set forth in Table 7, e.g., analog WQD175 or WQD165), ECG, and vancomycin, each at a concentration of about 30-120 mg/kg human bodyweight. For example, a human patient may receive for his bacterial infection kuraridin (or any one of its analogs set forth in Table 7, e.g., analog WQD175 or WQD165) at about 30 mg/kg, ECG at about 60 mg/kg, and vancomycin at about 120 mg/kg, with this combination treatment schedule repeated once every 12 hours for at least two days.

Related to the first aspect, the present invention provides use of a combination of at least two (optionally more) anti-bacterial agents described above and herein to manufacture a medicament for treating bacterial infections, especially infections caused by antibiotic-resistant bacteria. An antibiotic may be further included in the medicament, for example, a combination of ECG, kuraridin (or any one of its analogs set forth in Table 7, e.g., analog WQD175 or WQD165), and vancomycin can be used to produce effective therapeutic modality for treating infections caused by bacteria, especially antibiotic-resistant bacteria.

In a second aspect, the present invention provides a composition for suppressing bacterial growth, which comprises (1) two or more anti-bacterial agents selected from the group consisting of baicalein, berberine, gallic acid, kuraridin (or any one of its analogs set forth in Table 7, e.g., analog WQD175 or WQD165), epicatechin gallate (ECG), and tanshinone, each in an effective amount; and (2) a physiologically acceptable excipient. In some embodiments, the composition includes kuraridin and ECG as the two or more anti-bacterial agents. Optionally, the composition further comprises an effective amount of an antibiotic, which can be either a bactericidal antibiotic or a bacteriostatic antibiotic. In some embodiments, the antibiotic included in the composition is amoxicillin, fusidic acid, gentamycin, or vancomycin. For example, the composition in some cases may include kuraridin and ECG as the anti-bacterial agents and vancomycin as the antibiotic.

In a third aspect, the present invention provides a kit for use in suppressing bacterial growth. The kit comprises (1) a first composition comprising an effective amount of a first anti-bacterial agent; and (2) a second composition comprising an effective amount of a second anti-bacterial agent, each of the first and second anti-bacterial agents is selected from the group consisting of baicalein, berberine, gallic acid, kuraridin (or any one of its analogs set forth in Table 7, e.g., analog WQD175 or WQD165), epicatechin gallate (ECG), and tanshinone. In some embodiments, the first anti-bacterial agent is ECG and the second anti-bacterial agent is kuraridin (or any one of its analogs set forth in Table 7, e.g., analog WQD175 or WQD165). In some embodiments, the kit further includes an antibiotic in an effective amount. The antibiotic is a bactericidal antibiotic or a bacteriostatic antibiotic, for example, it can be amoxicillin, fusidic acid, gentamycin, or vancomycin. In some embodiments, the first and second anti-bacterial agents are ECG and kuraridin (or any one of its analogs set forth in Table 7, e.g., analog WQD175 or WQD165), and the antibiotic is vancomycin. In some embodiments, the first composition is an aqueous solution (e.g., a saline solution) comprising ECG and vancomycin, and the second composition is an aqueous solution comprising kuraridin (or any one of its analogs set forth in Table 7, e.g., analog WQD175 or WQD165) and an organic solvent (e.g., a solution of saline and ethanol).

BRIEF DESCRIPTION OF THE DRAWINGS

(FIG. 7A) The bacteria counts in Log CFU recovered from the left lungs and the survival rates of the mice treated with (FIG. 7B) vancomycin, (FIG. 7C) ECG and (FIG. 7D) kuraridin. Significant results by comparing the drug treatment groups with the drug free control are indicated ($*p<0.05$; $p<0.01$; $*p<0.001$).

(FIG. 8A) The bacteria counts in Log CFU recovered from the left lungs; (FIG. 8B) the survival rates of each treatment group and (FIG. 8C) the pneumonia scores of the right lung histology (n=10). Significant results by comparing the drug treatment groups with the drug free control are indicated ($*p<0.05$; $p<0.01$; $*p<0.001$).

(FIG. 13A) The bacteria counts in Log CFU recovered from the left lungs; (FIG. 13B) the survival rates of each treatment group and (FIG. 13C) the pneumonia scores of the right lung histology.

FIGS. 17A, 17C, 17E and 17G show the adherence of MRSA strain JE-2 and its isogenic mutant ΔSrtA to HaCat keratinocytes at varying concentrations of baicalein, berberine, ECG and kuraridin, while FIGS. 17B, 17D, 17F and 17H show the internalization of strain JE-2 and ΔSrtA to HaCat keratinocytes with the corresponding compounds respectively. Internalization of JE-2 to Hacat cells was taken as 100%. The error bars represent the standard deviation of the mean values. Significance was determined by One-way ANOVA (*$p<0.05$, **$p<0.01$). The adherence of the WT strain and ΔSrtA strain were observed to be 75.9±7.9% and 35.3+18.4% respectively. An average of 3.5 fold decrease in the adherence of the WT strain to HaCaT cells was observed upon treatment with varying concentrations of baicalein (ranged 17.7±7.9 to 22±1.4 μg/ml but not in a dose dependent fashion) and lower than that of the ΔSrtA. Treatment of the bacteria with 64 μg/ml of baicalein exhibited 5-fold reduction in internalization as compared to the WT strain and 1.9 fold lower as compared to the mutant ΔSrtA (FIG. 17B). Treatment with 4 μg/ml revealed a 2.7-fold decrease in the internalization as compared to the WT strain. The percentage of adherence of the bacteria to HaCaT cells was observed to be 73.0±4.1, 75.4±11.0, 76.4±7.0, 58.8±8.5 and 52±6.5 at the concentration 4, 8, 16, 32 or 64 μg/ml of ECG respectively (FIG. 17E). A 1.4 fold decrease in the adherence of the WT strain to HaCaT cells was observed upon treatment with 64 μg/ml of ECG. The percentage of internalized bacteria by HaCaT cells was observed to be 62.2±2.7, 62.8±10.5, 53.7±6.3, 42.2±8.9 and 34.7±4.5 when treated with ECG at the concentration 4, 8, 16, 32 or 64 μg/ml respectively (FIG. 17F). Adherence of WT strain was abolished at 2 μg/ml kuraridin, and a dose dependent reduction also observed at lower concentrations of kuraridin ($p<0.01$) (FIG. 17G). No bacterial cells were recovered in the CFU count even though the concentration was 0.25×MIC. The percentage of adherence of the bacteria when treated with kuraridin was observed to be 28.4±3.2, 17.8±11.1, 7.6±3.7 at the concentration 0.25, 0.5 and 1 μg/ml respectively (3 g). The percentage of internalized bacteria by HaCaT cells was observed to be 23.8±4.6 and, 15.8±2.0 at kuraridin 0.25 and 0.5 μg/ml respectively (FIG. 17H).

FIG. 22B. Cellular toxicity (XTT assay) of kuraridin and its analogues on human peripheral blood mononuclear cells (PBMCs). The results were expressed as % growth of drug free control±standard error of mean (n=3). All compounds were non-toxic at concentrations up to 64 µg/ml, except for WQD165.

DEFINITIONS

Figure 1A:
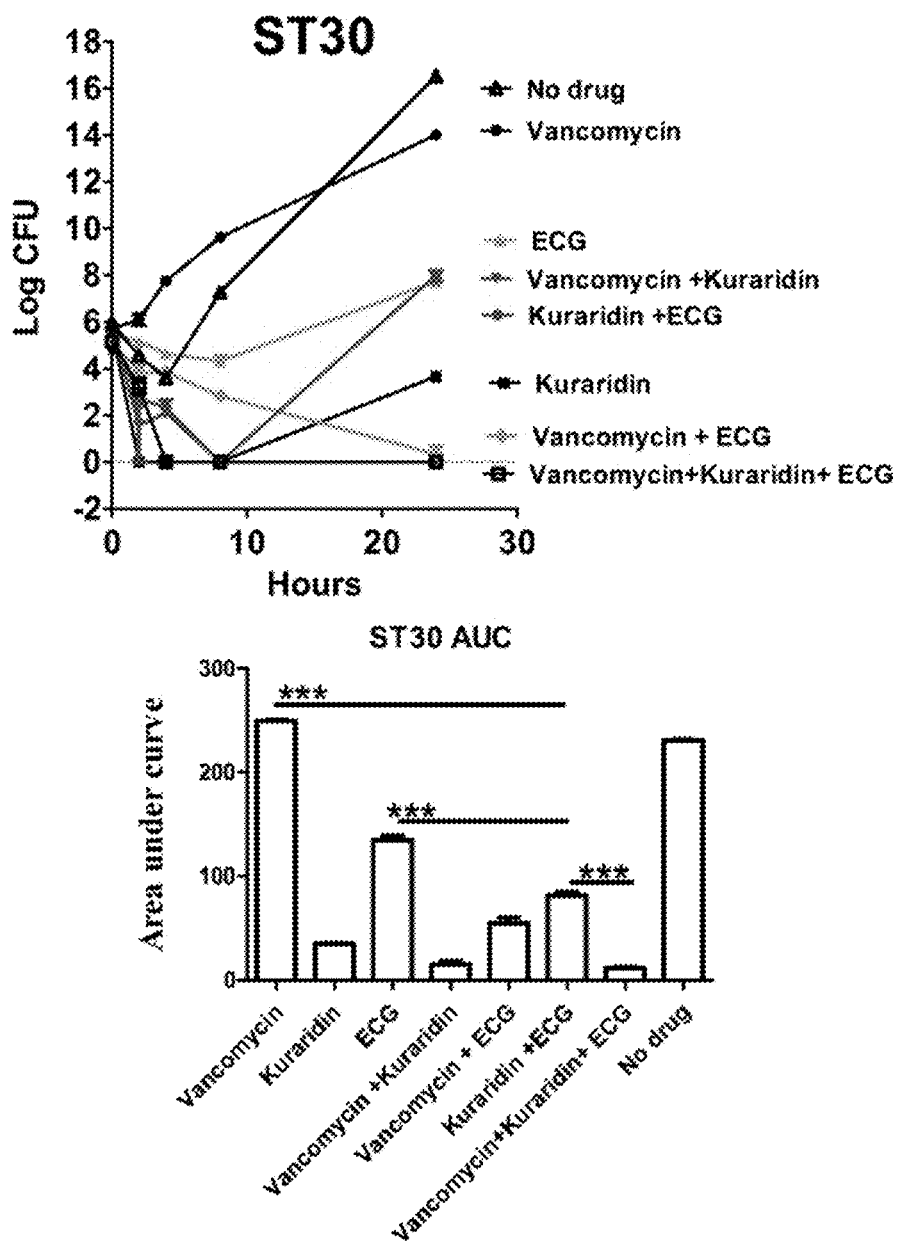
FIGS. 1A-1C In vitro time-kill curves and the area under the curve (AUC) of epicatechin gallate (ECG) (2 µg/ml), kuraridin (2 µg/ml) and vancomycin (0.5 µg/ml) alone and in combination against (FIG. 1A) ST30, (FIG. 1B) ST239 and (FIG. 1C) ATCC25923. Results are expressed as log CFU/ml and are given as mean±standard error of mean (n=3).

The term "anti-bacterial agent" refers to any substance that can exert a detectable negative effect on the growth or proliferation of any one or more bacterial species. While an "anti-bacterial agent" by itself may not be sufficient to kill bacteria or arrest bacterial proliferation at a significant level, two or more such agents when used together may combinedly achieve a synergy in bacterial kill and/or growth arrest. In particular, the combined use of two or more anti-bacterial agents can enhance the effect of a conventional antibiotic as manifested in (1) reducing the minimal effective amount of the conventional antibiotic to achieve bacterial kill and/or growth arrest; and/or (2) potentiating the conventional antibiotic in overcoming resistance to antibiotic acquired by bacteria.

"Baicalein" or 5,6,7-trihydroxyflavone is a flavone, a type of flavonoid, originally isolated from the roots of *Scutellaria baicalensis* and *Scutellaria lateriflora*. It is also reported in *Oroxylum indicum* (*Indian trumpetflower*) and Thyme. It is the aglycone of baicalin. Baicalein is one of the active ingredients of Sho-Saiko-To, a Chinese herbal supplement believed to enhance liver health. Its chemical structure is shown below:

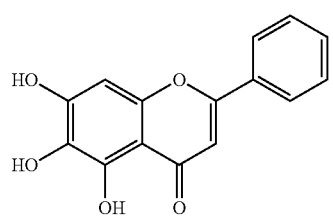 [SMILES: O=c1cc(-c2ccccc2)oc2cc(O)c(O)c(O)c12]

Berberine is a quaternary ammonium salt from the protoberberine group of benzylisoquinoline alkaloids, usually found in the roots, rhizomes, stems, and bark of plants such as *Berberis* (e.g., *Berberis vulgaris*—barberry, *Berberis aristata*—tree turmeric, *Mahonia aquifolium*—Oregongrape, *Hydrastis canadensis*—goldenseal, *Xanthorhiza simplicissima*—yellowroot, *Phellodendron amurense*—Amur cork tree, *Coptis chinensis*—Chinese goldthread, *Tinospora cordifolia, Argemone mexicana*—prickly poppy, and *Eschscholzia californica*—Californian poppy). Its chemical structure is shown below:

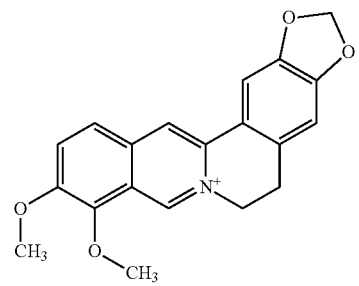 [SMILES: COc1ccc2cc3[n+](cc2c1OC)CCc1cc2c(cc1-3)OCO2]

Gallic acid (also known as 3,4,5-trihydroxybenzoic acid) is a trihydroxybenzoic acid, a type of phenolic acid, found in various plants such as gallnuts, sumac, witch hazel, tea leaves, and oak bark. The chemical structure of gallic acid is shown below:

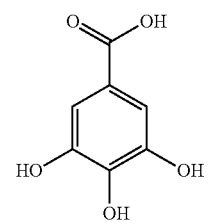

"Kuraridin" has the chemical structure shown below in Formula I.

Formula I

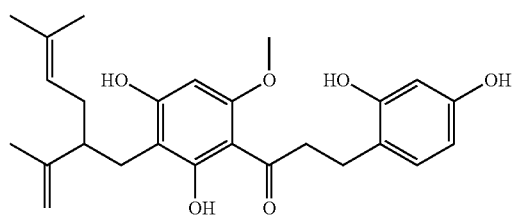

As used herein the term "kuraridin" also encompasses, in addition to the compound shown in Formula I, various derivatives thereof with similar or enhanced anti-bacterial effect. Exemplary kuraridin analogs are set forth in Table 7. For instance, "kuraridin" encompasses the chemical compounds within the genus shown in Formular II and described below:

(formula II)

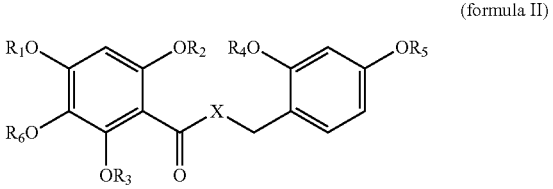

Kuraridin Genus wherein

X is carbon, nitrogen, oxygen, or sulfur;

$R_1$-$R_5$ are independently selected from hydrogen, alkyl, or halogen, with the proviso that at least one of $R_1$-$R_5$ is not hydrogen; and $R_6$ is C3-C20 alkyl comprising at least one double bond.

As another example, "kuraridin" also encompasses derivatives belonging to the sub-genus shown in Formula III and described below:

Formula III

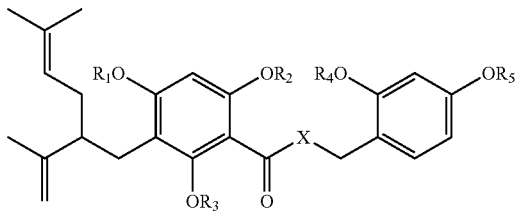

wherein

X is carbon, nitrogen, oxygen, or sulfur; and $R_1$-$R_5$ are independently selected from hydrogen, alkyl, or halogen, with the proviso that at least one of $R_1$-$R_5$ is not hydrogen.

As used herein, alkyl refers to any straight chain or branched, substituted or unsubstituted, saturated or unsaturated, alkyl ester, or alkyl ether alkyl moiety. The alkyl may be a $C_2$-$C_{36}$ alkyl, a $C_2$-$C_{12}$ alkyl, a $C_{12}$-$C_{36}$ alkyl, a $C_2$-$C_{12}$ alkyl, a $C_2$-$C_{12}$ alkyl, a $C_2$-$C_{12}$ alkyl.

As used herein, "epicatechin gallate (ECG)" refers to a flavan-3-ol, a type of flavonoid present in green tea as well as in buckwheat and in grape. Its chemical structure depicted below, ECG has also been reported to act as a non-selective antagonist of the opioid receptors, albeit with somewhat low affinity.

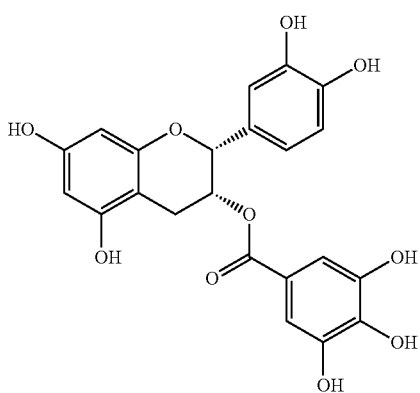 [SMILES: O=C(O[C@@H]1Cc2c(O)cc(O)cc2O[C@@H]1c1ccc(O)c(O)c1)c1cc(O)c(O)c(O)c1]

Tanshinones are a class of naturally occurring chemical compounds that can be isolated from *Salvia miltiorrhiza*, including exemplary members such as dihydrotanshinone, tanshinone I, or tanshinone IIA. Dihydrotanshinone I has been reported to have cytotoxicity to a variety of tumor cells. Tanshinone I is an anti-inflammatory and modulates or prevents breast cancer metastasis by regulating adhesion molecules. Tanshinone IIA is anti-inflammatory, an antioxidant, and cytotoxic against a variety of cell lines. The chemical structure of tanshinone I is depicted below:

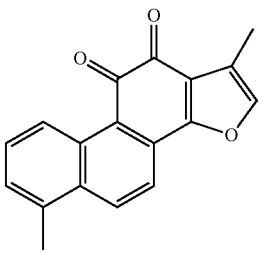 [SMILES: Cc1coc2c1C(=O)C(=O)c1c-2ccc2c(C)cccc12]

The term "inhibiting" or "inhibition," as used herein, refers to any detectable negative effect on a target biological process, such as RNA/protein expression of a target gene, the biological activity of a target protein, cellular signal transduction, cell proliferation, and the like. Typically, an inhibition is reflected in a decrease of at least 10%, 20%, 30%, 40%, 50%, 60%, 70%, 80%, 90% or greater in the target process (e.g., growth or proliferation of bacterial cells of certain species, including those that have acquired antibiotic-resistance), or any one of the downstream parameters mentioned above, when compared to a control. "Inhibition" further includes a 100% reduction, i.e., a complete elimination, prevention, or abolition of a target biological process or signal. The other relative terms such as "suppressing," "suppression," "reducing," and "reduction" are used in a similar fashion in this disclosure to refer to decreases to different levels (e.g., at least 10%, 20%, 30%, 40%, 50%, 60%, 70%, 80%, 90% or greater decrease compared to a control level) up to complete elimination of a target biological process or signal. On the other hand, terms such as "activate," "activating," "activation," "increase," "increasing," "promote," "promoting," "enhance," "enhancing," or "enhancement" are used in this disclosure to encompass positive changes at different levels (e.g., at least 10%, 20%, 30%, 40%, 50%, 60%, 70%, 80%, 90%, 100%, 200%, or greater such as 3, 5, 8, 10, 20-fold increase compared to a control level, for example, the control level of bacterial cells growth or proliferation of one or more of the species including those having acquired antibiotic-resistance) in a target process or signal.

The term "antibiotic" refers to any substance that is capable of inhibiting, suppressing, or preventing the growth or proliferation of one or more bacterial species. An antibiotic is a type of antimicrobial substance active against bacteria and is the most important type of antibacterial agent for fighting bacterial infections. Antibiotic medications are widely used in the treatment and prevention of such infections. They may either kill or inhibit the growth of bacteria. Antibiotics are commonly classified based on their mechanism of action, chemical structure, or spectrum of activity. Typically, antibiotics exert their inhibitory effects by targeting bacterial functions or growth processes. For instance, those that target the bacterial cell wall (penicillins and cephalosporins) or the cell membrane (polymyxins), or interfere with essential bacterial enzymes (rifamycins, lipiarmycins, quinolones, and sulfonamides) have bactericidal activities, whereas protein synthesis inhibitors (macrolides, lincosamides, and tetracyclines) are usually bacteriostatic (with the exception of bactericidal aminoglycosides). Insofar as their target specificity is concerned, "narrow-spectrum" antibiotics target specific types of bacteria, such as gram-negative or gram-positive, in contrast to "broad-spectrum" antibiotics, which affect a wide range (if not all) of bacteria.

The term "effective amount," as used herein, refers to an amount of a substance that produces a desired effect (e.g., an inhibitory or suppressive effect on the growth or proliferation of one or more bacterial species, especially bacterial species with drug-resistance) for which the substance (e.g., an antibiotic) is used or administered. The effects include the prevention, inhibition, or delaying of any pertinent biological process during bacterial growth or proliferation to any detectable extent. The exact amount will depend on the nature of the substance (the anti-bacterial agent), the manner of use/administration, including other active agent(s) co-administered at approximately the same time, and the purpose of the application, and will be ascertainable by one skilled in the art using known techniques as well as those described herein.

As used herein, the term "about" denotes a range of value that is +/−10% of a specified value. For instance, "about 10" denotes the value range of 10+/−10×10%, i.e., 9 to 11.

DETAILED DESCRIPTION OF THE INVENTION

I. Introduction

By using a panel of MRSA strains, the present inventors have tested and determined the best combination from selected active compounds with conventionally used antibiotics (macrolides, vancomycin and/or aminoglycosides) against MRSA. Also, by using human peripheral blood mononuclear cells and cultured macrophages, the inventors have evaluated the anti-inflammatory activities of the active compounds alone and in combination. Furthermore, the inventors used a mouse MRSA-induced pneumonia model to validate the active ingredients and antibiotic combination agents on their antibacterial and anti-inflammatory activities.

It has been demonstrated in the present study that the combined use of ECG from tea (*Camellia sinensis*) and kuraridin from Sophorae Flavescentis Radix is efficacious in inhibiting the growth of a panel of tested MRSA strains in vitro. The antibacterial activities of gentamicin, fusidic acid, and vancomycin were further enhanced by the addition of ECG and kuraridin. Both kuraridin and ECG not only are non-cytotoxic but they also possess anti-inflammatory activities. The combined use of ECG and kuraridin was able to reduce bacterial loading in MRSA-infected mice.

II. Compositions and Administration

The present invention thus provides pharmaceutical compositions or physiological compositions for suppressing bacterial growth or for treating bacterial infections. Such compositions comprise an effective amount of two or more of the anti-bacterial agents described herein (namely baicalein, berberine, gallic acid, kuraridin (or any one of its analogs set forth in Table 7, e.g., analog WQD175 or WQD165), epicatechin gallate (ECG), and tanshinone, as well as their functional derivatives), optionally with an additional compound with known anti-bacterial activity, such as any one of the conventional antibiotics. Use of the compositions can be in both prophylactic and therapeutic applications for the treatment and prevention of any disease or condition that is caused by or exacerbated by a bacterial infection, especially an infection due to antibiotic-resistant bacteria. Such pharmaceutical or physiological compositions also include one or more pharmaceutically or physiologically acceptable excipients or carriers, which are substances that are without any relevant therapeutic activity but are effective in formulating the composition to be more compatible for in vivo use. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, L. Jorgensen, H. M. Nielsen (Eds.) Delivery Technologies for Biopharmaceuticals, Wiley, 2009.

The composition of this invention may be administered to humans and other animals for therapeutic or prophylactic application by any suitable route of administration, including orally, nasally, as by, e.g., a spray, rectally, intravaginally, parenterally, intracisternally and topically, as by powders, ointments or drops, including buccally and sublingually. The composition may be given orally, parenterally, topically, or rectally and given by forms suitable for each administration route. For example, the composition is administered in tablets or capsule form, by injection, inhalation, eye lotion, ointment, suppository, infusion; topically by lotion or ointment; and rectally by suppositories. Oral administration is one of the preferred routes of administration.

Depending on the specific condition to be treated, formulations useful in the methods of the present invention include those suitable for oral, subcutaneous, transdermal, intramuscular, intravenous, intranasal, topical (including ophthalmic, optic, buccal, and sublingual), rectal, vaginal, aerosol and/or parenteral administration. The formulations may conveniently be presented in unit dosage form and may be prepared by any methods well known in the art of pharmacy. The amount of active ingredient to produce a single dosage form will vary depending upon the host being treated, the particular mode of administration. The amount of active ingredient for a single dosage form will generally be that amount of the compound which produces a therapeutic effect.

The more frequently used routes of administering the pharmaceutical compositions are oral or intravenous delivery to a patient in need thereof (e.g., a human patient who is diagnosed of or is at risk of developing a bacterial infection) at doses of about 10-100,000 mg, 100-10,000 mg, 50-5,000 mg, 1000, 2000, 2500, 4000, or 5000 mg of each of the anti-bacterial agent or antibiotic for a 70 kg adult human once every 12 hour or every day or every other day. Some exemplary doses and administration frequencies include about 0.5, 1, 2, 3, 4, 5, 6, 7, 8, 9, 10, 20, 30, 40, 50, 60, 70, 80, 90, 100, 120, 150, 200, 250, or 500 mg/kg patient body weight for each anti-bacterial agent and each antibiotic (in any combination) in each administration. Typically two or more anti-bacterial agents, optionally with an antibiotic, are administered to the patient either on once per 12-hour, per day or per two-day basis. As more than one therapeutic agent is administered, they can be administered at the same time or at separate times while all within the same general time frame. The anti-bacterial agents and antibiotic may be administered in a single pharmaceutical composition or they may be in multiple separate compositions. For example, when ECG, kuraridin (or any one of its analogs set forth in Table 7, e.g., analog WQD175 or WQD165), and vancomycin are used together, all three may be administered in a single combined pharmaceutical composition; or they may be administered in three separate compositions; or they may be administered in two separate compositions: e.g., the first being a saline solution containing ECG and vancomycin, and the second being an ethanol-containing solution of kuraridin (or any one of its analogs set forth in Table 7, e.g., analog WQD175 or WQD165). Similarly, these anti-bacterial agents/antibiotic may be administered at the same time, or they may be administered on different days but all in close proximity to each other's administration, e.g., one administered on day 1 and other or others administered on day 2, such that the combined effects of these therapeutic agents being co-administered are obtained. The appropriate dose may be administered in a single twice-daily/daily/bi-daily (once every other day) dose or as divided doses presented at appropriate intervals, for example as two, three, four, or more subdoses per day, or one dose every two, three, four, or five days.

For preparing pharmaceutical compositions of this invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an anti-bacterial agent or antibiotic. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient (e.g., an anti-bacterial agent or antibiotic). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active component of an anti-bacterial agent or antibiotic with encapsulating material as a carrier providing a capsule in which the anti-bacterial agent or antibiotic (with or without other carriers) is surrounded by the carrier, such that the carrier is thus in association with the anti-bacterial agent/antibiotic or the active component. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an anti-bacterial agent or antibiotic) or sterile solutions of the active component in aqueous or organic solvents comprising water, buffered water, saline, PBS, ethanol, or propylene glycol are examples of liquid compositions suitable for parenteral administration including subcutaneous, intramuscular, intravenous, or intraperitoneal administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an anti-bacterial agent or antibiotic) in the desired solvent system, and then passing the resulting solution through a membrane filter to sterilize it or, alternatively, by dissolving the sterile compound in a previously sterilized solvent under sterile conditions. The resulting aqueous or oragnic solutions may be packaged for use as is, or lyophilized, the lyophilized preparation being combined with a sterile aqueous carrier prior to administration. The pH of the preparations typically will be between about 3 and about 11, more preferably from about 5 to about 9, and most preferably from about 7 to about 8.

The pharmaceutical compositions comprising an anti-bacterial agent or antibiotic can be administered to a patient who have received a diagnosis of bacterial infection or is at risk of developing such an infection at a later time in an amount sufficient to prevent, eliminate, reverse, or at least partially slow or arrest the symptoms of the infection such as any of the clinical symptoms of the cytotoxicity related to, caused by, or enhanced by the infection, especially by bacterial species that have become resistant to antibiotics. An amount adequate to accomplish this goal is defined as a "therapeutically effective dose." Amounts effective for this use will depend on the (expected) severity of the condition, route of administration, frequency of administration, and the body weight and general physical state of the patient, but generally range from about 0.5 mg to about 1000 mg per kg patient body weight, about 1 or 2 mg/kg to about 500 mg/kg, about 5-500 mg/kg, about 10-100 mg/kg, about 20-50 mg/kg, e.g., about 10, 20, 25, 30, 40, 50, or 80, 100, 150, 200, or 300 mg/kg body weight for each anti-bacterial therapeutic agent and antibiotic in all potential combinations in each administration. Depending on the specific identity of the two or more anti-bacterial agents and depending on the specific application, the agents may be administered at a certain weight ratio to each other. For example, in the case of combination use of ECG and kuraridin (or any one of its analogs set forth in Table 7, e.g., analog WQD175 or WQD165), their relative weight ratio may range from about 1:4 to about 4:1, such as about 1:4, 1:3, 1:2, 1:1, 2:1, 3:1, or 4:1. In other examples, each of ECG (at about 0.1-5 mg/kg, e.g., about 0.1, 0.2, 0.25, 0.5, 0.75, 0.8, 1, 1.5, 2, 2.5, 3, 3.5, 4, 4.5, or 5 mg/kg), kuraridin (or any one of its analogs set forth in Table 7, e.g., analog WQD175 or WQD165) (at about 0.1-5 mg/kg, e.g., about 0.1, 0.2, 0.25, 0.5, 0.75, 0.8, 1, 1.5, 2, 2.5, 3, 3.5, 4, 4.5, or 5 mg/kg), and vancomycin (at above 0.1-8 mg/kg, e.g., about 0.1, 0.2, 0.25, 0.5, 0.75, 0.8, 1, 1.5, 2, 2.5, 3, 3.5, 4, 4.5, 5, 5.5, 6, 6.5, 7, 7.5, or 8 mg/kg) in any potential combinations of above-named concentrations may be used in the combination administration.

Single or multiple administrations of the compositions can be carried out with dose levels and pattern being selected by the treating physician. In any event, the pharmaceutical formulations should provide a quantity of an anti-bacterial agent or antibiotic sufficient to effectively inhibit the undesired symptoms in the patient relating to bacterial growth or proliferation. Typically, the administration lasts at least 1, 2, 3, 4, 5, 6, or 7 days, or up to 1, 2, or 3 weeks and for as long as needed such as 1 or 2 months, on a daily, twice a day, bi-daily (once every other day), or weekly schedule.

In light of the present inventors' discovery that combination use of two or more anti-bacterial agents can enhance the efficacy of conventional antibiotics and/or overcome drug-resistance in bacteria, a variety of antibiotics can be used together with the anti-bacterial agents (e.g., ECG and kuraridin, or any one of its analogs set forth in Table 7, e.g., analog WQD175 or WQD165) including broad spectrum or general and "narrow spectrum" or specific antibiotics, bactericidal antibiotics and bacteriostatic antibiotics, such as amoxicillin, ampicillin, ciprofloxacin, erythromycin, fusidic acid, gentamicin, kanamycin, and vancomycin.

III Kits

The present invention also provides novel kits that can be used for improved therapeutic efficacy in treating bacterial infections, especially by drug-resistant bacterial species such as MRSA. For example, in a kit for treating bacterial infection included are a first container containing a first composition comprising an effective amount of a first anti-bacterial agent and a second container containing a second composition comprising an effective amount of a second anti-bacterial agent. The first and second anti-bacterial agents are selected from the group consisting of baicalein, berberine, gallic acid, kuraridin (or any one of its analogs set forth in Table 7, e.g., analog WQD175 or WQD165), epicatechin gallate (ECG), and tanshinone, for example, ECG and kuraridin (or any one of its analogs set forth in Table 7, e.g., analog WQD175 or WQD165). The kit may further include an effective amount of an antibiotic (e.g., vancomycin), which may be present in a third composition or may be included in the first or second composition. In some cases, the kit includes three separate containers, each containing a separate composition comprising a first anti-bacterial agent (e.g., ECG), a second anti-bacterial agent (e.g., kuraridin or its analog such as WQD175 or WQD165), and a conventional antibiotic (e.g., vancomycin), all in an effective amount for each of the active ingredients. In other cases, the kit includes two separate containers: one containing a composition comprising a first anti-bacterial agent (e.g., ECG) and a conventional antibiotic (e.g., vancomycin), the other containing a composition comprising an effective amount of a second anti-bacterial agent (e.g., kuraridin or its analog such as WQD175 or WQD165). One exemplary kit includes two separate containers: the first container contains a composition comprising an effective amount of ECG and an effective amount of vancomycin, and the composition is an aqueous solution such as a saline solution. The second container contains another composition comprising an effective amount of kuraridin, and the composition is an aqueous solution comprising an organic solvent such as ethanol to ensure solubility of kuraridin (or any one of its analogs set forth in Table 7, e.g., analog WQD175 or WQD165).

The compositions included in the kit are formulated for the intended delivery method of the anti-bacterial agent, for example, by injection (intravenous, intraperitoneal, intramuscular, or subcutaneous injection) or by oral ingestion or by local deposit (e.g., suppositories or topical cream/paste). The compositions can be packaged in individual dosage form so that one individually packaged composition is administered each time to deliver an effective amount of the active agent (an anti-bacterial agent or antibiotic). When appropriate, one or more physiologically or pharmaceutically acceptable excipients/carriers are included in the compositions to ensure proper formulation consistent with the intended use. Typically, the kit will further include printed material providing detailed instructions for users of the kit, such as providing information of the schedule and dosing arrangement for administering the first and second (and optionally third) compositions to a recipient.

EXAMPLES

The following examples are provided by way of illustration only and not by way of limitation. Those of skill in the art will readily recognize a variety of non-critical parameters that could be changed or modified to yield essentially the same or similar results.

Example 1: Combination Treatment of Bacterial Infection

Introduction

Resistance to antimicrobials is a significant and growing problem with limited treatment options, especially for serious Gram-positive infections. Among them, methicillin resistant *Staphylococcus aureus* (MRSA) is the major cause of worldwide outbreaks for both hospitals and community infections (1-3) that lead to multiple illnesses ranging from mild skin irritations to severe life threatening invasive disease such as necrotizing pneumonia (4). In Hong Kong, MRSA accounts for 58.2% of *S. aureus* isolated from blood cultures and 69.8% of all *S. aureus* isolates in our public hospitals (5). Notification of community associated (CA)-MRSA has been made mandatory in Hong Kong (6, 7). MRSA infections are also associated with a remarkably severe and prolonged host inflammatory response and this host response to severe *S. aureus* infections is triggered by the exposure of Staphylococcal superantigens such as Staphylococcal enterotoxin B (SEB) to host macrophages, stimulating the production of proinflammatory mediators (8). At present, glycopeptide antibiotics, such as vancomycin, have traditionally been the mainstay of treatment of MRSA but overuse has led to the emergence of vancomycin-resistant strains (9). Hence, alternative therapeutic strategies to identify new agents and paired with existing antibiotics to restore the efficacy against MRSA are urgently needed. Herbal sources from Traditional Chinese Medicines (TCM) elaborate a vast array of natural products, either as pure compounds or as standardized plant extracts, provide unlimited opportunities for new drug leads due to the unmatched availability of chemical diversity. It is also commonly accepted that a significant part of this chemical diversity is related to defense mechanisms including resistance to microbiological attack (10).

Using a panel of Chinese herbs with a systematic screening of their growth inhibition with a panel of bacteria strains, the present inventors have identified in their previous studies (11-14) 6 herbs and some of their active ingredients exhibiting promising anti-MRSA activities. From Sophorae Flavescentis Radix (苦參), they isolated a non-cytotoxic chalcone named kuraridin, which showed significant antibacterial effects against a panel of MRSA strains [minimum inhibitory concentration (MIC) around 8 µg/ml] (12). Another active ingredient baicalein from Scutellariae Radix (黃芩), which was weak in killing MRSA but could significantly reverse the ciprofloxacin resistance of MRSA 1199B and 20 clinical MRSA strains from Hong Kong by inhibiting both the NorA efflux pump and a newly discovered MRSA pyruvate kinase, an enzyme essential for *S. aureus* growth and survival (14). It was also found that extracts from Coptidis, Rhizoma (黃連), Salviae Miltiorrhizae Radix et Rhizoma (丹參), Moutan Cortex (牡丹皮) and green tea (綠茶) were active in suppressing MRSA growth (11, 13). The plant alkaloid berberine is an active ingredient of Coptidis Rhizoma, and its mild antimicrobial action was potentiated by a multidrug pump inhibitor, 5'-methoxyhydnocarpin, from 32 to 2 µg/ml against NorA overexpressed *S. aureus*. Tanshinone is an active ingredient of Salviae Miltiorrhizae Radix et Rhizoma which contributes to the antimicrobial activities. Gallic acid is the active ingredient from Moutan Cortex (15) and epicatechin gallate (ECG) from green tea at 20 µg/ml exhibited a four-fold potentiation of the activity of norfloxacin against a norfloxacin-resistant strain of S. aureus overexpressing the NorA multidrug efflux pump (16). Apart from direct and adjuvant antibacterial activities, most of these active ingredients have been shown to possess anti-inflammatory activities which favour the use in anti-MRSA treatment. However, plant antimicrobials are not used as systemic antibiotics directly or as adjuvant with conventional antibiotics in clinics at present. The main reason for this is that their activities alone are not potent enough at clinical situation when compared with conventionally used antibiotics (17). To tackle this problem, combinations for better synergy (e.g., triple combinations) may reduce the agents' dose and the adverse reactions. Antibiotic combination therapy has long been used in an attempt to improve clinical outcomes, particularly in patients with infections that are associated with high rates of morbidity and mortality such as persistent bacteraemia, necrotizing pneumonia and other deep-seated sites of infections (18). However, no systematic studies for combinations of promising active ingredients from natural products have been reported. Combinations of these natural compounds at optimal doses as an adjuvant therapy with antibiotics may offer an excellent opportunity to maximize clinical outcomes, particularly in the case of antibacterial resistance, and to broaden the spectrum of antibiotic activity.

From 6 promising candidates (baicalein, berberine, epicatechin gallate, kuraridin, gallic acid and tanshinone), which were selected based on the previous reports, the inventors intended to further develop an effective non-toxic herbal active ingredients and antibiotics combination for MRSA treatment with antibacterial and anti-inflammatory activities. By using a panel of laboratory and clinical MRSA strains, they determined the best combination from 6 selected active compounds from TCM with conventionally used antibiotics (macrolides, aminoglycosides, and/or vancomycin) against MRSA. By using human peripheral blood mononuclear cells and cultured macrophages, they evaluated the anti-inflammatory activates of the active compounds alone and in combination. By using different human cell types, they evaluated the cytotoxicity of the promising combination of the active compounds. By using a mouse MRSA-induced pneumonia model, they studied the active ingredients and antibiotic combination agents with both antibacterial and anti-inflammatory activities.

Materials and Methods
Active Ingredients and Antibiotics

Based on previous studies, baicalein, berberine, gallic acid, kuraridin, epicatechin gallate (ECG) and tanshinone were selected for testing. Major classes of antibiotics typically used in MRSA treatment, including ciprofloxacin, erythromycin, fusidic acid, gentamicin, kanamycin and vancomycin, were used. The goal of this study was to work out two of the natural compounds that can provide that best synergy with antibiotics against MRSA. ECG and kuraridin were purchased from SR Pharmasolutions (Hong Kong, China), and all other chemicals were purchased from Sigma Chemical Company (St Louis, Mo., USA).

Antibacterial Tests
Bacterial Strains and Preparation of Bacteria Culture

Six S. aureus strains with different antibiotics resistance were used. SA-ST239, a representative strain of MRSA, is a healthcare-associated multidrug-resistant strain which is prevalent in Asian countries. S. aureus SA-1199B (harboring resistance to fluoroquinolones through overexpression of the NorA efflux pump) is ciprofloxacin resistant. SA-RN4220-pUL5054 is resistant to 14- and 15-membered macrolides including erythromycin and contains the multicopies plasmid pUL5054 coding for methionine sulfoxide reductase A (MsrA), an efflux pump. Three experimentally induced aminoglycosides resistant strains through methylation of specific nucleotides within the A-site of rRNA hampering the binding of aminoglycosides were also included in this study: a) SA-APH2"-AAC6' (aminoglycoside-6'-N-acetyltransferase/2"-O-phosphoryltransferase) is resistant to gentamicin, b) SA-APH3' (aminoglycoside-3'-O-phosphoryltransferase) is resistant to kanamycin, and c) SA-ANT4' (aminoglycoside-4'-O-phosphoryltransferase) is resistant to fusidic acid. A methicillin sensitive strain: S. aureus ATCC25923 was used as a control strain. 23 non-duplicate hospital associated (HA)-MRSA and community associated (CA)-MRSA clinical isolates were also used for further screening.

Screening for Selected Active Ingredients and their Combinations Showing the Best Beneficial Effect in Combination with Antibiotics The screening of antibacterial activities were performed in liquid medium by using a Biomek 2000 robot (Beckman), a robot accommodating 96-well plates, with UV/visible light and fluorescence detector and micro titration plates. The final volume in each well was 200 µl ($5\times10^5$ CFU/ml). Twenty microliters of DMSO solution of extracts or compounds were added to each well of the plate. The highest concentration of DMSO remaining after dilution (1%, v/v) that caused no inhibition of bacterial growth cultures. The plates were incubated at 35±2° C., and bacterial growth was monitored at 650 nm after 24 h of growth. The minimum inhibitory concentration (MIC) of the fractions and antibiotics were determined by using two-fold dilution technique in Mueller-Hinton broth and MIC was defined as the lowest concentration at which there was no visible growth at 35±2° C. for 24 h.

Checkerboard Assay (19) and Time Kill Curves (20)

Initially, six S. aureus strains were used to identify the synergistic interactions of different combinations of active ingredients by checkerboard arrays with multiple delusional combinations of three antimicrobial agents in a concentration range from below to above the MIC were performed in a 96-well microtiter for 24 h at 37° C. Fractional inhibitory concentration (FIC) indices for triple combinations (15) were calculated as follows: FIC index (FICI)= $FIC_{drug\ A} + FIC_{drug\ B} + FIC_{drug\ C} = (Ccomb_{drug\ A}/MIC_{drug\ A}) + (Ccomb_{drug\ B}/MIC_{drug\ B})(Ccomb_{drug\ C}/MIC_{drug\ C})$, where $Ccomb_{drug\ A}$, $Ccomb_{drug\ B}$ and $Ccomb_{drug\ C}$ were the concentrations of drugs tested; and $MIC_{drug\ A}$, $MIC_{drug\ B}$, and $MIC_{drug\ C}$ were the MICs of the compounds when used alone. The results were analysed numerically as a FIC and could therefore be used universally to describe antibiotic interactions as synergistic, additive or antagonistic. The Lorian definition of synergy in Checkerboard assay was that an FIC index of ≤0.5.

After determining the MIC of the six active ingredients against the strains, triple combination checkerboard assay of the active ingredients with the antibiotics against the selected strains were performed to look for best combinations of the chosen active ingredients from TCM with the antibiotics. The concentrations of antibiotics and active ingredients were ranged from 0 to the MIC (µg/ml). The best two combinations of active ingredients that exhibited good synergy (FICI<0.5) with antibiotics against the MRSA with more than one known resistance mechanisms were subjected to further testing on the major clonal types and the clinical MRSA strains and determining the best combination with major class of antibiotics, so that the best combination could be obtained. For best candidate chosen (2 natural products combined with antibiotics) from the initial screening with laboratory MRSA strains, a panel of clinical MRSA strains were used to validate the antibacterial activities of this combination.

For time-kill curves, active natural compounds and antibiotics combinations; and normal saline (as control) with bacteria in MH medium were growth for 24 h. The time-kill curves for the bacteria of each extract were determined by CFU counting. Ten microliters of broth from each preparation were taken at 0 h and after 2, 4, 8 and 24 h of incubation for bacterial counts. Each aliquot was serially diluted and plated onto MH agar plates, in duplicates and incubated overnight at $35\pm2°$ C. for 18-24 h and the number of CFU/mL was determined.

Anti-Inflammation Effects and Cytotoxicity of Active Ingredients

*S. aureus* is a major human pathogen that produces a wide array of toxins such as SEB, thus causing various types of disease symptoms. During the early stages of infection, host innate immune cells, such as monocytes, produce a number of pro-inflammatory cytokines, including IL-1β, IL-6, IL-12, and TNF-α. This cytokine milieu drives pro-inflammatory T cell responses that can result in substantial damage to host tissues. Thus, to evaluate the anti-inflammatory actions of the selected active ingredients to see whether the chosen active ingredients could suppress the inflammatory cytokines from the immune cells, human peripheral blood mononuclear cells (PBMC) consisting of T cells, B cells, monocytes, dendritic cells (DC), natural killer (NK) cells and human cultured macrophages were used.

PBMC and Macrophages Studies

PBMC were isolated from buffy coat of healthy adult donors (Red Cross, Hong Kong SAR, China) by Ficoll-Paque Plus density gradient (Amersham Biosciences, Uppsala, Sweden) according to the supplier's instruction. PBMC were adjusted to a concentration of $2\times10^6$ cells/ml in a falcon tube, and 100 µl aliquots of cell-suspension were placed in a culture plate. PBMC were cultured with SEB/peptidoglycan (PGN) and, active herbal ingredients, or PGN/SEB in combination with active herbal ingredients for 24 h in 95% humidified air containing 5% $CO_2$ at 37° C. and the supernatants were collected by centrifugation and stored at −70° C. Pro-inflammatory T cells associated cytokines, including TNF-α, IL-1β and IL-6 in culture supernatants were determined by human cytokine ELISA kits (BD Biosciences, San Diego, Calif., USA) according to the manufacturer's instruction with detection limits ranged from 3.1 to 7.8 µg/ml. For macrophage study, monocytes were isolated from PBMC by attachment. The cells were plated at $2\times10^6$ per ml per well in 24-well plate and let them adhered for 45 min, at 37° C. and 5% $CO_2$. Non-adherent cells were removed by washing the wells two to three times with a gentle stream of medium. The isolated monocytes were allowed to differentiate for 14 days in vitro supplemented with 5% of autologous plasma and were induced by peptidoglycan (PGN) or Staphylococcal endotoxin B (SEB) (10 µg/ml) in the presence of active herbal ingredients alone and in combination. The supernatants from macrophages cultures were collected after harvesting the cells and stored at 80° C. until assayed for cytokines. The levels of TNF-α, IL-12, IL-10 and IFN-γ were determined by human ELISA Kits (BD Biosciences, San Diego, Calif., USA). The study protocols of using human blood samples had been approved by the Joint Chinese University of Hong Kong-New Territories East Cluster Clinical Research Ethics Committee (Ref. No. CRE-2013.365).

XTT (Sodium 3'-[1-(phenylaminocarbonyl)-3,4-tetrazolium]-bis (4-methoxy-6-nitro) Benzene Sulfonic Acid Hydrate) Cytotoxicity Testing Before animal studies, the cytotoxicity of the promising combination of the active compounds were determined by XTT assay (21) using three primary cells: i) buffy coat purified human peripheral mononuclear cells (PBMC) collected from Hong Kong Red Cross, ii) Human Umbilical Vein Endothelial Cells (HUVEC), and iii) Human Mammary Epithelial Cell (HMEC). Cells were plated in 96-well plates at $10^5$ cells/well. Serial dilutions of the compounds were added to the wells. The plates were maintained in a 37° C. incubator. After 3 days, 50 µl of XTT/PMS solution (20 µM) were added to each well. Then, the plates were incubated at 37° C. for 4 h. The OD of the wells was determined by a spectrophotometer at 450 nm. The toxicity represents the ratio of OD of a well in the presence of compounds with the OD of control wells in the presence of medium containing DMSO. The cellular viability of at least 85% was considered to indicate a non-toxic compound.

Animal Studies—Mouse Pneumonia Model

A murine lung infection model (22) was used to validate the in vivo efficacy of kuraridin and ECG in combination with vancomycin against MRSA. The animal study protocols had been approved by the Animal Experimentation Ethics Committee of The Chinese University of Hong Kong (Ref. No. 12/071/MIS). Anesthetized Balb/c mice aged 7-9 weeks were inoculated with $1\times10^7$ to $2\times10^8$ selected MRSA and standard strains: ST239, Panton-Valentine leukocidin positive CA-MRSA strain (ST30) and ATCC25923 in a volume of 20 µl intranasally. The freshly prepared stock solution of kuraridin was dissolved in ethanol. ECG and vancomycin were dissolved in normal saline. A vehicle control group, which was infected with MRSA and received diluted ethanol in normal saline was included.

First, treatment and control regimens were initiated 2 h post-inoculation, ST30 infected mice (4 per therapy) were randomized to receive vancomycin, ECG or kuraridin (30, 60 or 120 mg/kg every 12 hours two times daily for 2 days) as monotherapy to determine the sub-MIC dosage for the active ingredients/antibiotics combination synergistic studies. All antimicrobials (0.1 ml) were administered subcutaneously (23, 24). Mortality of control and therapeutic groups were recorded during 48 h of therapy. The animals were then sacrificed by cervical dislocation. Left lung of the animals used for bacteriological analyses were homogenized in saline (0.1 g of tissue to a final volume of 1 mL), serially diluted and cultured on blood agar plates.

In the second phase of the experiments, the best combinations of active ingredients/antibiotics at sub-MIC dosage and single MIC dosage of the corresponding MRSA sensitive antibiotics as positive control were chosen with reference to the initial phase results for the synergistic studies using this animal model. ST30, ST239 and ATCC25923 were used. ATCC25923 and ST293 were not effectively infected in balb/c mice even the inoculations were at $1\times10^9$ CFU. For infecting these two bacteria strains in balb/c mice, the protocols were modified by inducing the mice with neutropenia prior to the infection using cyclophosphamide or CHX (intraperitoneally injection with 150 and 100 mg/kg cyclophosphamide on 96 h and 24 h before infection, respectively) (25). Blood were obtained from live animals at 0 and 48 h for cytokine assays. After treatment, the animals (n=10 for each group) were then sacrificed by cervical dislocation; the lungs were dissected and removed under aseptic conditions for bacterial loading and pneumonia assessment. Left lungs were used for bacteriological and cytokines analyses were homogenized in saline (0.1 g of tissue to a final volume of 1 mL), serially diluted and cultured on blood agar plates. For pneumonia assessment, right lungs of the animals were perfused with 1 ml of 10% neutral-buffered formalin. The tissues were dehydrated and embedded in paraffin, cut and stained with hematoxylin and eosin. The stained sections were examined by light microscopy to assess the level of inflammation. Evidence of pneumonia was determined by histopathological and was scored (0-5) according to the levels of leukocyte and erythrocyte infiltration, alveolar integrity and epidermis damage: (Score=0)—No lesions, no leukocyte or erythrocyte infiltrate & normal epithelia; (Score=1)—No lesions, except some leukocyte infiltration; (Score=2)—No lesions, some leukocytes and erythrocytes in the airspace but the alveolar structure is preserved; (Score=3)—1 to 2 lesions smaller than 500 μm in length/width or many smaller ones, some leukocyte and erythrocyte infiltrate in the alveoli, but the alveolar structure is preserved, no epithelial damage; (Score=4)—Less than 3 lesions smaller than 1,000 μm in length/width; leukocytes and erythrocytes throughout the lesion, alveolar structure not preserved within the lesion, some epithelial damage; (Score=5)—More than 3 lesions 1,000 μm in length/width, leukocytes and erythrocytes throughout the lesion, alveolar structure not preserved within the lesion.

For immunomodulation assessment of using ST30, the homogenates from the left lungs and the mice sera obtained were used. The cytokines known to boost innate immunity (TNFα), as well as some markers of inflammation (e.g., IFN-γ, IL-1β, IL-6 and IL-10), were detected by ELISA kits for mouse (BD Biosciences, San Diego, Calif., USA).

Statistical Analysis

Statistical analyses and significance, as measured by the Student's t-test were performed using GraphPad PRISM software version 4.0 (GraphPad Software, San Diego, Calif., USA). In all comparisons, $p<0.05$ was considered as statistically significant.

Results
The Combination of Epicatechin Gallate (ECG) and Kuraridin Potently Inhibit MRSA Growth By using a panel of laboratory strains (Table 1), the present inventors discovered that kuraridin was the most potent among all tested compounds in inhibiting the growth of MRSA (MIC99: 8-16 μg/ml), followed by ECG (MIC90: 4-16 μg/ml), but the inhibitory activities of ECG could not be reached by 99.9% even at 512 μg/ml. Baicalein, berberine and gallic acid were relatively weak against the tested MRSA strains when used alone. For tanshinone, the solubility was poor and the highest tested concentration was 128 μg/ml and was ineffective against the growth of MRSA.

In combination tests using two compounds among the 6 selected candidates, 2 combinations of the tested compounds were identified with synergistic activities against MRSA and were summarized in Table 2. Baicalein and ECG combined treatment was able to synergistically inhibit the growth of NorA efflux pump overexpressed 1199B strain. A better partner was as follows: kuraridin and ECG combined treatment was able to synergistically suppress the growth of all tested laboratory strains with known resistance mechanisms. The MICs of ECG and kuraridin on various strains ranged from 0.5 to 32 μg/ml and 2-4 μg/ml, respectively.

When further tested with a panel of clinical community-associated (CA) (Table 3a) and hospital-associated (HA) (Table 3b) MRSA strains, the combined treatments of kuraridin and ECG were also effective against the tested clinical strains. The MICs of ECG and kuraridin on various strains ranged from 0.25 to 8 μg/ml and 1-4 μg/ml, respectively.

The Combination of ECG and Kuraridin Enhanced Efficacy of Gentamicin and Fusidic Acid Additively Against MRSA When testing the enhancement of combinations of kuraridin and ECG on antibiotics efficacy, the inventors discovered that they could enhance the efficacy of gentamicin and fusidic acid on their resistant strains (Table 4). APH2 is highly resistant to gentamicin (MIC>512 μg/ml), the combination of kuraridin (2 μg/ml) and ECG (0.25 μg/ml) with gentamicin (16 μg/ml) could overcome the gentamicin resistance of APH2 (Table 4(a)). Three clinical MRSA strains (W231, W233 and W238) with gentamicin resistance were also tested, and it was discovered that kuraridin (2 μg/ml) and ECG (0.25 μg/ml) combined treatment was most effective against W231 and reduced the MIC of gentamicin by 6 fold (from 64 to 1 μg/ml) While W233 and W238 were more resistant to gentamicin, kuraridin and ECG combined treatment could only reduce the MIC of gentamicin by 5 folds (512 to 16 μg/ml). ANT4 is resistant to fusidic acid (MIC: 64 μg/ml), the combination of kuraridin (2 μg/ml) and ECG (0.25 μg/ml) with fusidic acid (4 μg/ml) overcame the fusidic acid resistance of ANT4 (Table 4(b)). The combination of kuraridin and ECG was also effective in enhancing fusidic acid against 3 clinical fusidic acid resistant strains (82356, 73621 and 96591) and reduced the MIC of fusidic acid from 32 to 1 μg/ml.

The Combination of ECG and Kuraridin Enhanced Vancomycin Efficacy Against MRSA

Figure 1B:
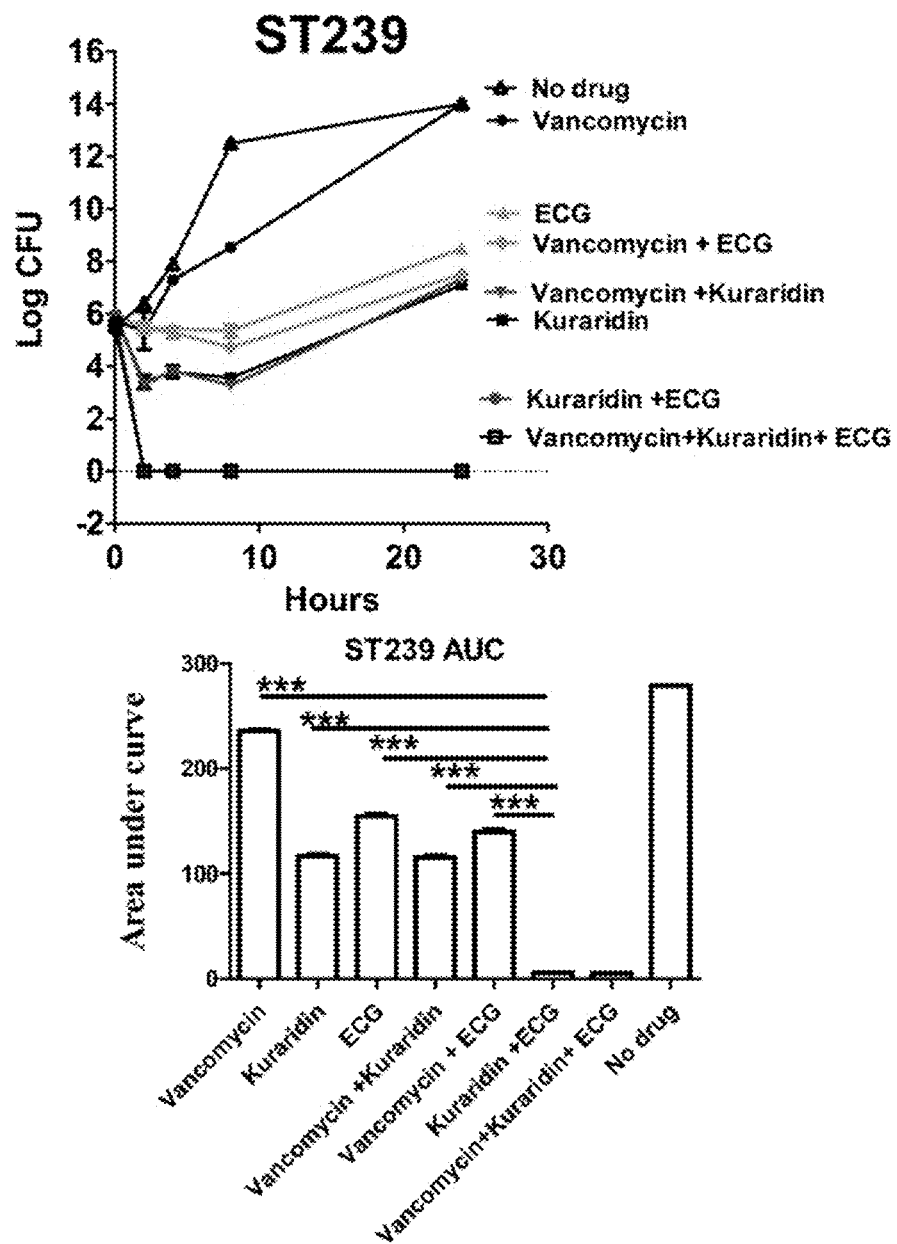
Figure 1C:
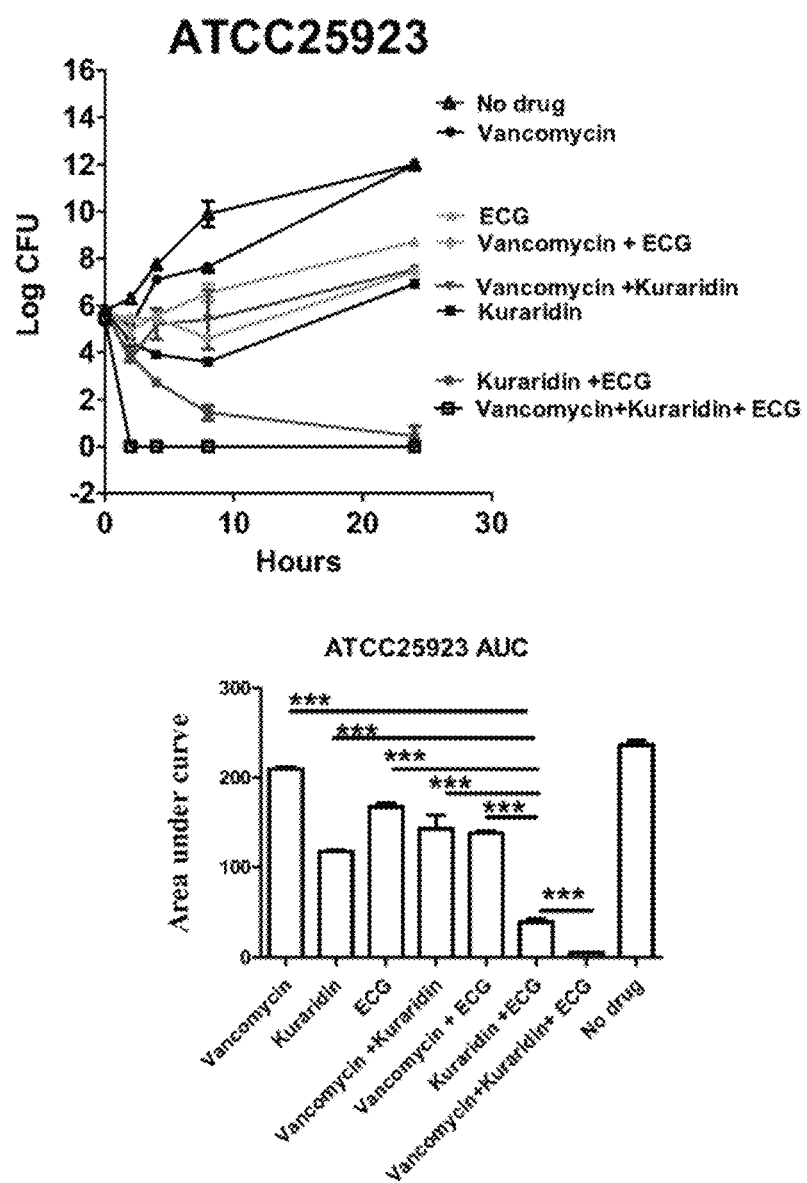

Vancomycin is commonly used in MRSA treatment and was examined to see whether or not the combination of ECG and kuraridin would enhance vancomycin against MRSA. Tested in a panel of clinical strains, ECG and kuraridin combined treatment was shown to reduce the MIC of vancomycin from 1 to 0.5 μg/ml (Table 5). The time-kill studies were further performed by using 2 representative clinical strains ST30 and ST239 (FIG. 1). When ECG (2 μg/ml) and kuraridin (2 μg/ml) were combined with vancomycin (0.5 μg/ml), they could kill both tested strains from 2 to 24 h. In time-kill studies using 2 representative clinical strains ST30, ST239 and the standard S. aureus strain ATCC25923 (FIG. 1), the combination of ECG (2 μg/ml) and kuraridin (2 μg/ml), with vancomycin (0.5 μg/ml), could bactericidally inhibit the growth of 3 tested strains from 2 to 24 h. When the data were further expressed as area under the curve (AUC), the AUC of the triple combination: ECG, kuraridin and vancomycin were the smallest compared with other drug combinations in three tested strains. The AUC of kuraridin and ECG were significantly smaller than other double combinations and single use in ATCC25923 and ST239. In summary, triple combination of ECG, kuraridin and vancomycin were the best in killing the tested MRSA strains.

Kuraridin and ECG were Non-Toxic to Human Cells: Human Peripheral Mononuclear Cells (PBMC), Human Mammary Epithelial Cells (HMEC) and Human Umbilical Vein Endothelial Cells (HUVEC)

Figure 2:
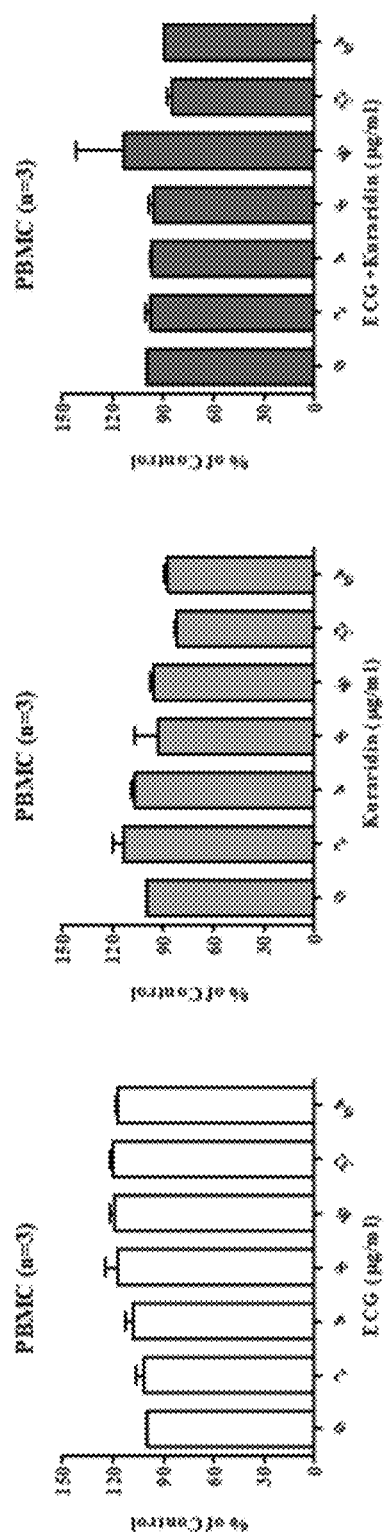
FIG. 2 Cellular toxicity (XTT assay) of epicatechin gallate (ECG) and kuraridin on human peripheral blood mononuclear cells (PBMC), human mammary epithelial cells (HMEC) and human umbilical vein endothelial cells (HUVEC). The results were expressed as % growth of drug free control±standard error of mean (n=3).
Figure 2:
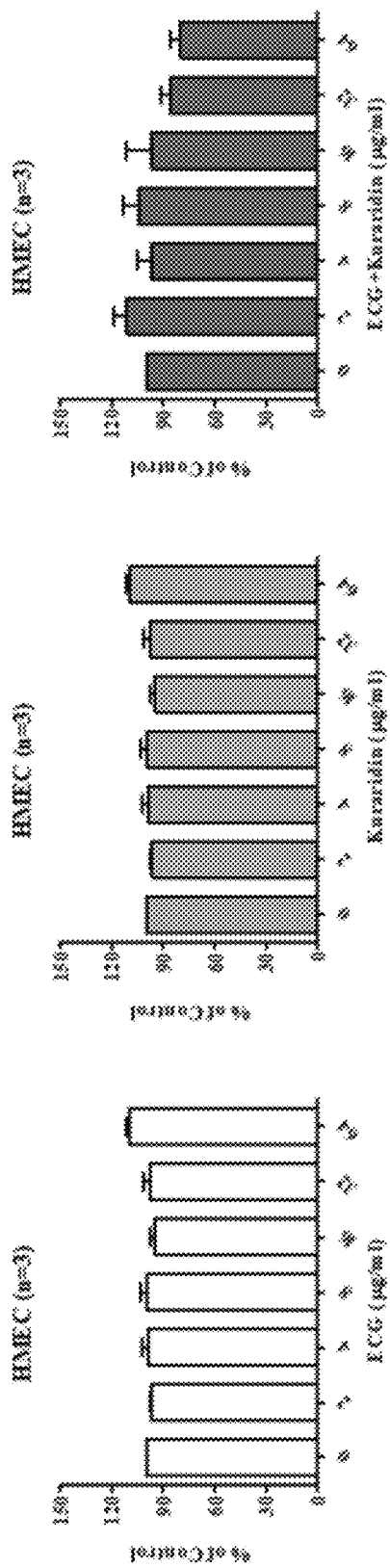
Figure 2:
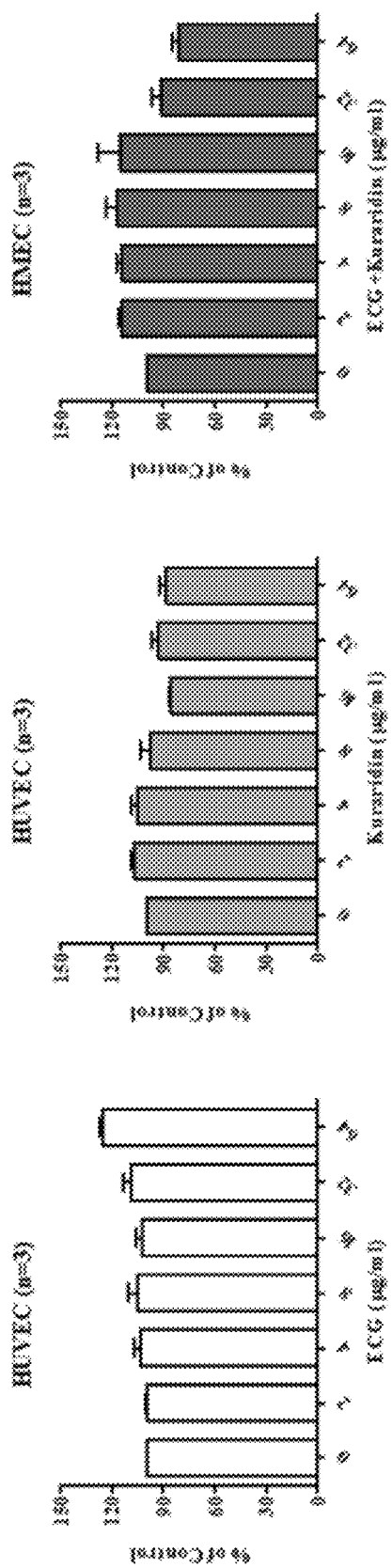

Cytotoxicity of kuraridin and ECG on above-mentioned human cells were determined by sodium 3'[1-(phenylaminocarbonyl)-3,4-tetrazolium]-bis (4-methoxy-6-nitro) benzene sulfonic acid hydrate (XTT) assay. Both tested compounds, ECG (FIG. 2, left column) and kuraridin (FIG. 2, middle column) from 2-64 μg/ml, when used alone or in combination (FIG. 2, right column), were not toxic to the tested cells when compared to drug free control.

Figure 3A:
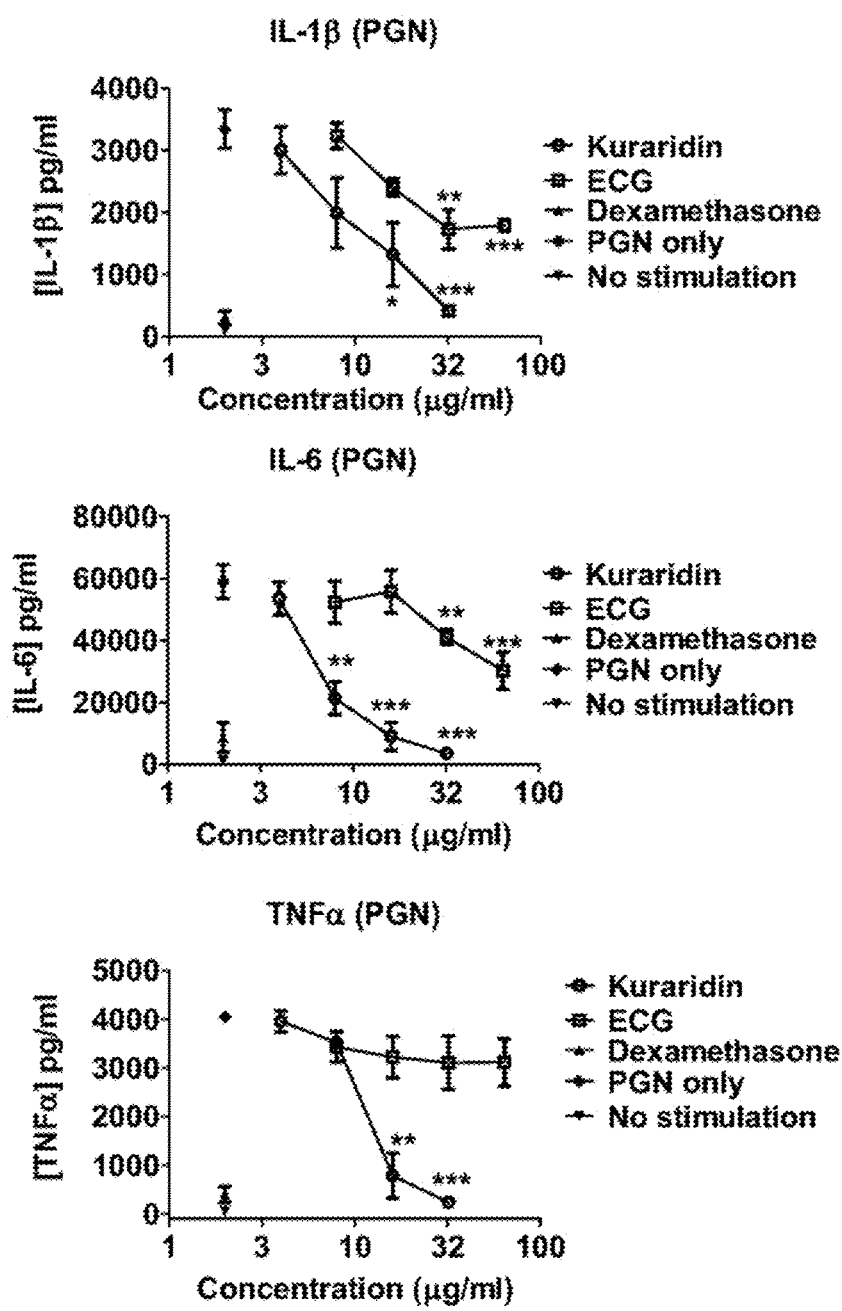
FIGS. 3A-3B Effects of epicatechin gallate (ECG) and kuraridin on cytokines production of human peripheral blood mononuclear cells (PBMC) stimulated with (FIG. 3A) Peptidoglycan (PGN) and (FIG. 3B) Staphylococcal enterotoxin B (SEB)(n=4). Dexamethasone (Dex) at 1 µg/ml was used as positive control. PGN (0.1 µg/ml) or SEB (10 µg/ml) was used to stimulate the PBMC to produce cytokines. Kuraridin or ECG (4-64 µg/ml) was added to the cells and the cell supernatant was collected for cytokine assays. Significant results by comparing the drug treatment groups with the drug free control are indicated ($*p<0.05$; $p<0.01$; $*p<0.001$).
Figure 3B:
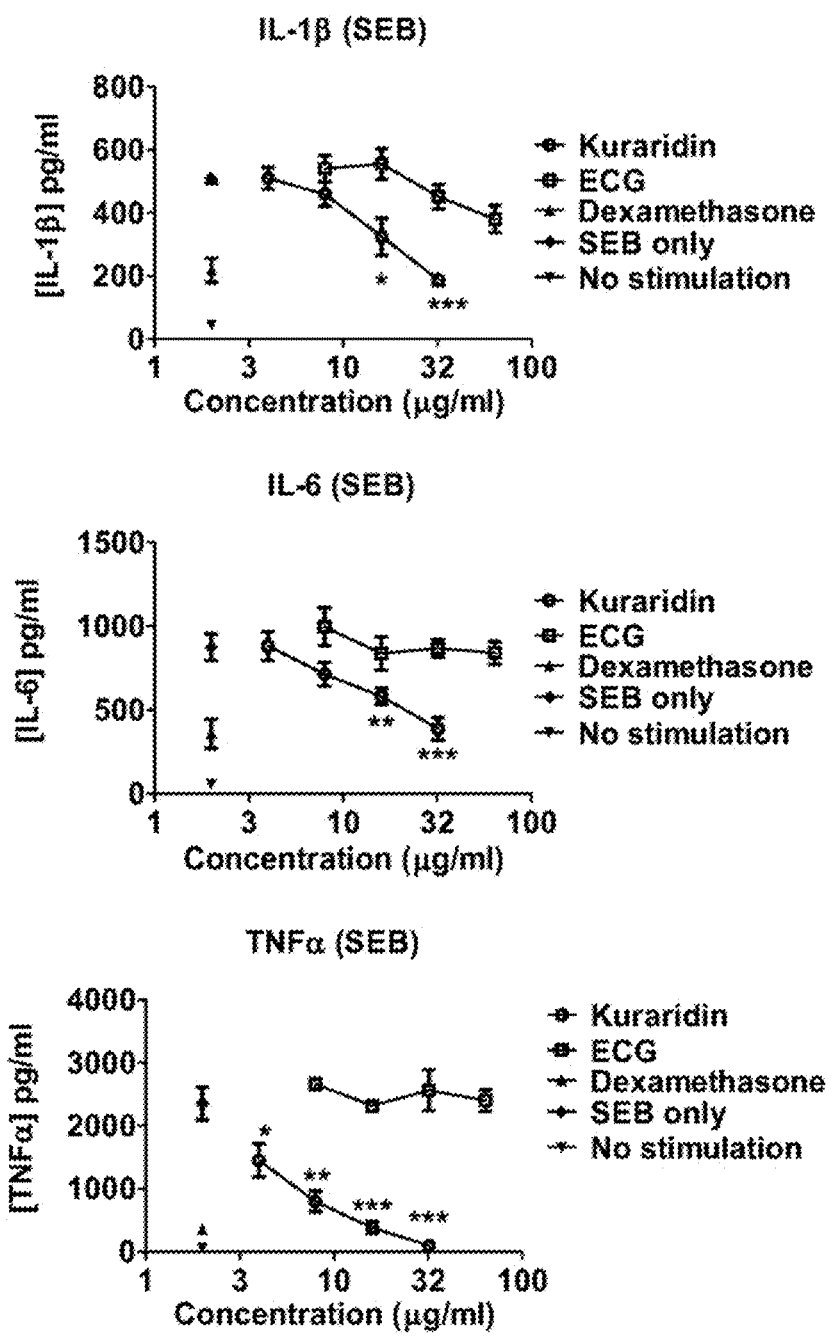
Figure 4A:
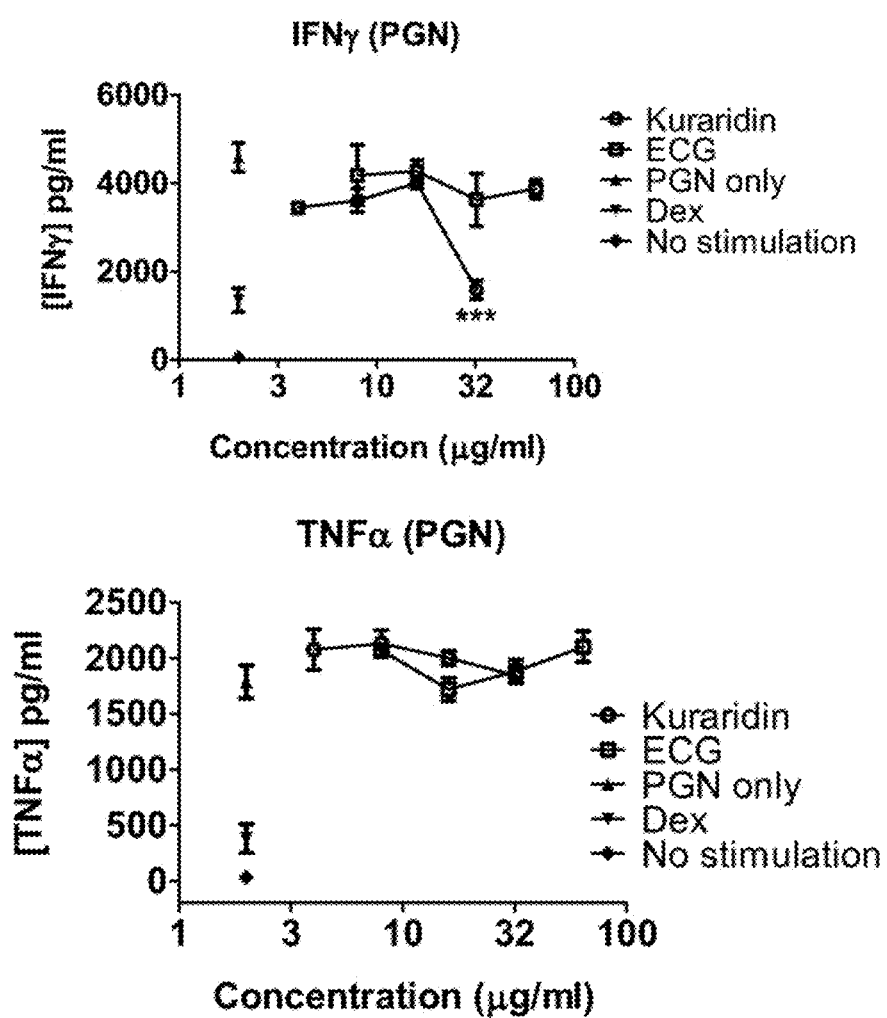
FIGS. 4A-4B Effects of epicatechin gallate (ECG) and kuraridin on cytokines production of human macrophages stimulated with (FIG. 4A) Peptidoglycan (PGN) and (FIG. 4B) Staphylococcal enterotoxin B (SEB)(n=6). Dexamethasone (Dex) at 1 µg/ml was used as positive control. PGN (0.1 µg/ml) or SEB (10 µg/ml) was used to stimulate the PBMC to produce cytokines. Kuraridin or ECG (2-64 µg/ml) was added to the cells and the cell supernatant was collected for cytokine assays. Significant results by comparing the drug treatment groups with the drug free control are indicated ($*p<0.05$; $p<0.01$; $*p<0.001$).
Figure 4A:
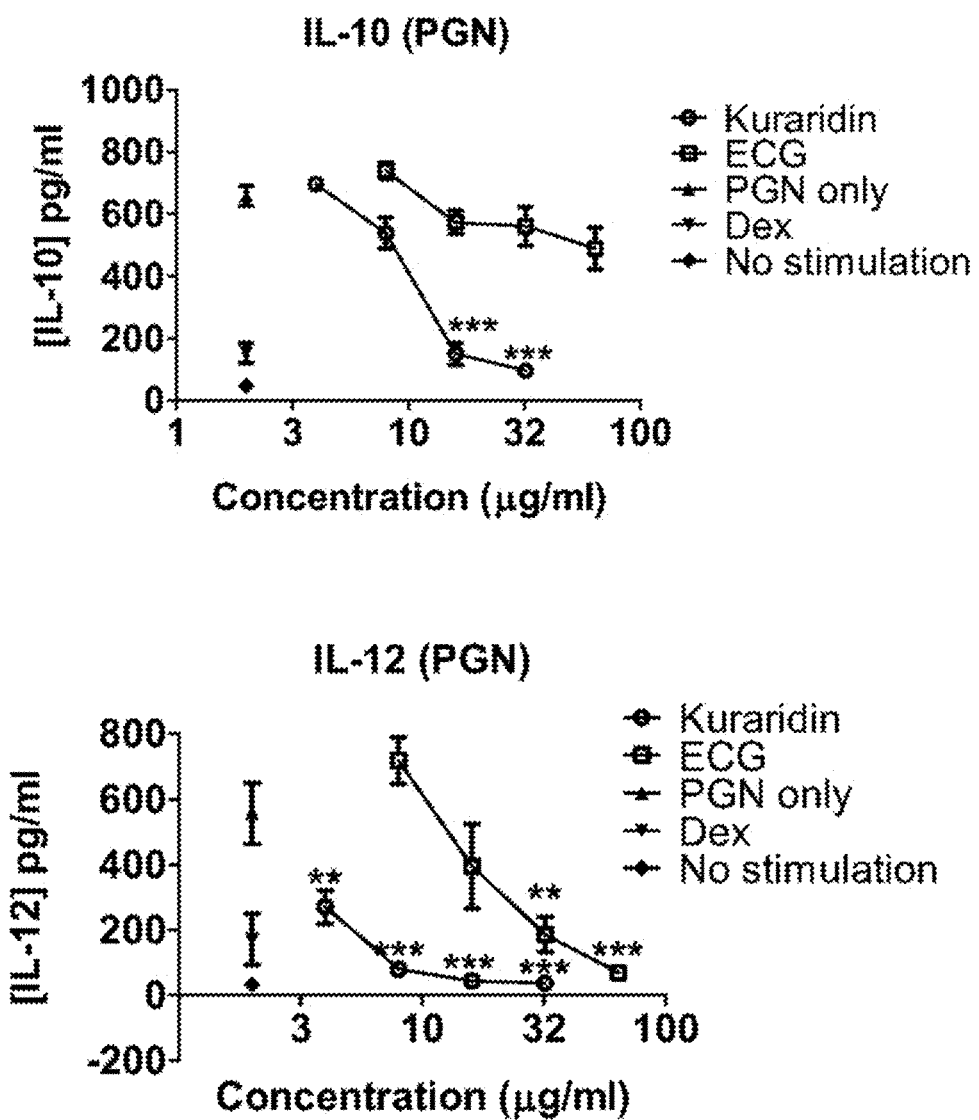
Figure 4B:
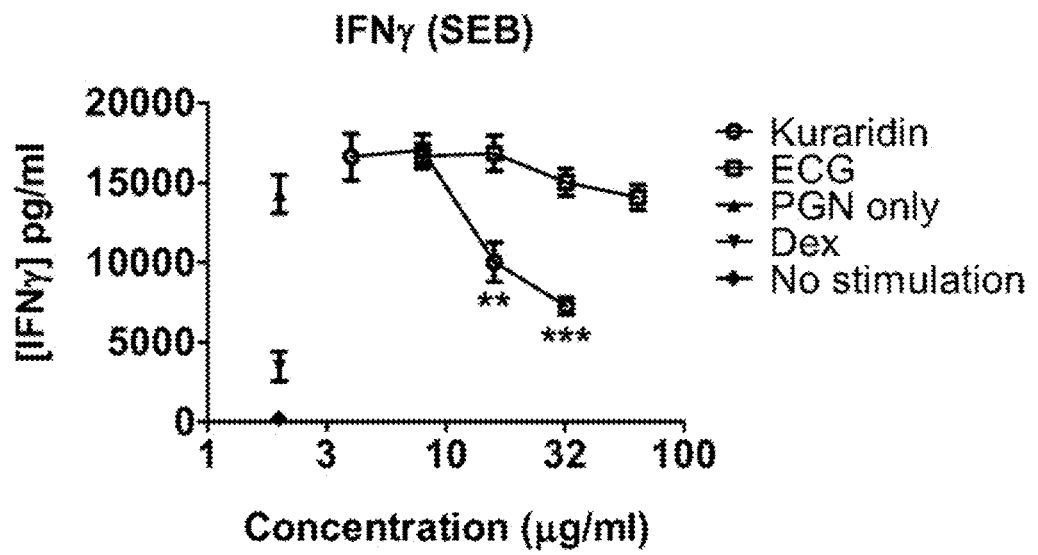
Figure 4B:
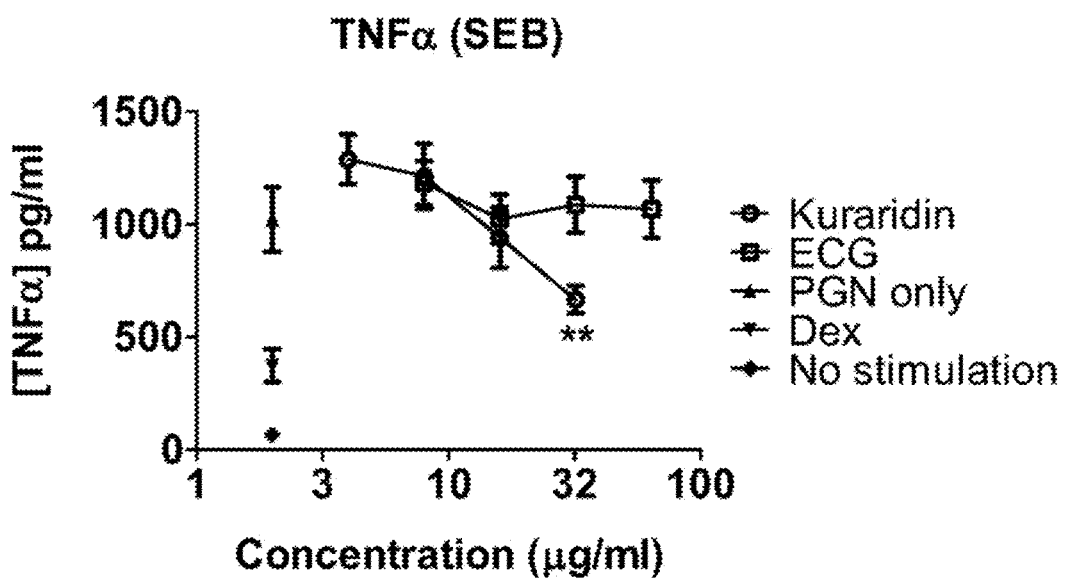
Figure 4B:
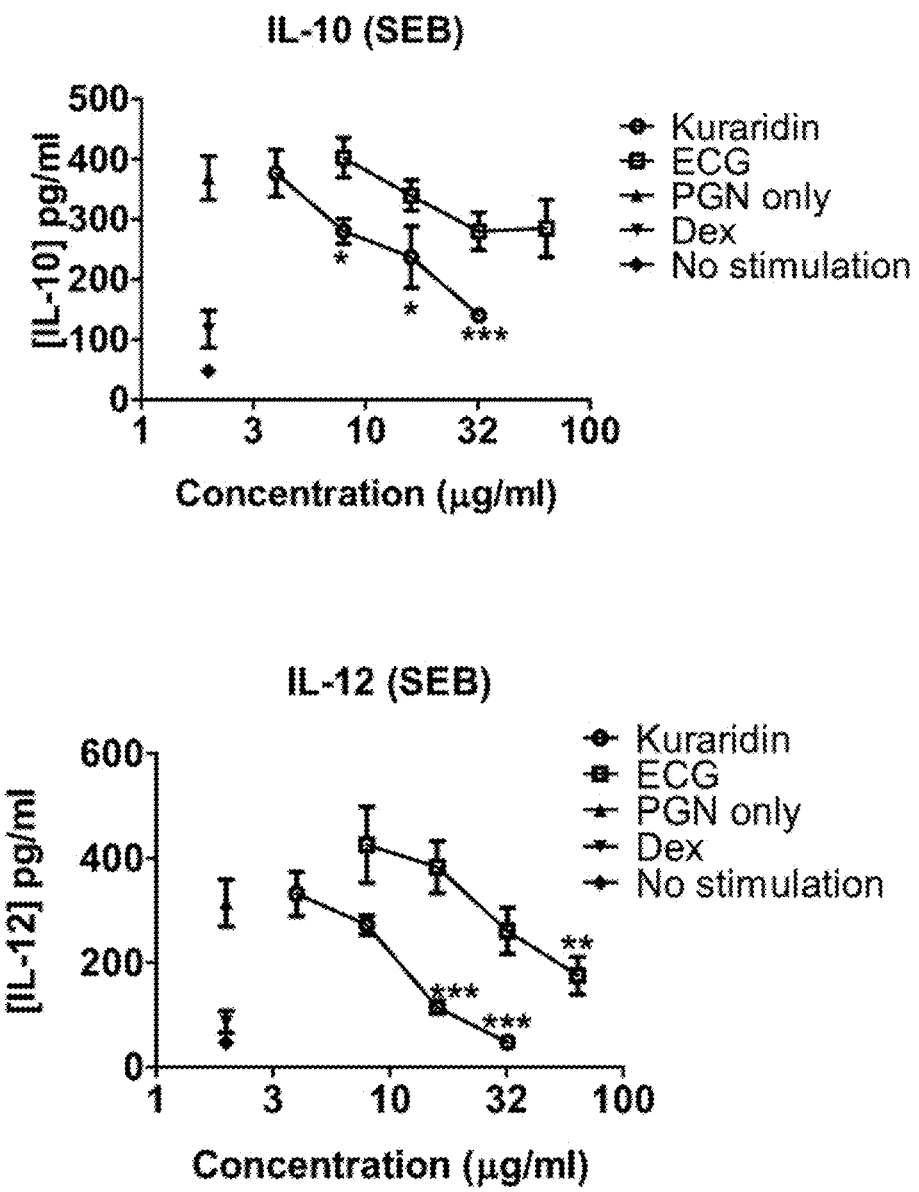
Figure 5A:
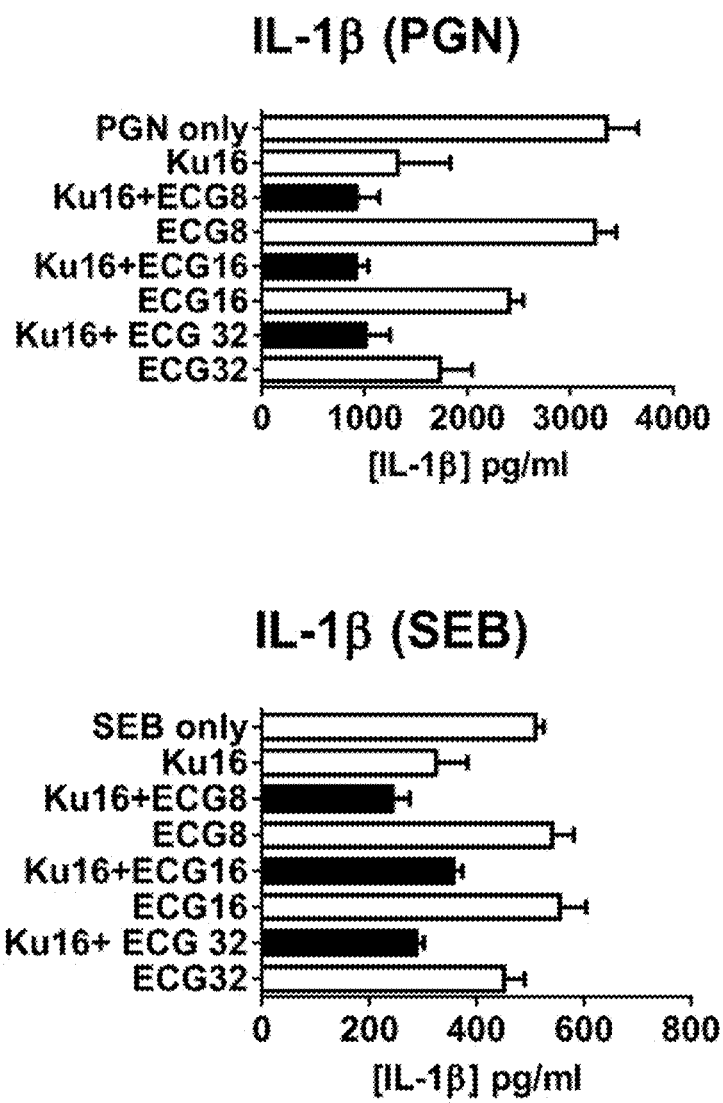
FIGS. 5A-5C Combined effects of epicatechin gallate (ECG) (8-32 µg/ml) and kuraridin (16 µg/ml) on cytokines production (FIG. 5A) IL-1β, (FIG. 5B) IL-6 and (FIG. 5C) TNFα from human peripheral blood mononuclear cells (PBMC) (n=4). Peptidoglycan (PGN) (0.1 µg/ml) or Staphylococcal enterotoxin B (SEB) (10 µg/ml) was used to stimulate the PBMC to produce cytokines. Kuraridin (Ku) or ECG alone or in combination was added to the cells for 24 h and the cell supernatant was collected for cytokine assays. Significant results by comparing the drug combination (ECG+Ku) groups with the kuraridin when used alone are indicated ($*p<0.05$; $p<0.01$; $*p<0.001$).
Figure 5B:
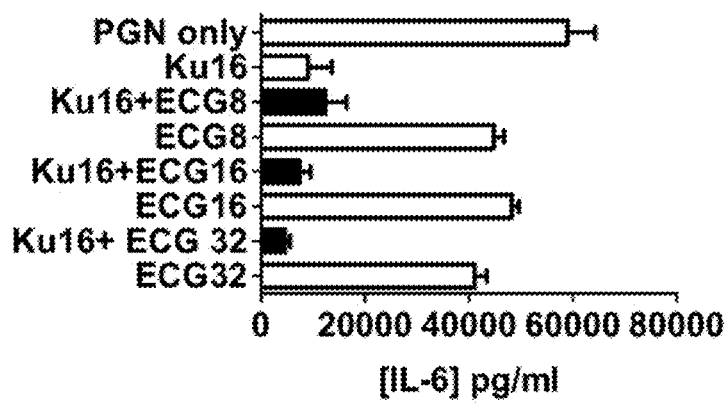
Figure 5B:
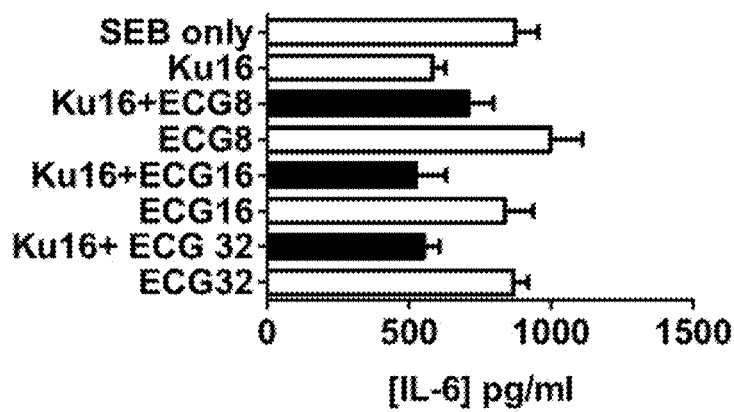
Figure 5C:
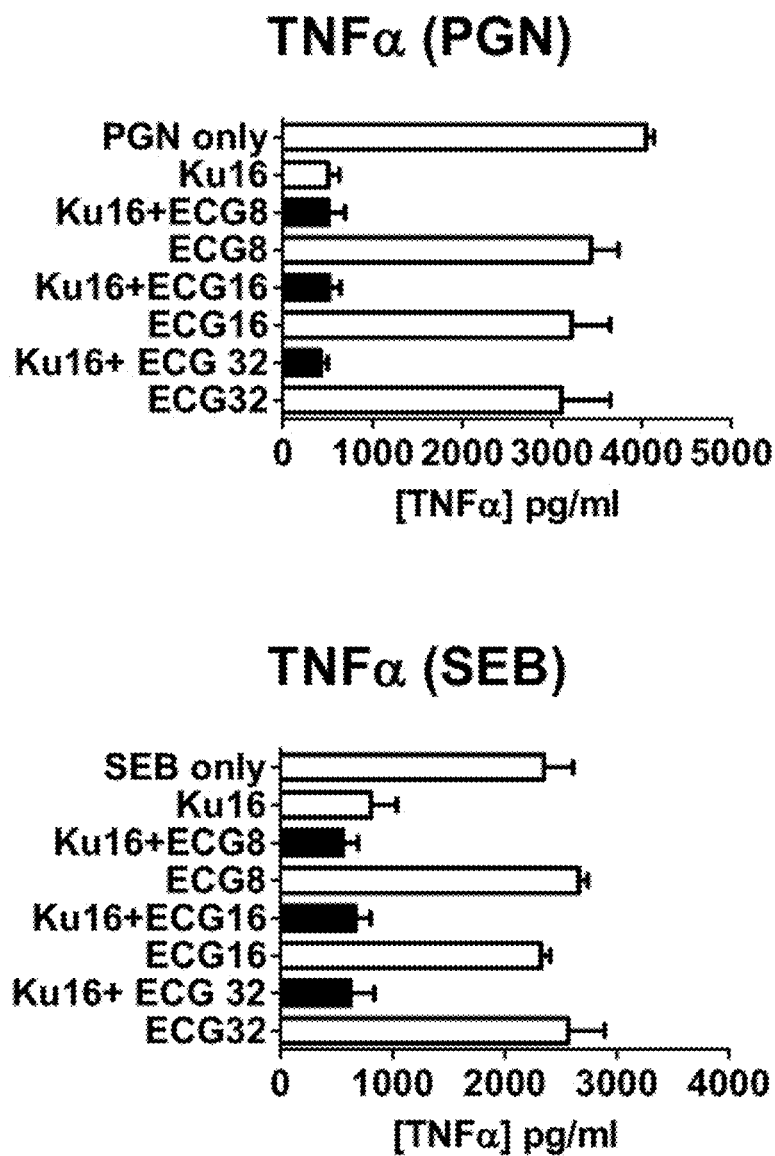
Figure 6A:
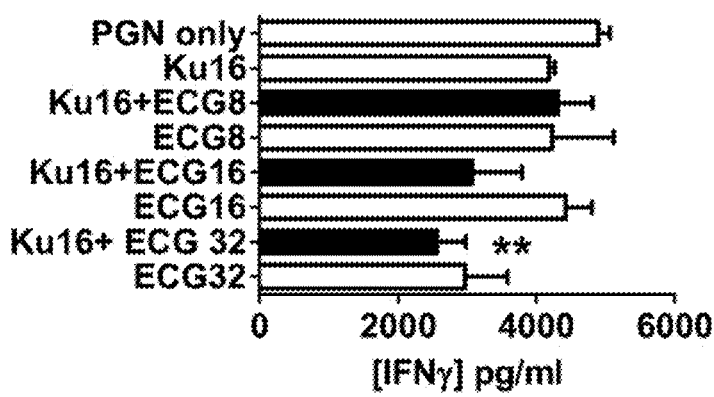
FIGS. 6A-6D Combined effects of epicatechin gallate (ECG) (8-32 µg/ml) and kuraridin (16 µg/ml) on (FIG. 6A) IFNγ, (FIG. 6B) TNFα, (FIG. 6C) IL-10 and (FIG. 6D) IL-12 production of human cultured macrophages (n=4). Peptidoglycan (PGN) (0.1 µg/ml) or Staphylococcal enterotoxin B (SEB) (10 µg/ml) was used to stimulate the PBMC to produce cytokines. Kuraridin (Ku) or ECG alone or in combination was added to the cells for 24 h and the cell supernatant was collected for cytokine assays. Significant results by comparing the drug combination (ECG+Ku) groups with the kuraridin when used alone are indicated ($*p<0.05$; $p<0.01$; $*p<0.001$).
Figure 6A:
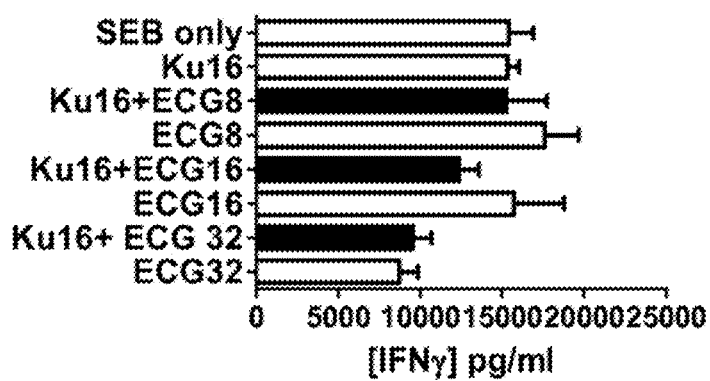
Figure 6B:
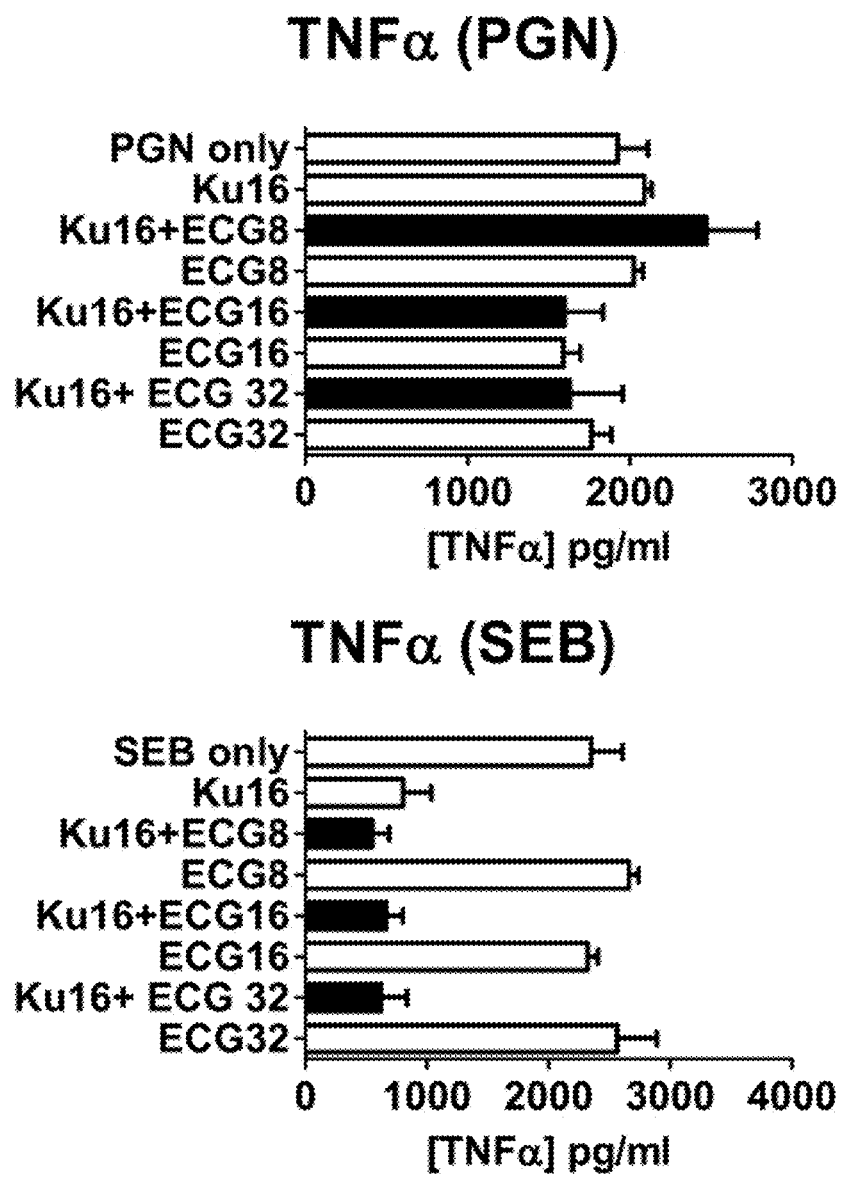
Figure 6C:
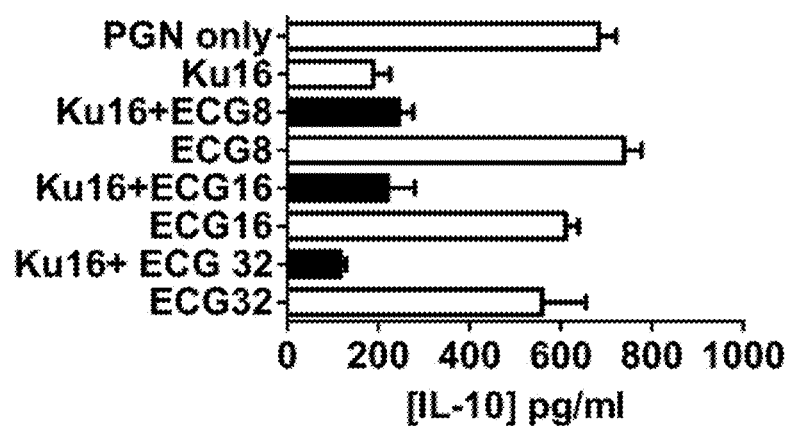
Figure 6C:
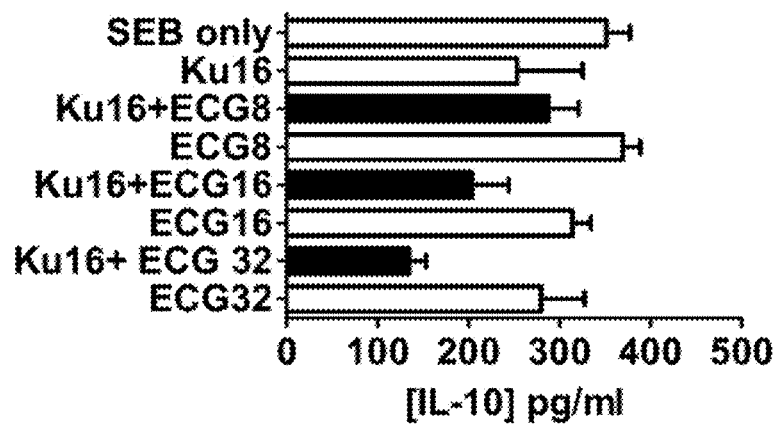
Figure 6D:
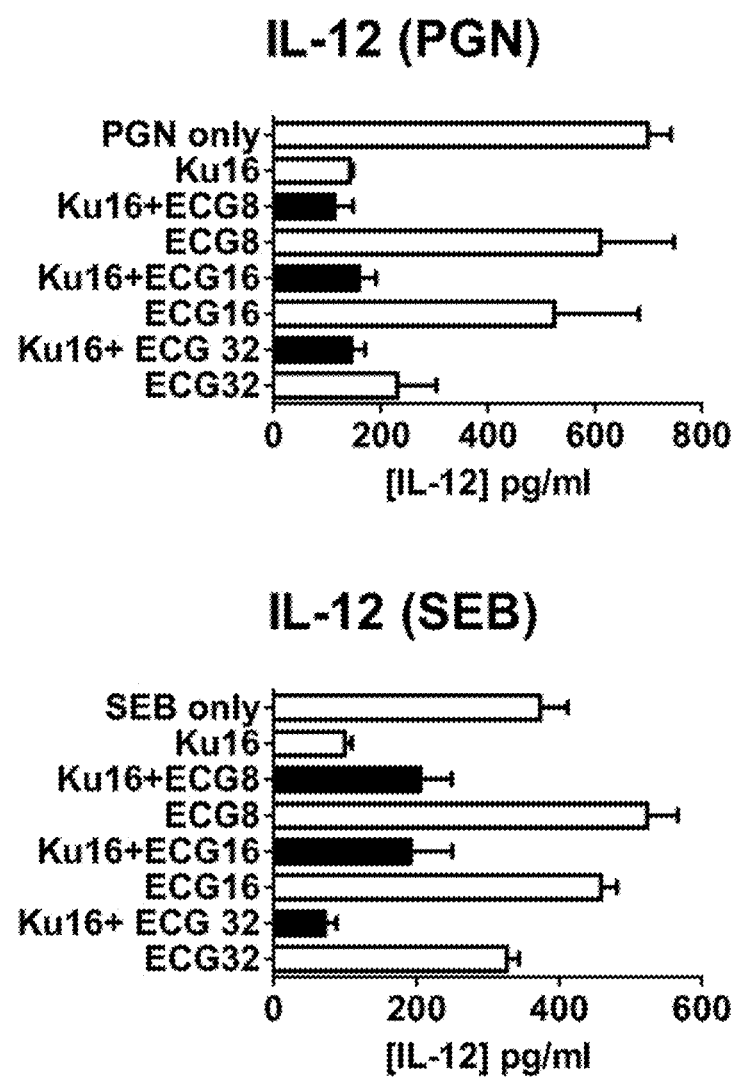

Kuraridin and ECG could Dose-Dependently Inhibit Inflammatory Cytokines Released from Peptidoglycan-Induced and Staphylococcal-Enterotoxin-B-Induced Human PBMC as Well as Macrophages Bacterial infections are usually associated with inflammatory cytokines production from immune cells. Hence, the effects of kuraridin and ECG on the production of IL-1β, IL-6 and TNF-α stimulated by *S. aureus* isolated peptidoglycan (PGN) and Staphylococcal enterotoxin B (SEB) were investigated. For PBMC stimulated with PGN and SEB (FIG. 3), kuraridin dose-dependently inhibited IL-10 and IL-12 production from 16-32 μg/ml. At 32 μg/ml, kuraridin suppressed TNF-α production from SEB-activated macrophages. ECG mildly suppressed IL-10 and IL-12 from 32-64 μg/ml, but had no significant effects on TNF-α. For macrophages (FIG. 4), kuraridin dose-dependently inhibited IL-6 and IL-12 production from 16-32 μg/ml, while ECG could suppress only IL-12 from 32-64 μg/ml. For IFN-γ productions, kuraridin could suppress both PGN and SEB activated macrophages at 32 mg/ml. In order to observe whether the combination of kuraridin and ECG could synergistically suppress the inflammatory cytokines or not, the combined effects of kuraridin (16 μg/ml) with ECG (16, 32 and 64 μg/ml) on PBMC and macrophages were studied (FIGS. 5-6). Compared with the compounds used alone, more potent suppressive effect was observed in IFN-γ production from PGN activated macrophages (FIG. 6) when kuraridin (16 μg/ml) and ECG (16 μg/ml) were used together.

Animal Studies—Mouse Pneumonia Model

Figures 7A, 7B:
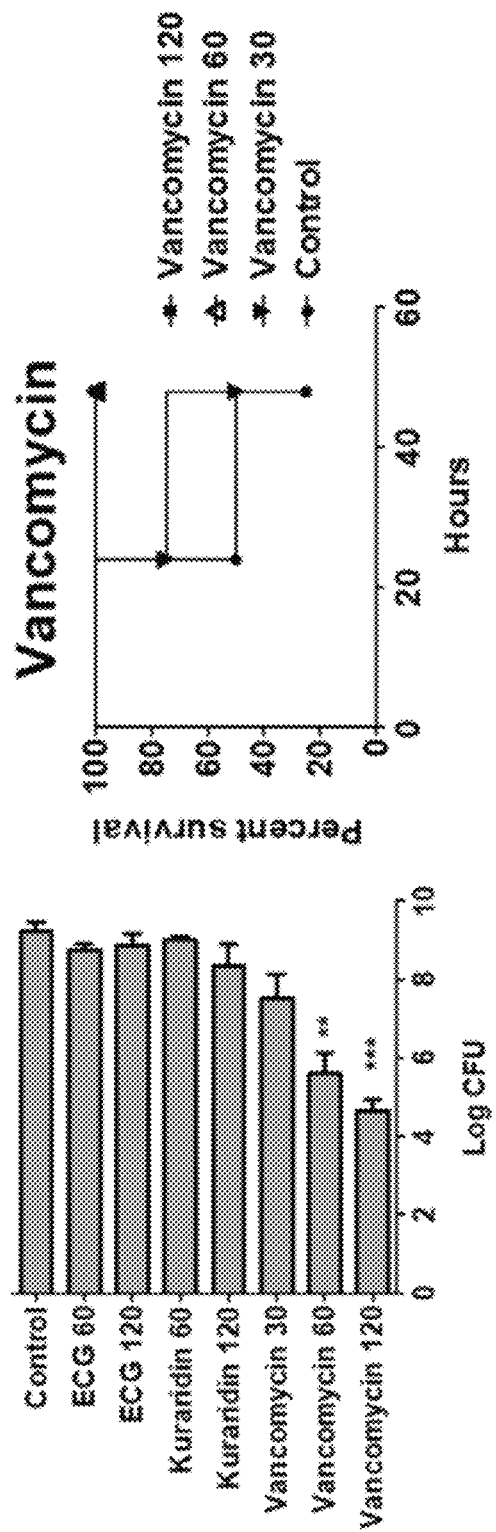
FIGS. 7A-7D Mice infected with ST30 ($3\times10^8$ colony forming unit (CFU)) with different monotherapy treatment options: ECG (60 and 120 mg/kg); kuraridin (60 and 120 mg/kg), vancomycin (30, 60 and 120 mg/kg) and control (ethanol in saline). Mice were sacrificed after 48 h.
Figures 7C, 7D:
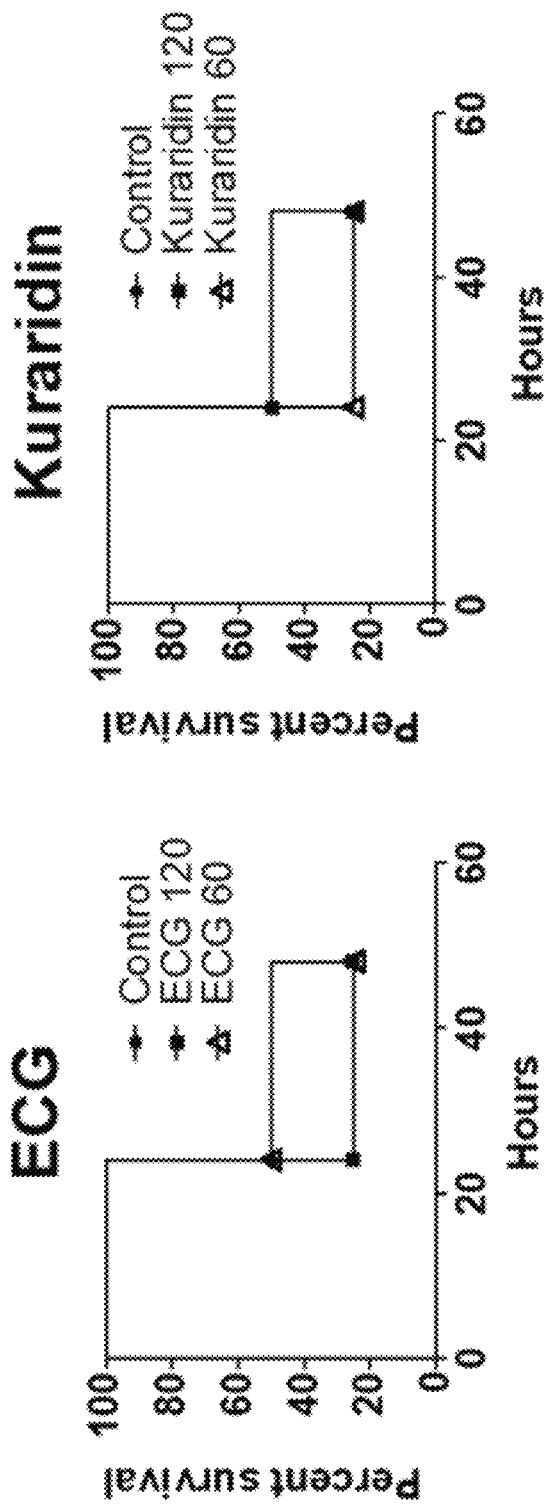

To confirm whether the combined effect of ECG and kuraridin could enhance vancomycin in vivo, a murine pneumonia model was used. Panton-Valentine leukocidin (PVL) positive CA-MRSA ST-30 infected mice (4 per therapy) were randomized to receive vancomycin, ECG or kuraridin (30, 60 or 120 mg/kg every 12 h twice daily for 2 days) as monotherapy to determine the sub-MIC dosage for the active ingredients/antibiotics combination synergistic studies. ECG and vancomycin are soluble in saline (20 mg/ml) and kuraridin is soluble in ethanol/saline solution (20 mg/ml). Mice in the control group received equivalent amount of ethanol/saline (0.1 ml) used in kuraridin. The inoculation dose of ST30 intranasally was $3\times10^8$ CFU and symptoms of severe illness such as lethargy, hunched posture, ruffled fur, and weight loss were observed after infections. Vancomycin (120 mg/kg), which is approximately equivalent to a human therapeutic dose and also at 60 mg/kg, could significantly reduce the log CFU counts (4.65±0.29 and 5.60±0.55 respectively), when compared with control group (9.20±025). The survival rate of vancomycin groups (120 and 60 mg/kg) were improved from 25% to 100%. On the other hand, ECG and kuraridin (60 and 120 mg/kg) when used alone, could not reduce the log CFU counts or improve the survival rates of the ST30 infected mice (FIG. 7). ECG and kuraridin (120 mg/kg) were then combined to see whether they could enhance the antibacterial activity of the sub-MIC dosage of vancomycin (60 mg/ml) in vivo.

Figure 8A:
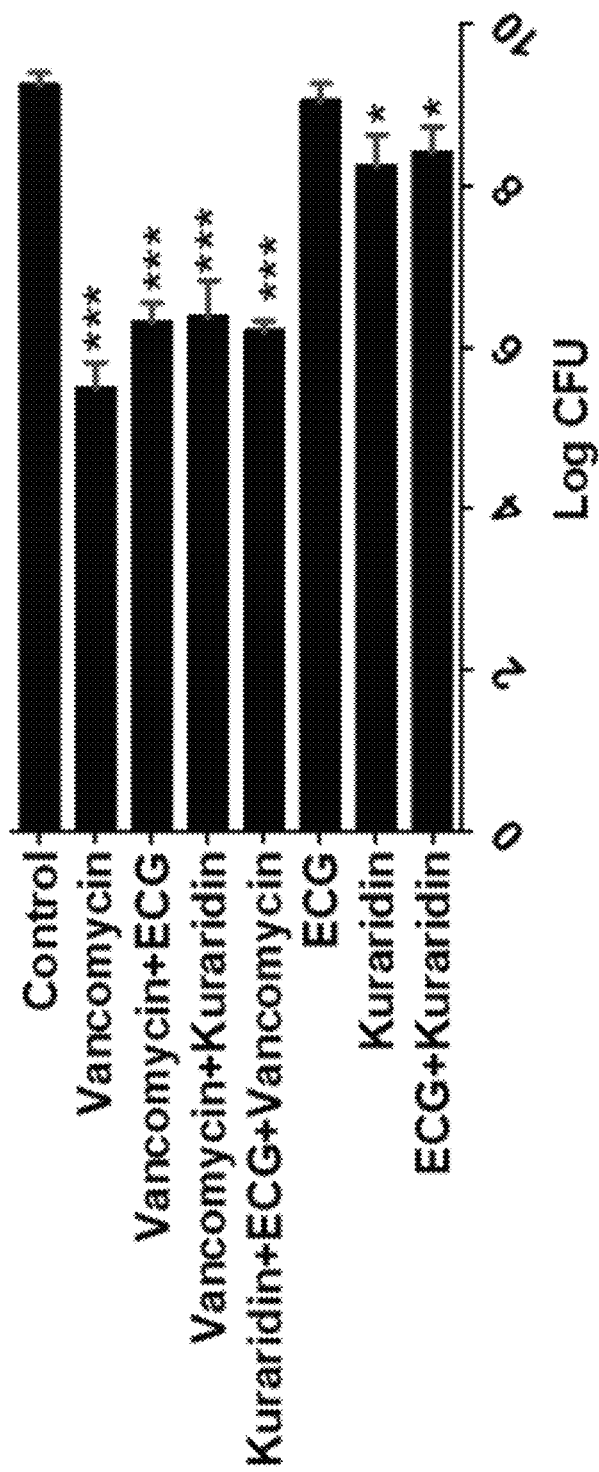
FIGS. 8A-8C Mice infected with ST30 ($3\times10^8$ colony forming unit (CFU)) with different treatment options: mice infected with ST30 (Control); infected mice treated with vancomycin (60 mg/kg), ECG (120 mg/kg) or kuraridin (120 mg/kg) alone; infected mice treated with ECG (120 mg/kg) and kuraridin (120 mg/kg); infected mice treated with ECG (120 mg/kg) and vancomycin (60 mg/kg); kuraridin (120 mg/kg) and vancomycin (60 mg/kg) and ECG (120 mg/kg), kuraridin (120 mg/kg) and vancomycin (60 mg/kg). Mice were sacrificed after 48 h.
Figure 8B:
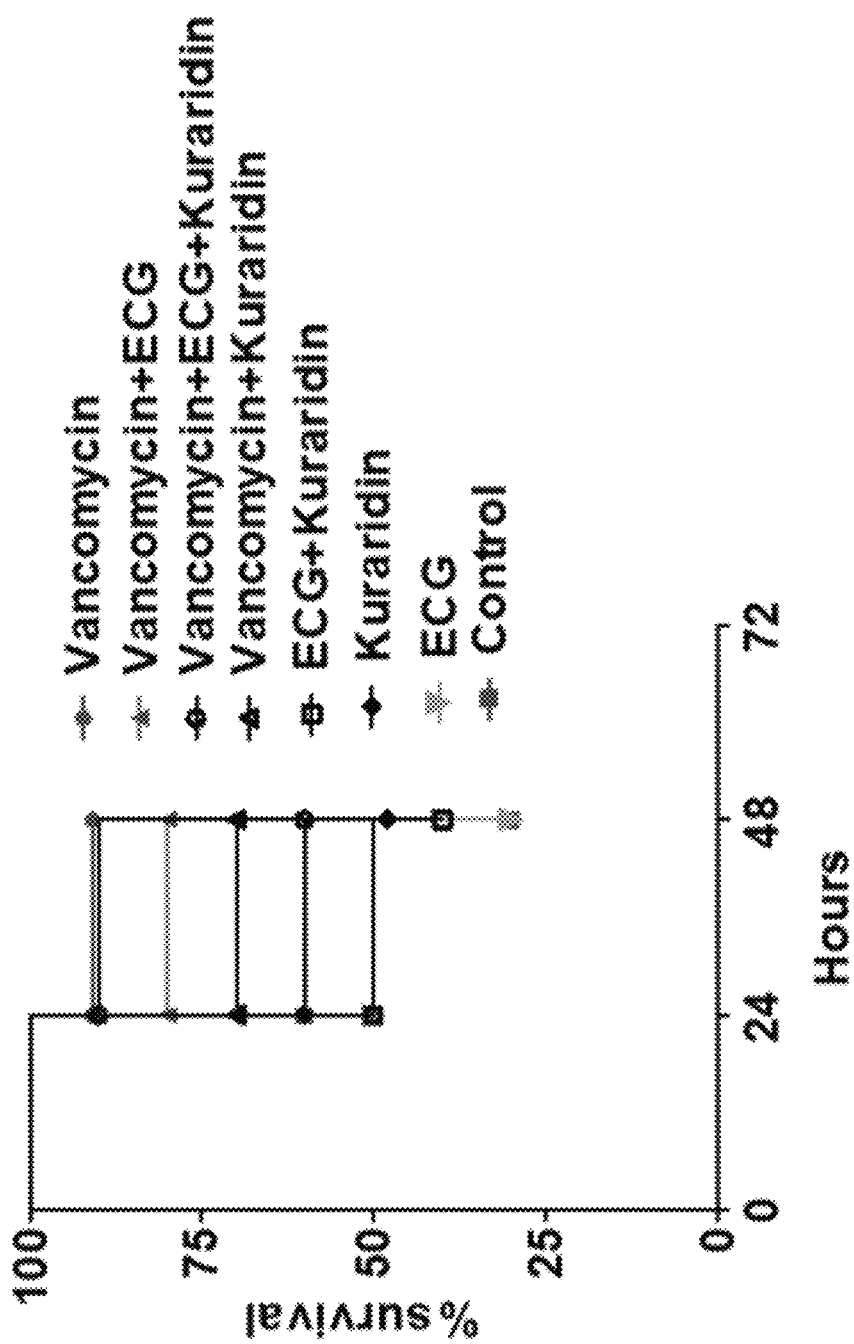
Figure 8C:
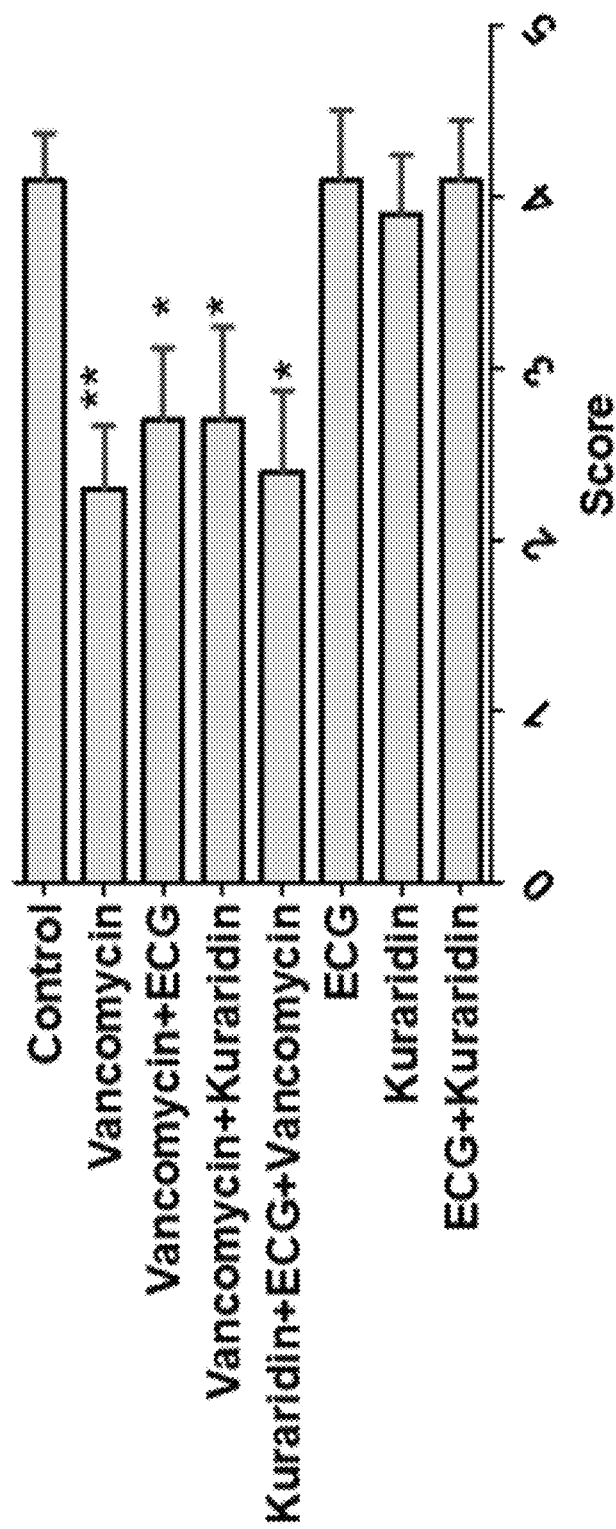
Figure 9:
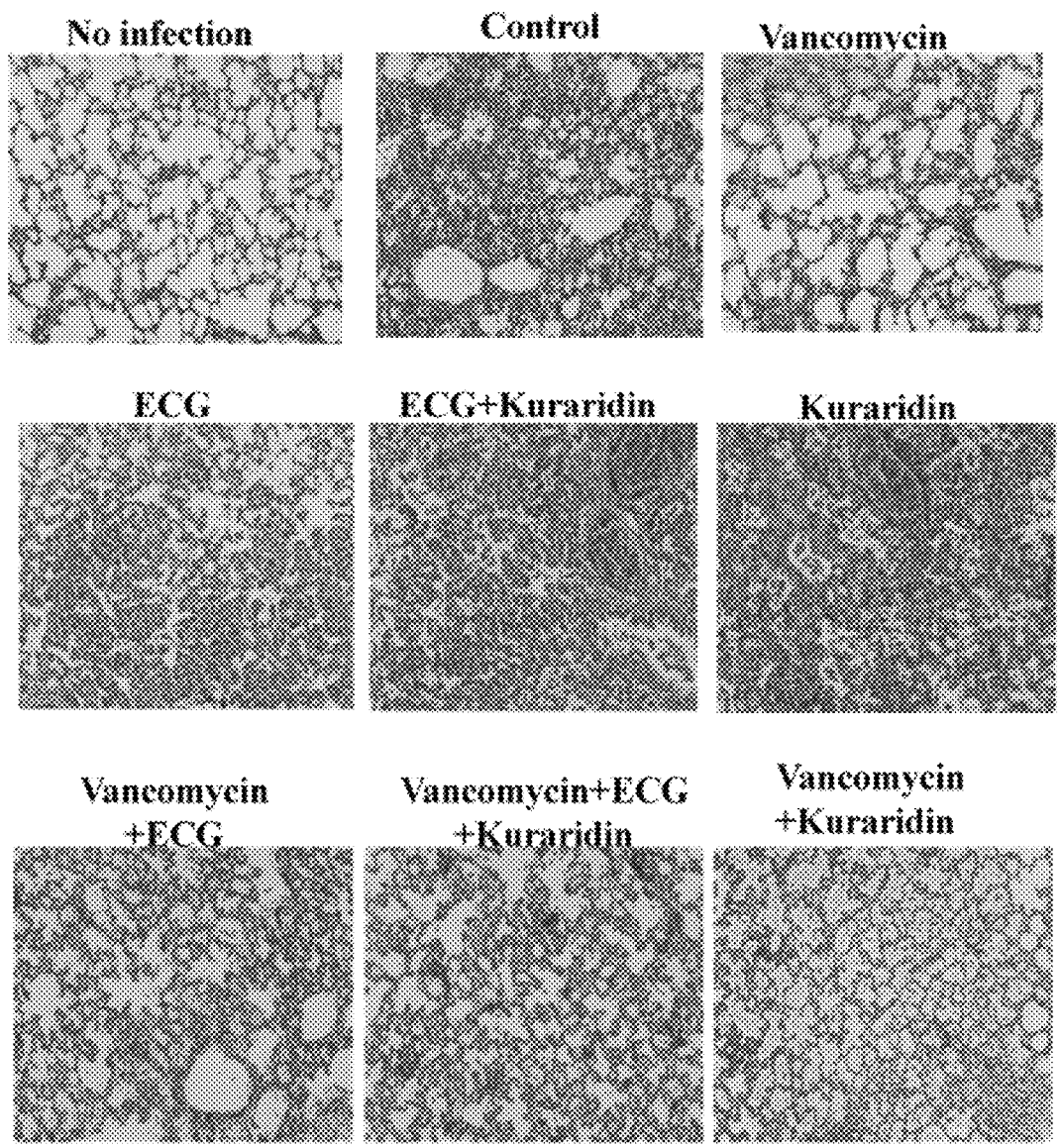
FIG. 9 Histology of lung tissue in normal mice without infection (No infection); mice infected with ST30 (Control); infected mice treated with vancomycin (60 mg/kg), ECG (120 mg/kg) or kuraridin (120 mg/kg) alone; infected mice treated with ECG (120 mg/kg) and kuraridin (120 mg/kg); infected mice treated with ECG (120 mg/kg) and vancomycin (60 mg/kg); kuraridin (120 mg/kg) and vancomycin (60 mg/kg) and ECG (120 mg/kg), kuraridin (120 mg/kg) and vancomycin (60 mg/kg).
Figure 10A:
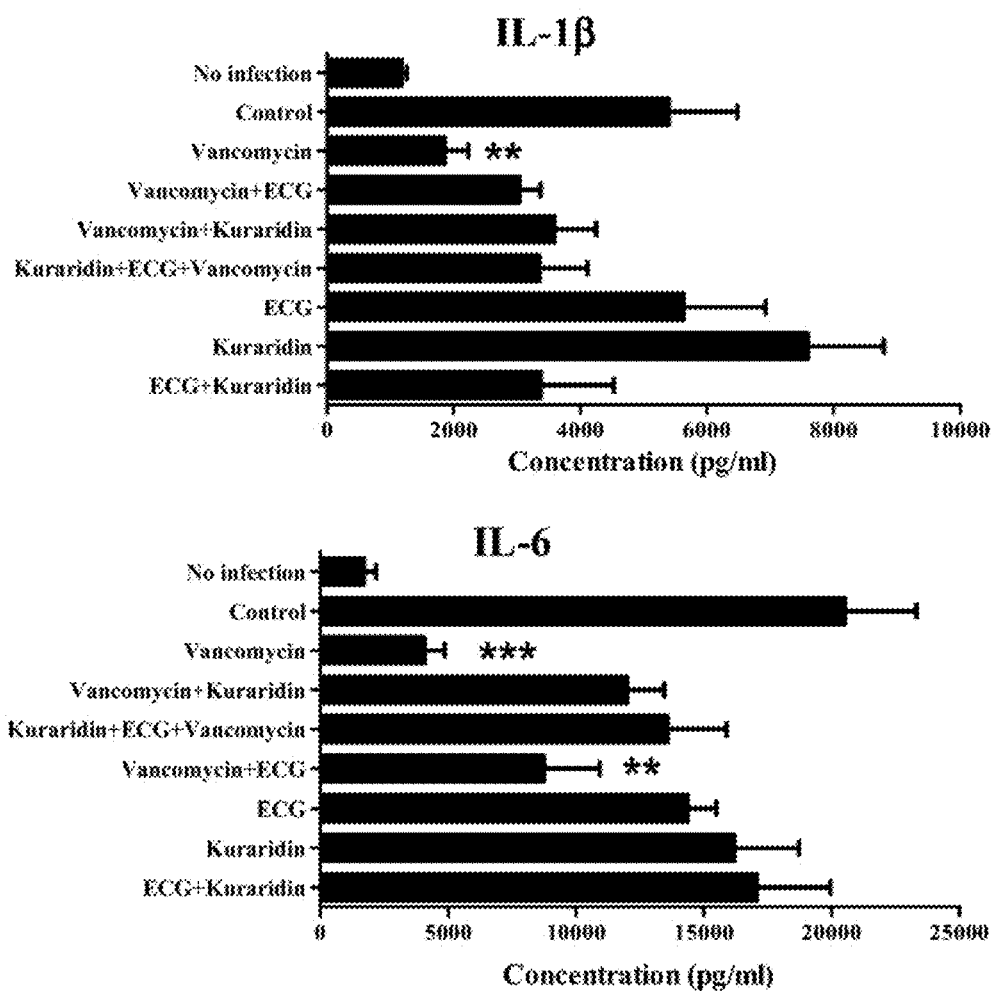
FIGS. 10A-10B The expressions levels of TNF-α, IFN-γ, IL-1β, IL-6 and IL-10 of the mice infected with ST30 from (FIG. 10A) lung homogenate (n=10) and (FIG. 10B) serum (n=3-10). Significant results by comparing the drug treatment groups with the drug free control are indicated ($*p<0.05$; $p<0.01$; $*p<0.001$).
Figure 10A:
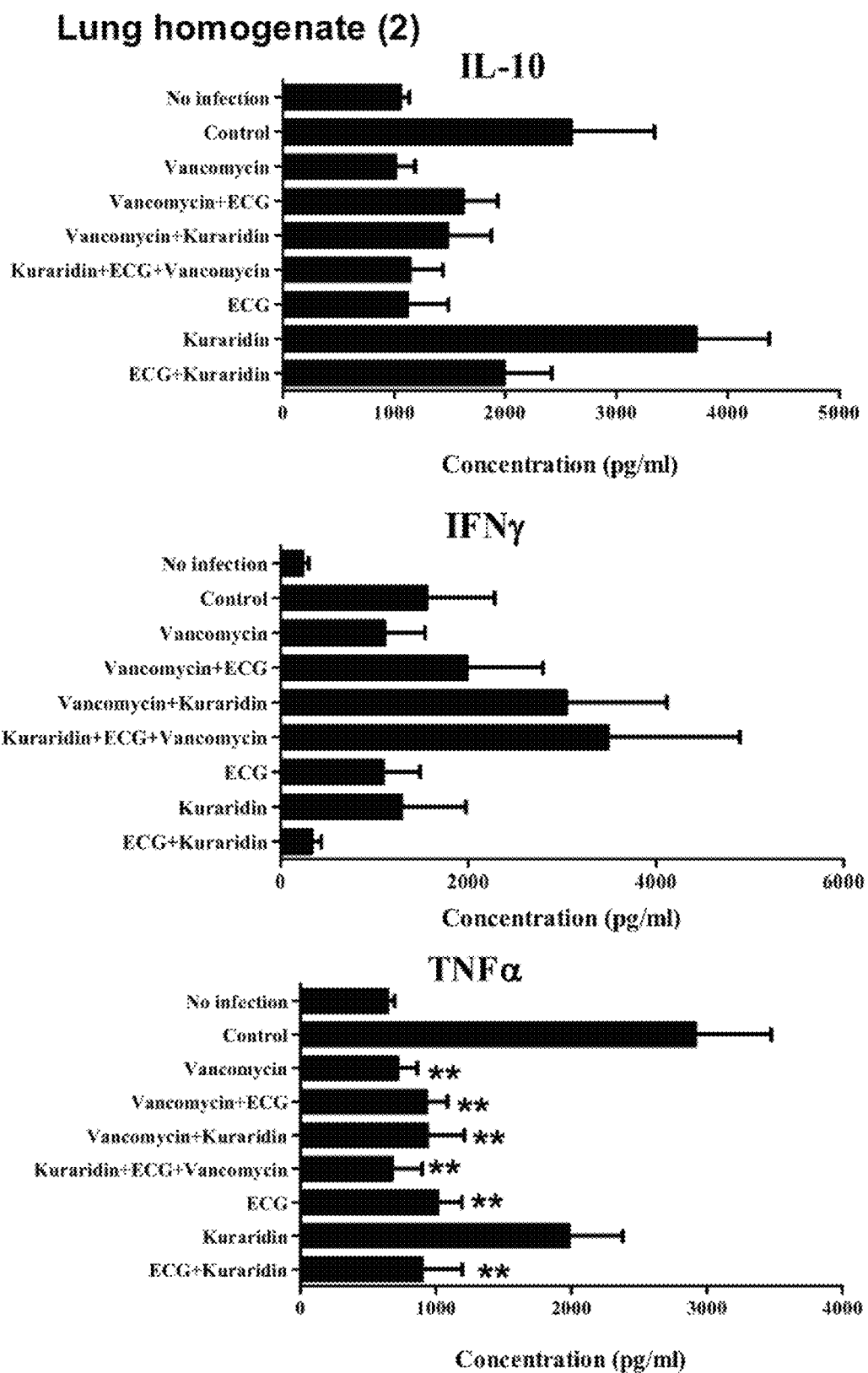
Figure 10B:
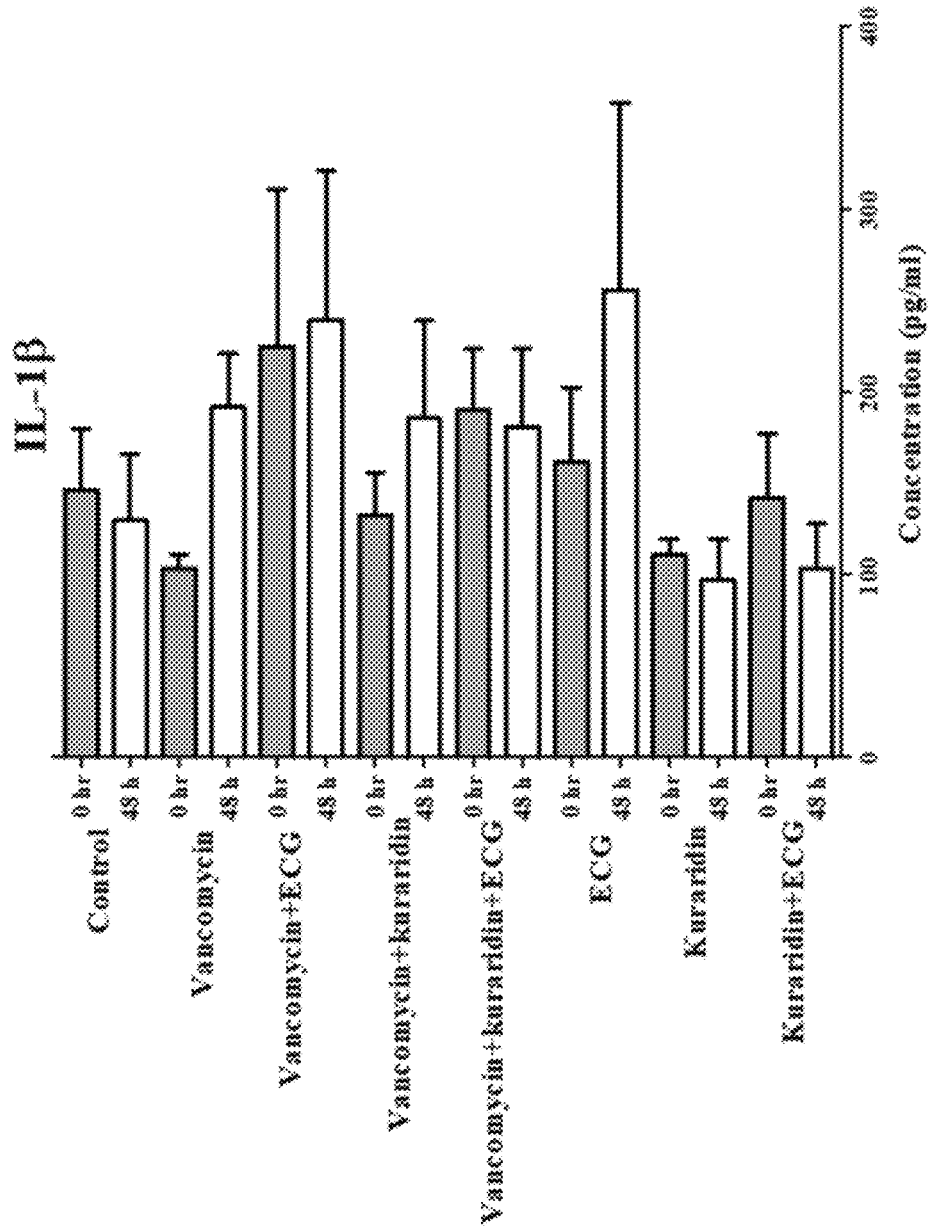
Figure 10B:
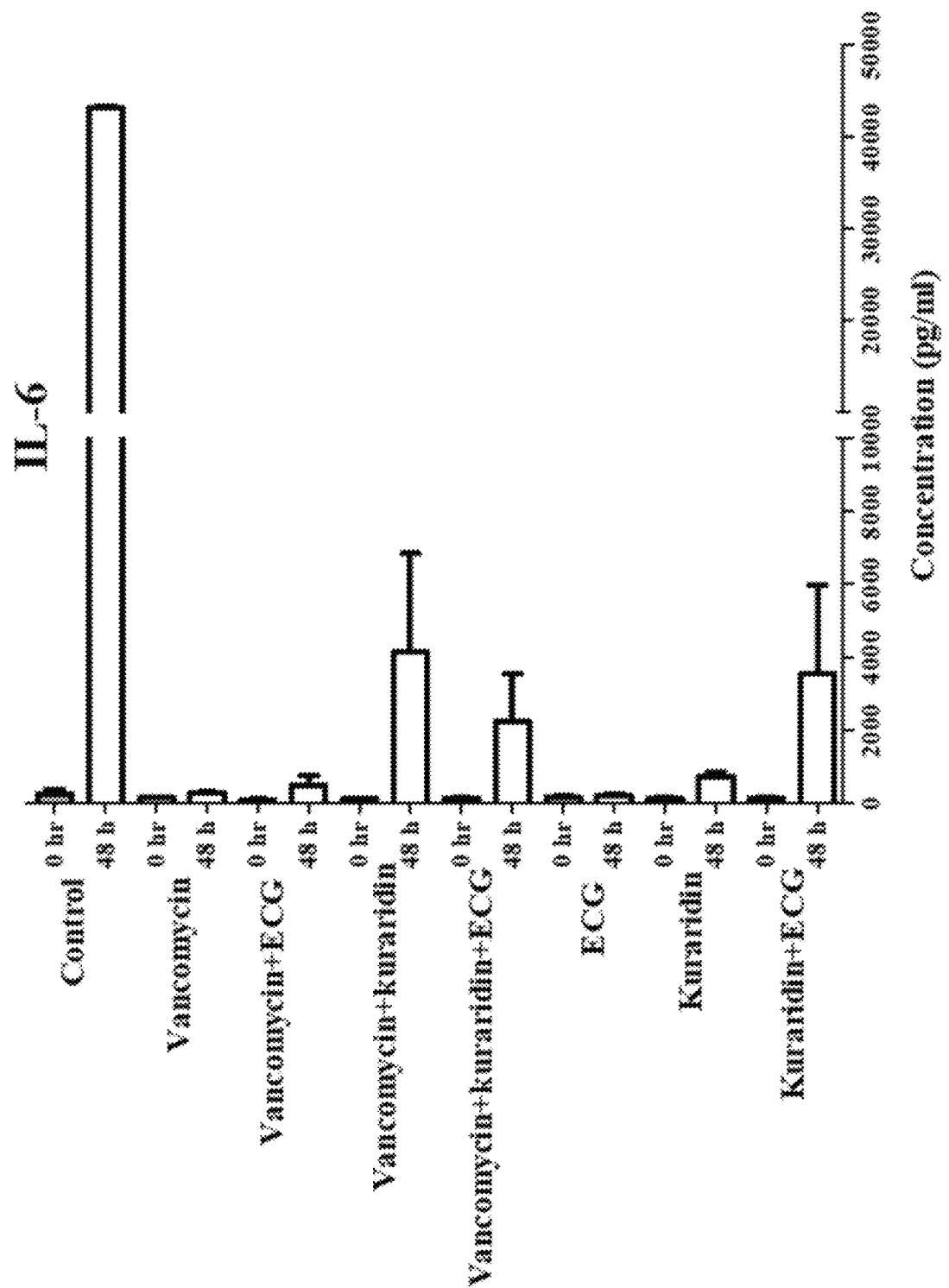
Figure 10B:
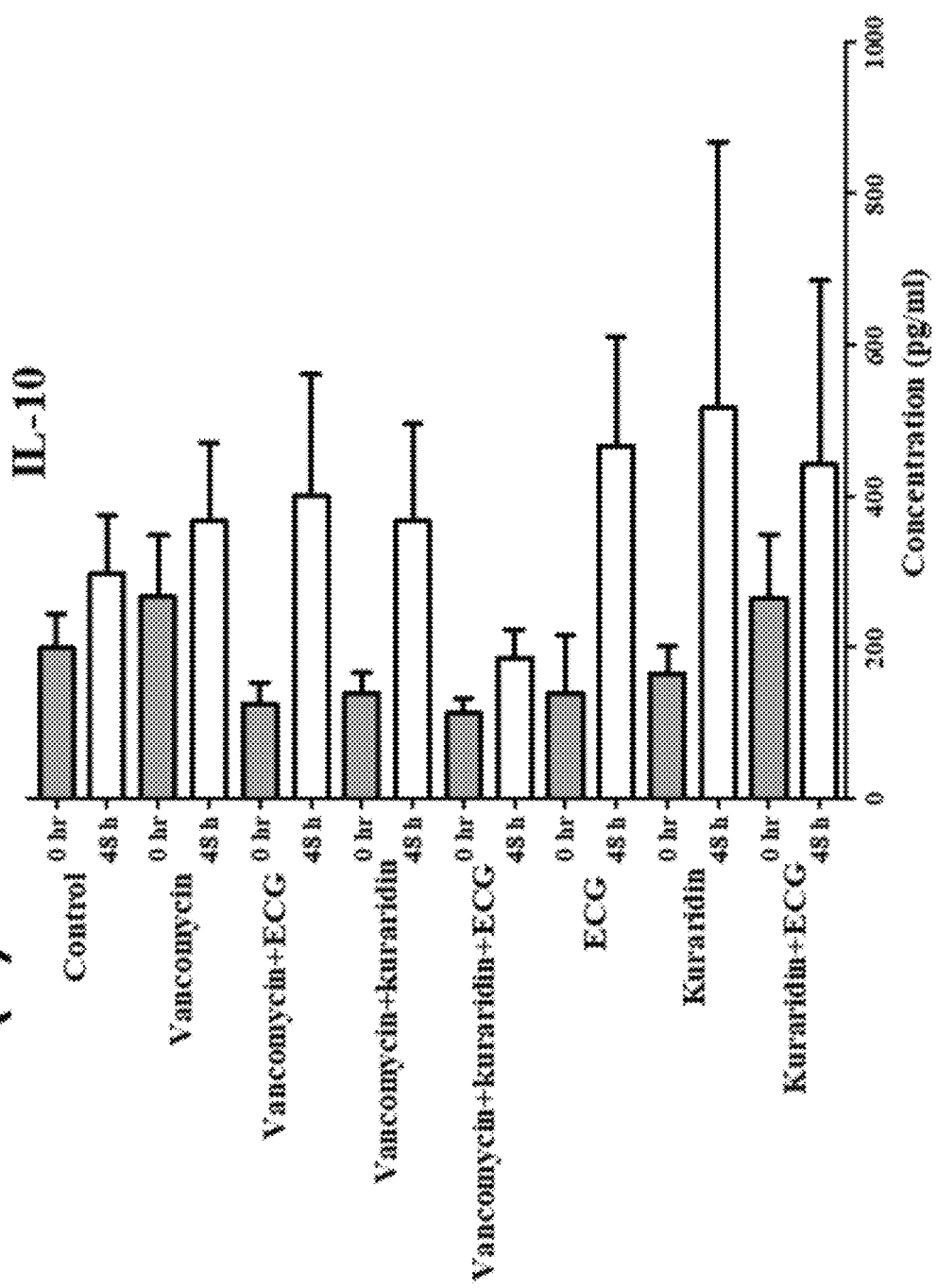
Figure 10B:
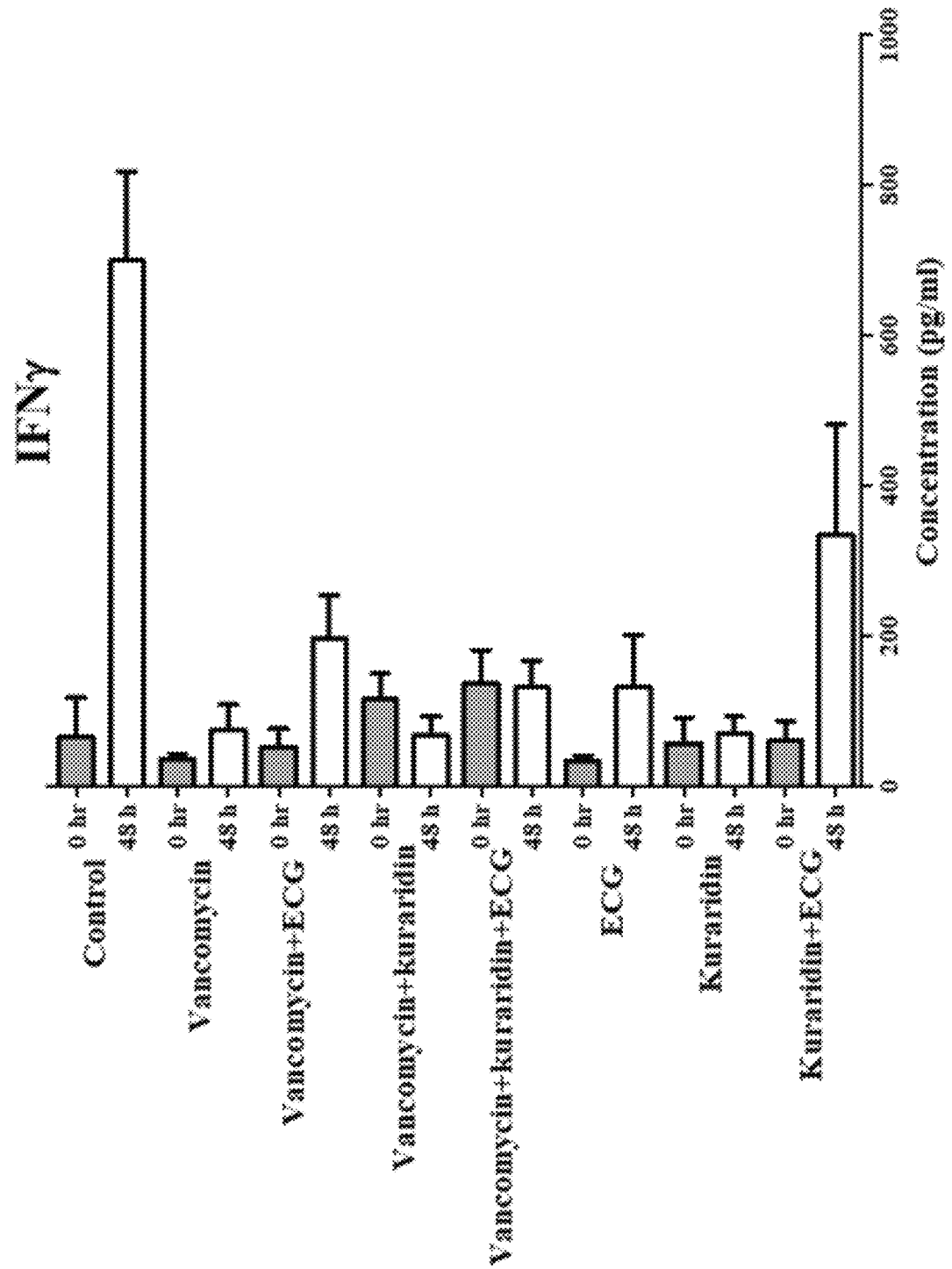
Figure 10B:
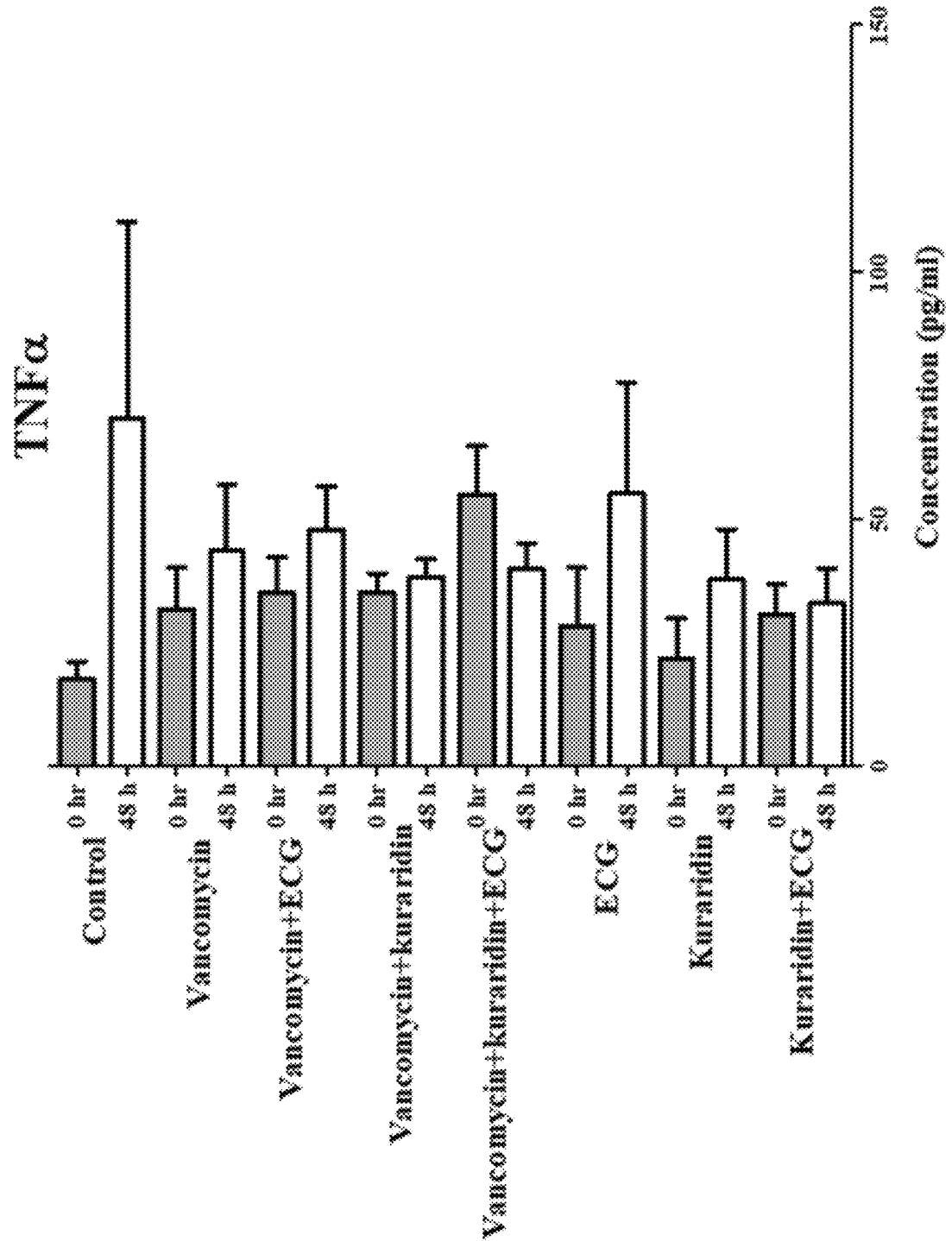

When kuraridin were used alone and combined with ECG, they could slightly reduce the log CFU counts (8.25±0.39 and 8.41±0.33, respectively) when compared with the control group (9.24±0.15)[FIG. 8(*a*)]. The survival rates of kuraridin alone and kuraridin with ECG (50% and 60%, respectively) were also improved when compared with the control group (30%). The effect of vancomycin alone on ST30 infected mice was compared with different combination of drugs (ECG+vancomycin, kuraridin+vancomycin, and ECG+kuraridin+vancomycin), but the efficacy of vancomycin could not be further enhanced with similar bacterial counts and survival rates [FIG. 8(*b*)]. The pneumonia scores of the lung histology were summarized in FIG. 8(*c*). Tissue sections from lungs infected with ST30 revealed a recruitment of leukocytes, inflammation in the lung parenchyma, bronchial epithelial damage and tissue necrosis (FIG. 9). The tissue profiles of the treatment groups (vancomycin alone, ECG+vancomycin, kuraridin+vancomycin, and ECG+kuraridin+vancomycin) were with fewer lesions, infiltration of leukocytes and erythrocytes in the airspace and the alveolar structure were preserved when compared with the control group.

For immunomodulation assessment of using ST30, the homogenates from the left lungs and the mice sera obtained were used. The cytokines levels from the sera and lung homogenates reflected the systemic and local inflammation status of the animals. The expression levels of TNF-α, IFN-γ, IL-1β, IL-6 and IL-10 on different treatment groups were summarized in FIG. 10. For the mice treated with vancomycin, the expression levels of TNFα, IL-1β, and IL-6 from lung homogenates were significantly lowered than the control group. Suppression of TNF-α were observed in most of the homogenates of the treatment groups except the group treated with kuraridin alone. No significant changes were observed in IFN-γ and IL-10 expressions. Suppressions of IL-6 observed in the sera were observed in all treatment groups when compared with the control.

For infecting mice with the clinical MRSA ST239 and the standard methicillin sensitive *Staphylococcus aureus* ATCC25923, $1\times10^9$ CFU could not induce any significant infection to mice with very low bacteria counts from lungs after 48 h. To enhance their virulence to mice and suppress the immunity (neutrophils and other immune cells) of the mice against bacterial infection, it is essential to induce the mice with neutropenia prior to the infection using an immunosuppressive agent cyclophosphamide. After inducing the neutropenia to the mice, $1\times10^7$ CFU of both bacteria strains could induce pneumonia to mice for drug testing.

Figure 11A:
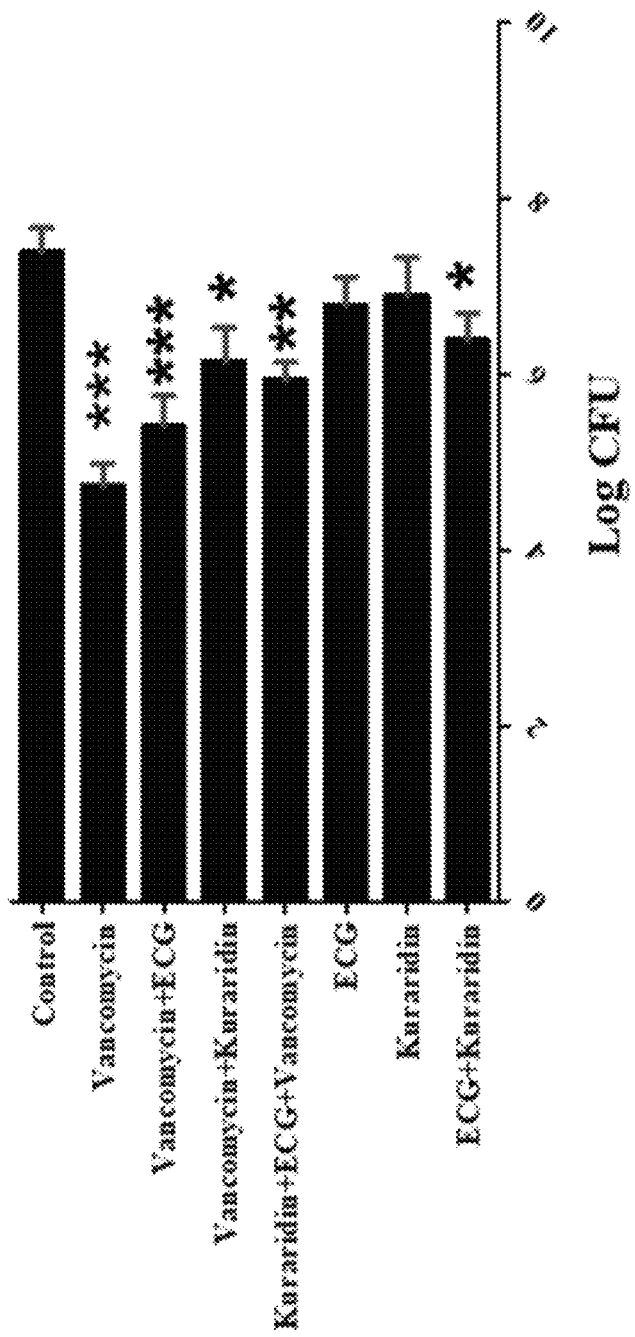
FIGS. 11A-11C Mice infected with ST239 ($3\times10^8$ colony forming unit (CFU)) with different treatment options: mice infected with ST239 (Control); infected mice treated with vancomycin (60 mg/kg), ECG (120 mg/kg) or kuraridin (120 mg/kg) alone; infected mice treated with ECG (120 mg/kg) and kuraridin (120 mg/kg); infected mice treated with ECG (120 mg/kg) and vancomycin (60 mg/kg); kuraridin (120 mg/kg) and vancomycin (60 mg/kg) and ECG (120 mg/kg), kuraridin (120 mg/kg) and vancomycin (60 mg/kg). Mice were sacrificed after 48 h. (a) The bacteria counts in Log CFU recovered from the left lungs; (b) the survival rates of each treatment group and (c) the pneumonia scores of the right lung histology. Significant results by comparing the drug treatment groups with the drug free control are indicated ($*p<0.05$; $p<0.01$; $*p<0.001$).
Figure 11B:
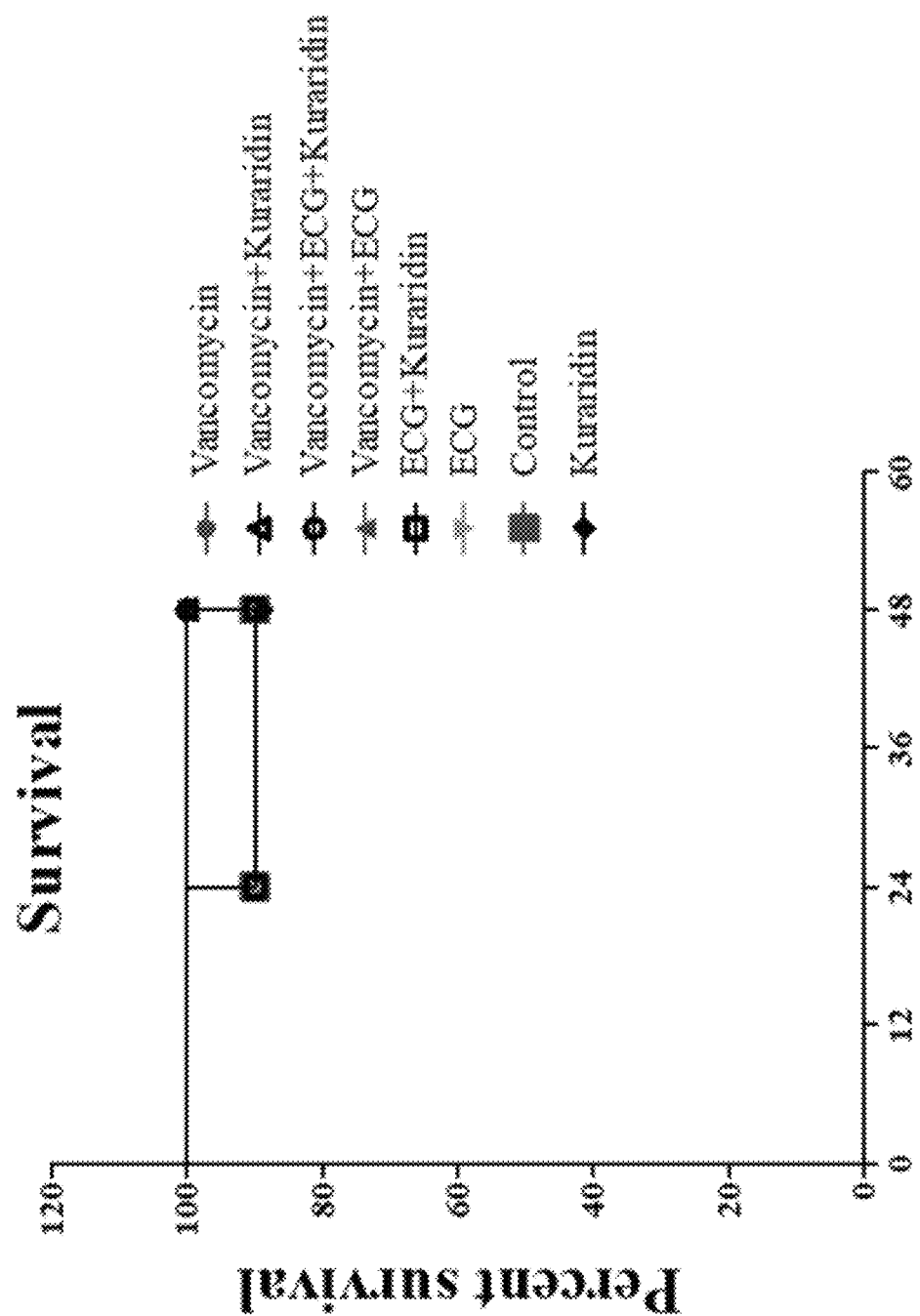
Figure 11C:
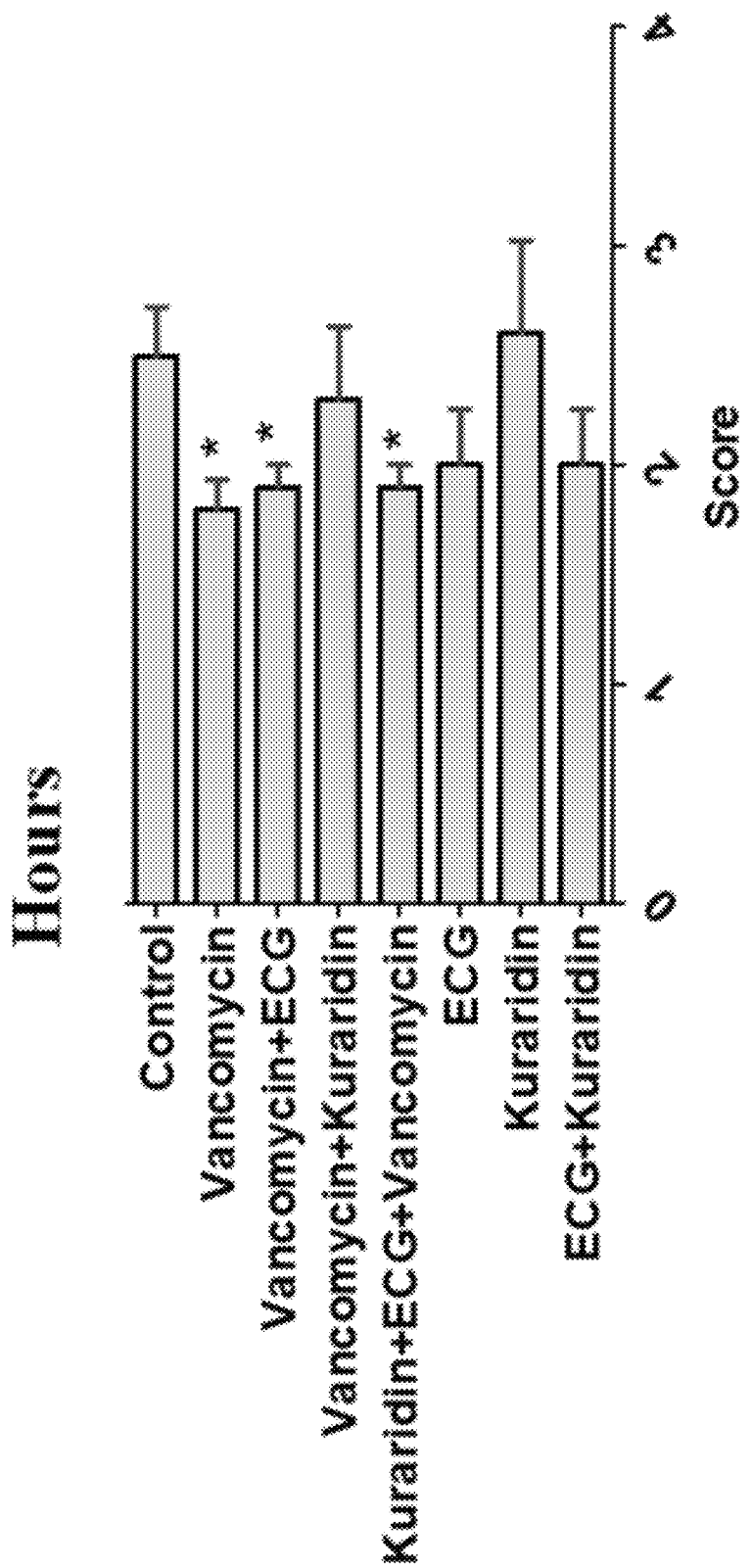
Figure 12:
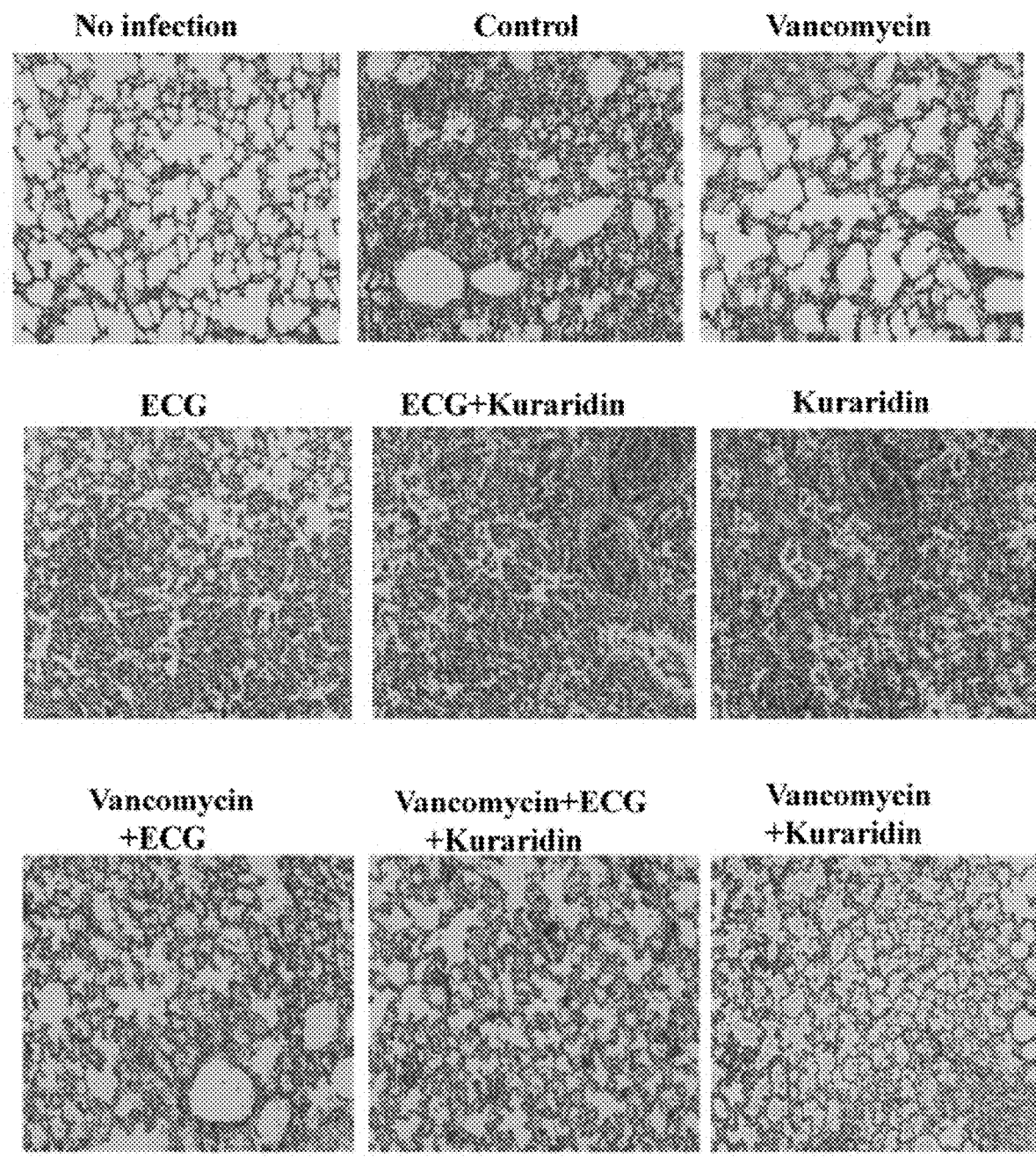
FIG. 12 Histology of lung tissue in normal mice without infection (No infection); mice infected with ST239 (Control); infected mice treated with vancomycin (60 mg/kg), ECG (120 mg/kg) or kuraridin (120 mg/kg) alone; infected mice treated with ECG (120 mg/kg) and kuraridin (120 mg/kg); infected mice treated with ECG (120 mg/kg) and vancomycin (60 mg/kg); kuraridin (120 mg/kg) and vancomycin (60 mg/kg) and ECG (120 mg/kg), kuraridin (120 mg/kg) and vancomycin (60 mg/kg).

For mice infected with the clinical MRSA strain: ST239, the results were summarized in FIGS. 11 and 12. For mice treated with vancomycin, significant reduction of the mean bacteria counts to 4.73±0.26 log CFU was observed when compared with the control (7.39±0.27 log CFU) [FIG. 11(*a*)]. Combinations of ECG and kuraridin could not enhance the antibacterial activities of vancomycin. Slight reduction of bacteria counts was observed in the group treated with ECG and kuraridin (6.40±0.30). The survival rates of all groups are similar and 1 mouse died in the control group, the groups treated with ECG alone, kuraridin alone and ECG+kuraridin [FIG. 11(*b*)]. Improvement in pneumonia score [FIG. 11(*c*)] were observed in the treatment groups with vancomycin (alone or combined other tested drugs). The tissue profiles of those groups were with fewer lesions, infiltration of leukocytes and erythrocytes in the airspace and the alveolar structure were preserved when compared with the control group (FIG. 12).

Figure 13A:
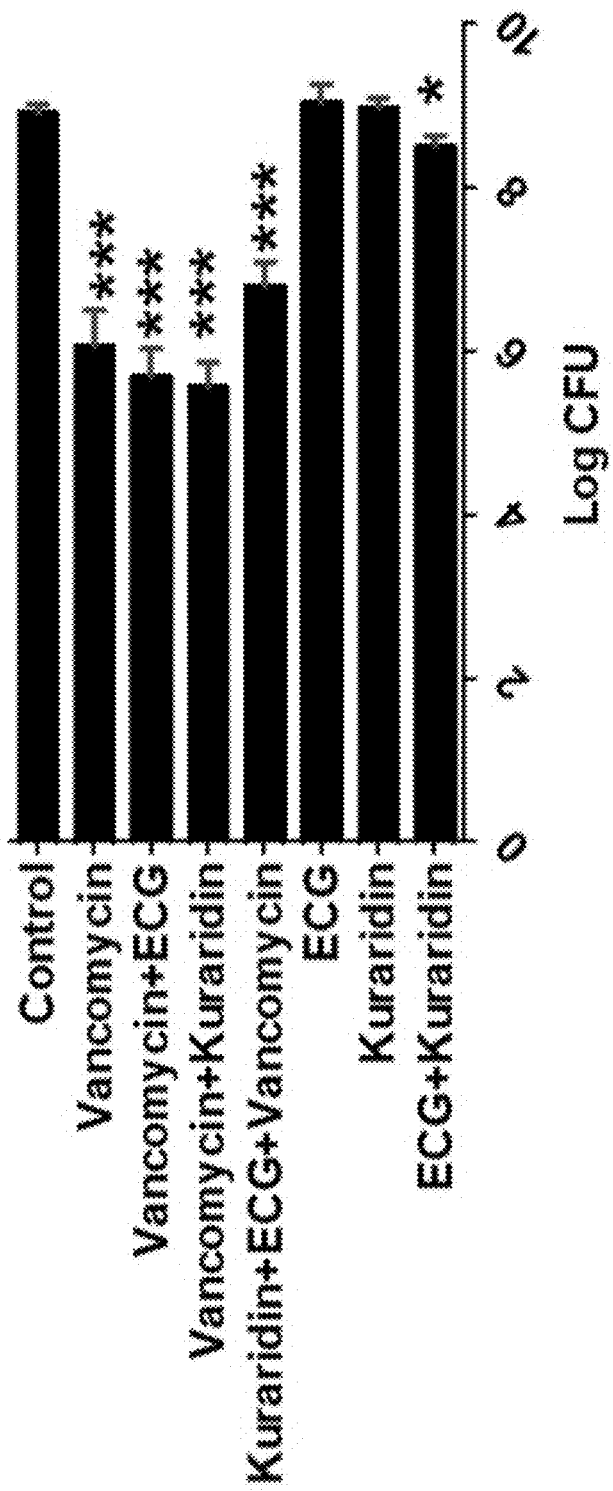
FIGS. 13A-13C Mice infected with ATCC25923 ($3 \times 10^8$ colony forming unit (CFU)) with different treatment options: mice infected with ATCC25923 (Control); infected mice treated with vancomycin (60 mg/kg), ECG (120 mg/kg) or kuraridin (120 mg/kg) alone; infected mice treated with ECG (120 mg/kg) and kuraridin (120 mg/kg); infected mice treated with ECG (120 mg/kg) and vancomycin (60 mg/kg); kuraridin (120 mg/kg) and vancomycin (60 mg/kg) and ECG (120 mg/kg), kuraridin (120 mg/kg) and vancomycin (60 mg/kg). Mice were sacrificed after 48 h.
Figure 13B:
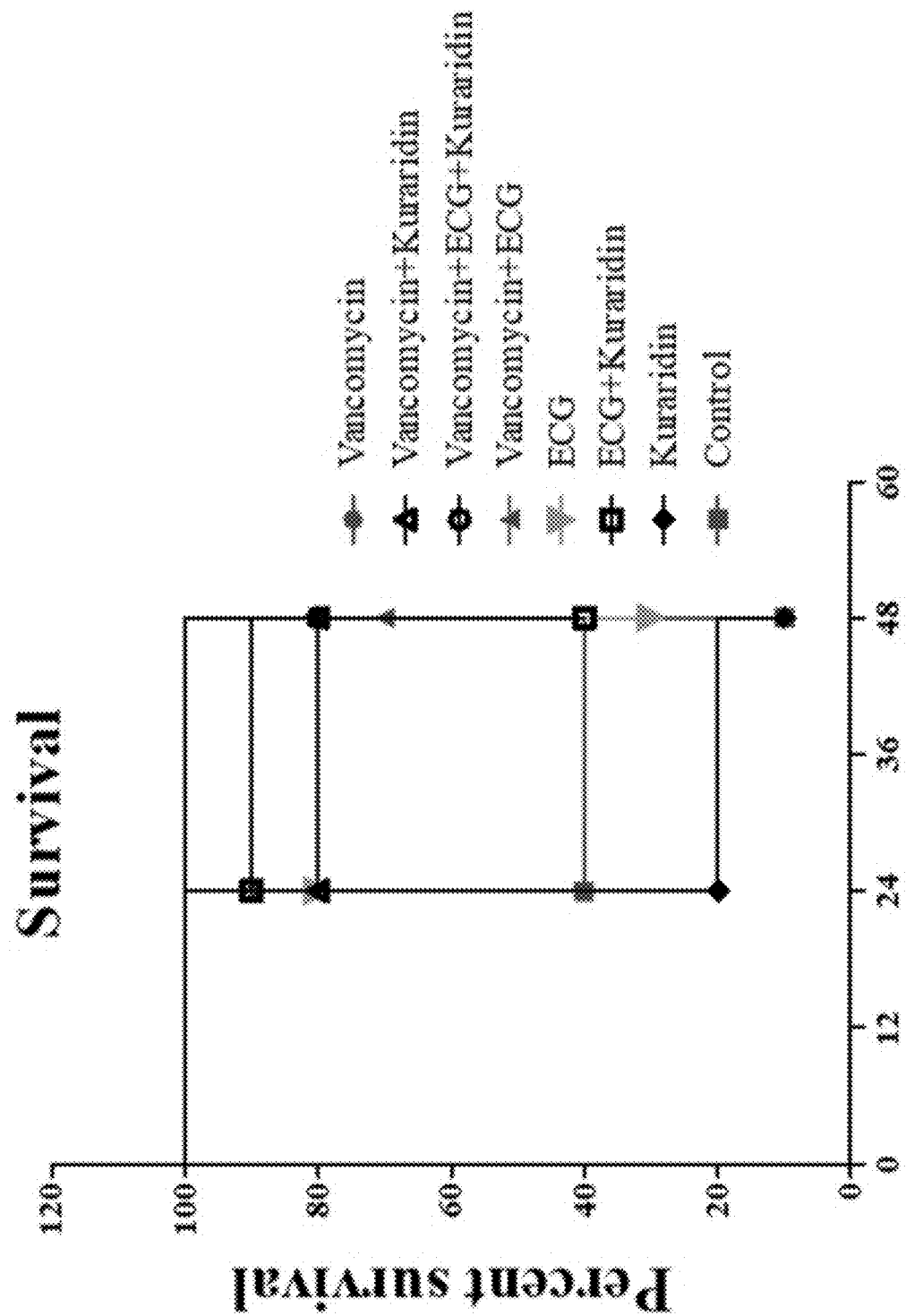
Figure 13C:
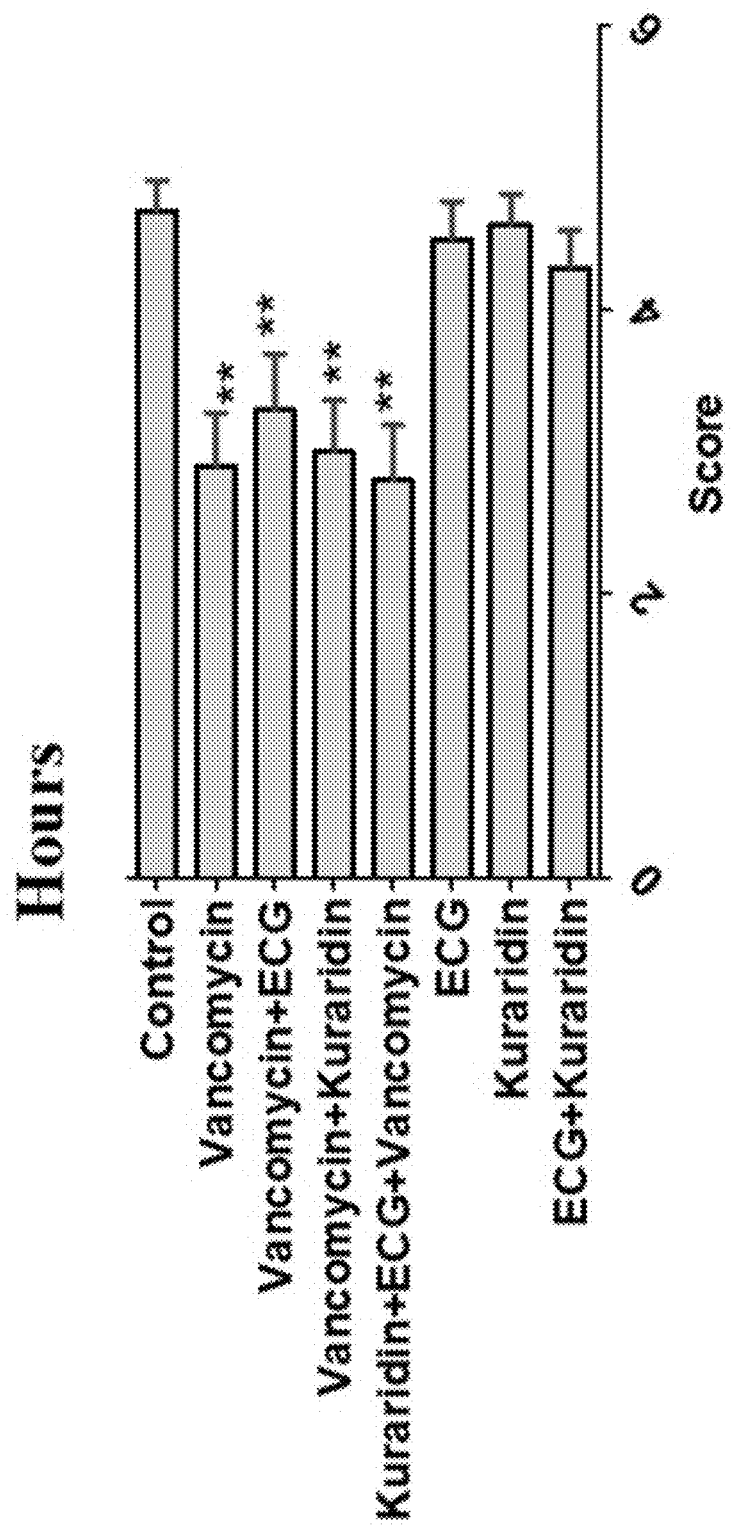
Figure 14:
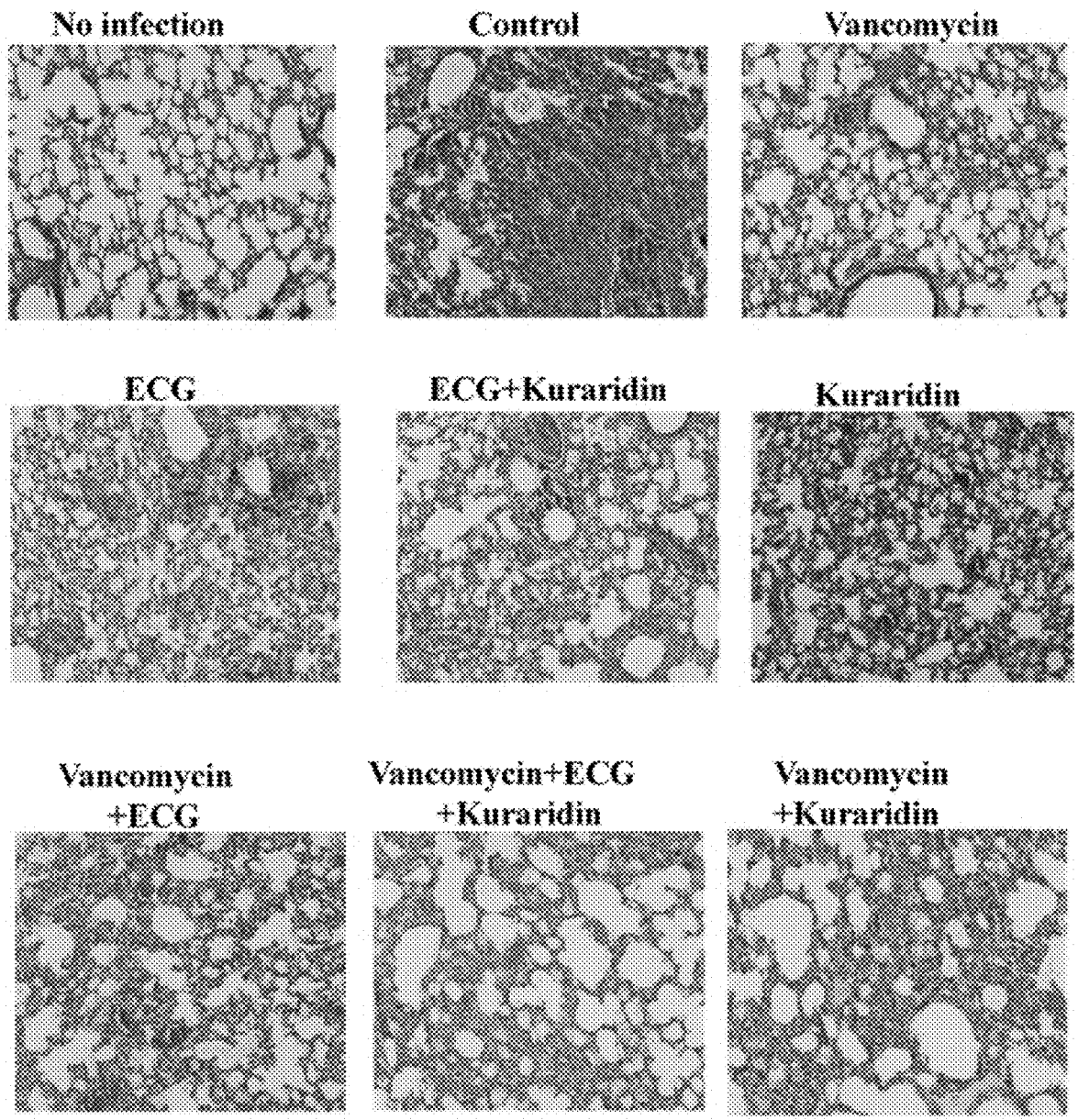
FIG. 14 Histology of lung tissue in normal mice without infection (No infection); mice infected with ATCC25923 (Control); infected mice treated with vancomycin (60 mg/kg), ECG (120 mg/kg) or kuraridin (120 mg/kg) alone; infected mice treated with ECG (120 mg/kg) and kuraridin (120 mg/kg); infected mice treated with ECG (120 mg/kg) and vancomycin (60 mg/kg); kuraridin (120 mg/kg) and vancomycin (60 mg/kg) and ECG (120 mg/kg), kuraridin (120 mg/kg) and vancomycin (60 mg/kg).

Similar findings were also observed in ATCC25923, for the mice treated with vancomycin, significant reduction of the mean bacteria counts to 6.064±0.425 log CFU was observed when compared with the control (8.909±0.101 log CFU) [FIG. 13(*a*)]. Combinations of ECG and kuraridin could not enhance the antibacterial activities of vancomycin. Slight reduction of bacteria counts was observed in the group treated with ECG and kuraridin (8.502±0.126). Compared with the survival rate of the control group (90%), improvements were observed in all the treatment groups except the group treated with kuraridin alone [FIG. 13(*b*)]. Improvement in pneumonia score [FIG. 13(*c*)] were observed in of the treatment groups with vancomycin (alone or combined other tested drugs). The tissue profiles of the vancomycin treated group was with fewer lesions, infiltration of leukocytes and erythrocytes in the airspace and the alveolar structure were preserved when compared with the control group (FIG. 14).

Figure 15:
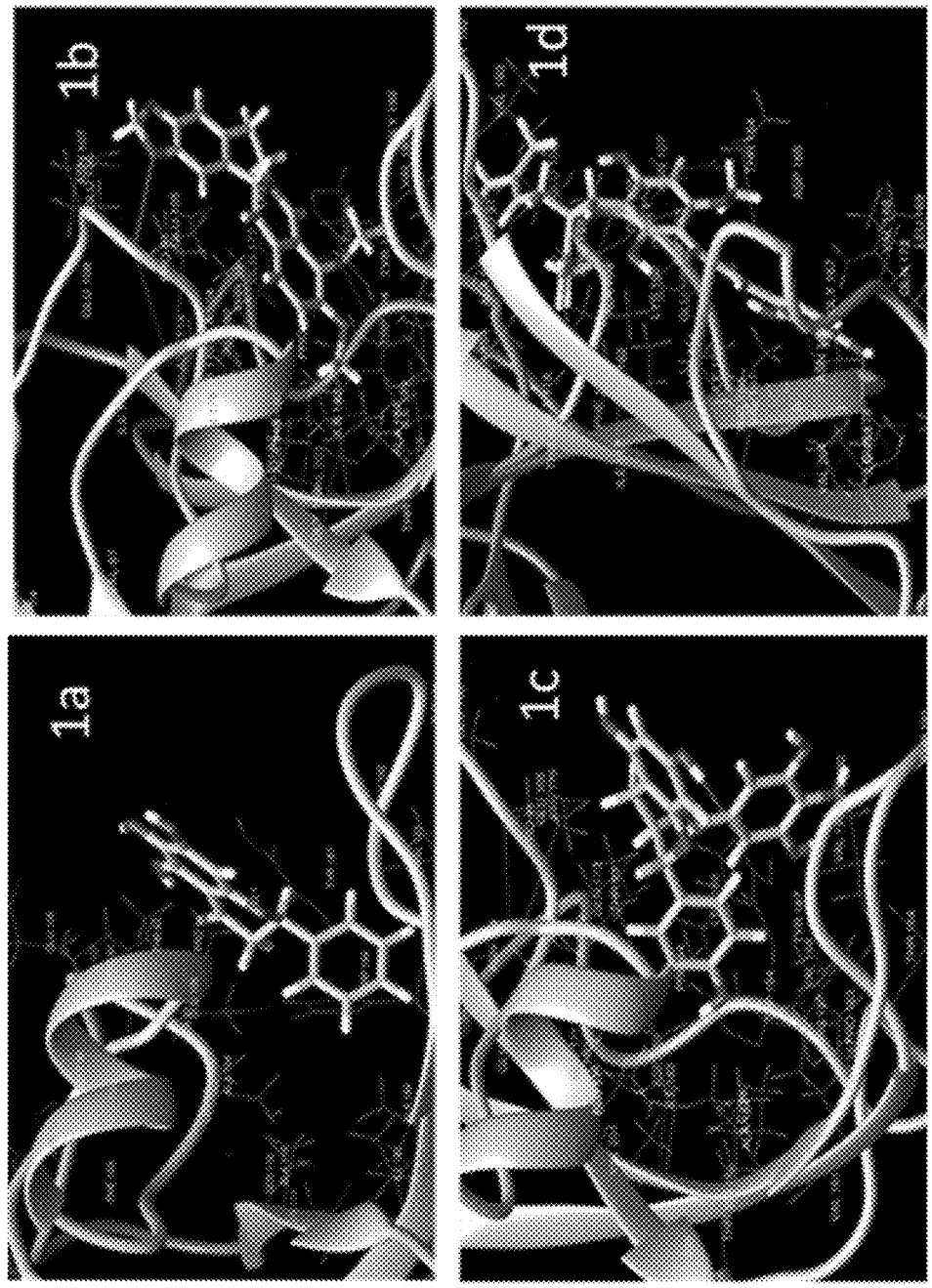
FIG. 15 Visualization of the most energetically favorable binding mode of the ligands baicalein (a), berberine (b), epicatechin gallate (c) and kuraridin (d) into Sortase A, The predicted hydrogen bond interactions between selected ligands with the protein as visualized by Chimera are shown. For clarity, only interacting important residues are displayed and part of the enzyme in the background was visualized in Ribbon style using the UCSF Chimera. The docking studies predicted steric interactions of all the four ligands with the amino acid residues of the active site, however, hydrogen bond interactions were predicted only for berberine, ECG and kuraridin. One hydrogen bond was predicted between berberine and GLU 106 (b), one hydrogen bond was predicted between ECG and TRP194 as shown by the green line in FIG. 1c, and two Hydrogen bonds were predicted between kuraridin and GLN178 and ARG 197 respectively as shown in (b).
Figure 16A:
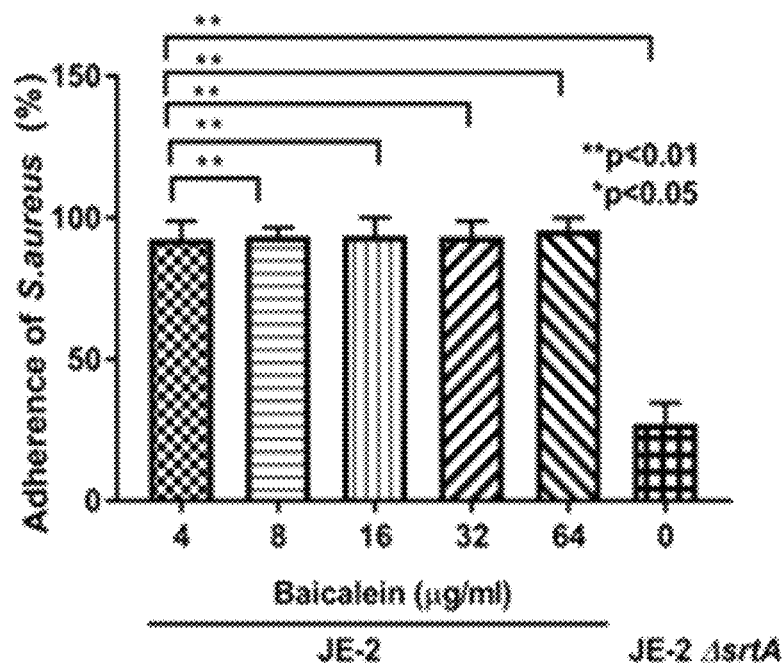
FIGS. 16A-16D Fibrinogen-binding adherence of MRSA strain JE-2 and its isogenic mutant ΔsrtA with varying concentrations of baicalein (a), berberine (b), ECG (c) and kuraridin (d). Adherence of MRSA strain JE-2 to fibrinogen was taken as 100%. The error bars represent the standard deviation of the mean values. Significance was determined by One-way ANOVA (*$p<0.05$, **$p<0.01$). Adhesion of bacteria to fibrinogen (Fg)-coated 96-well plates was quantified by absorbance following fixing of bacteril and staining crystal violet, and read at OD570 nm. In (FIGS. 16A-16D), the ΔSrtA showed the minimum binding rate of 27.1±7.1% to Fg. While minimal reduction in adherence were observed with baicalein (FIG. 16A), there is dose-dependent reduction of adherence with berberine (FIG. 16B) and ECG (FIG. 16C). The most significant reduction in the adherence of the WT strain is with kuraridin, reaching 100% at 1.0 μg/ml (FIG. 16D).
Figure 16B:
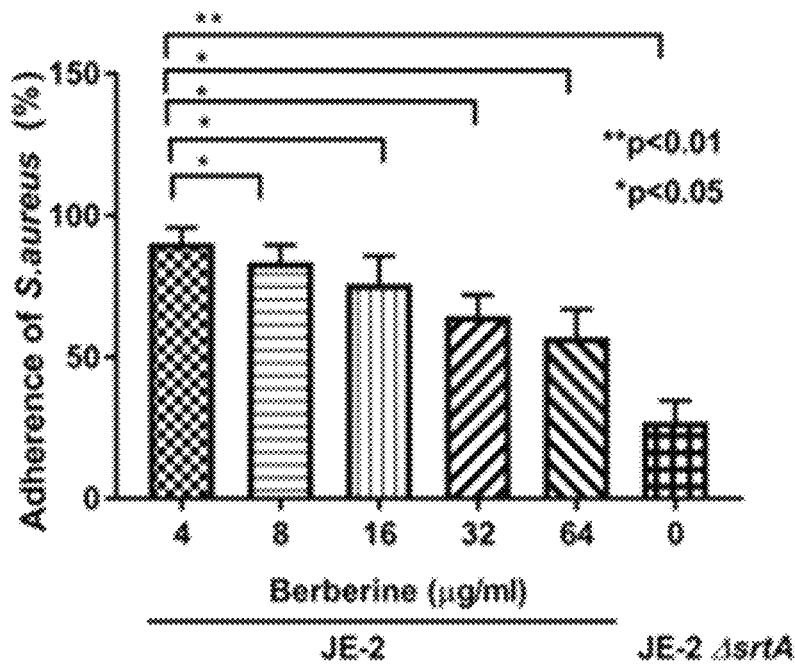
Figure 16C:
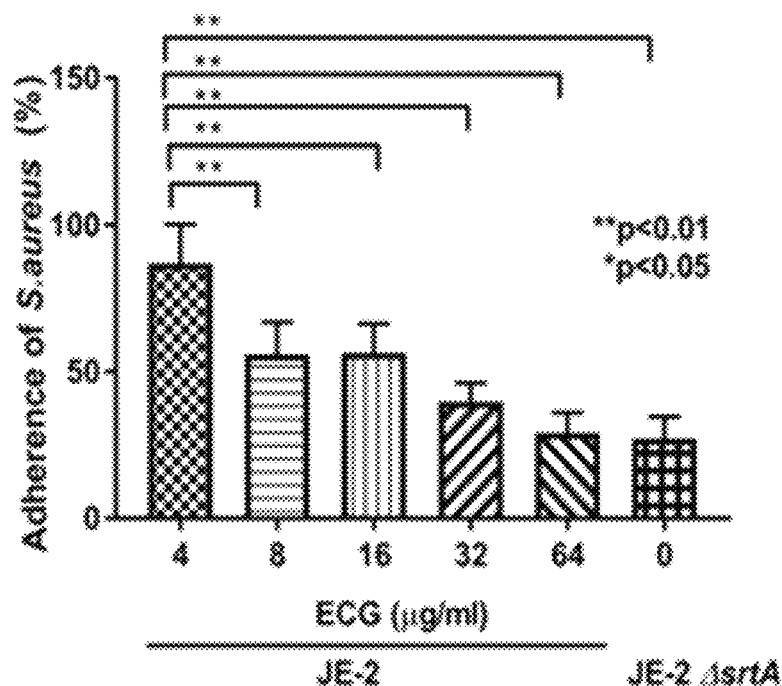
Figure 16D:
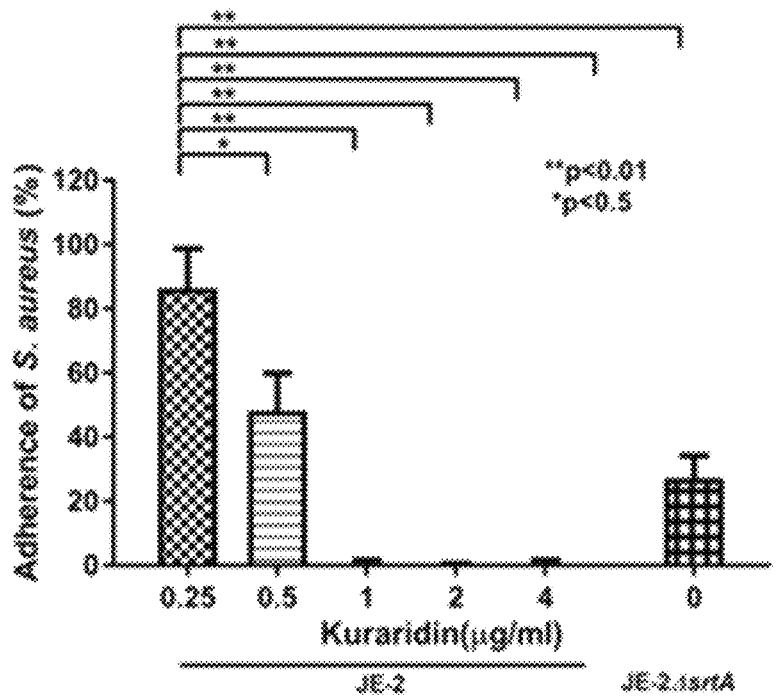
Figure 17A:
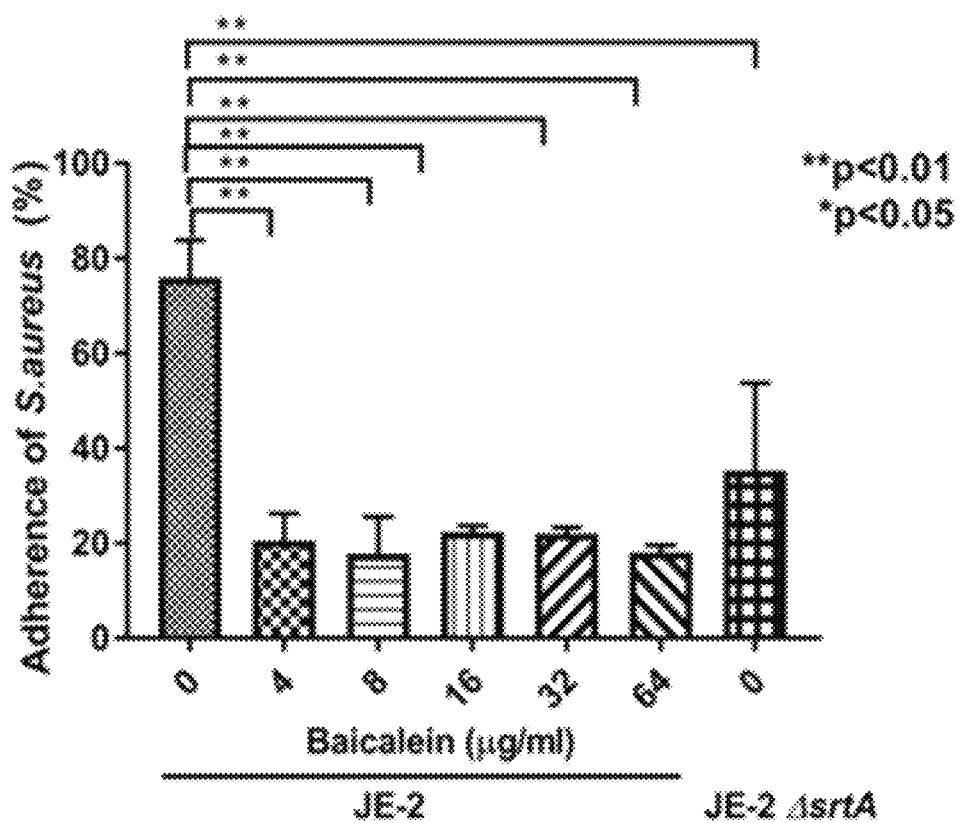
FIG. 17A-17H Adherence and internalization of *S. aureus* by keratinocytes.
Figure 17B:
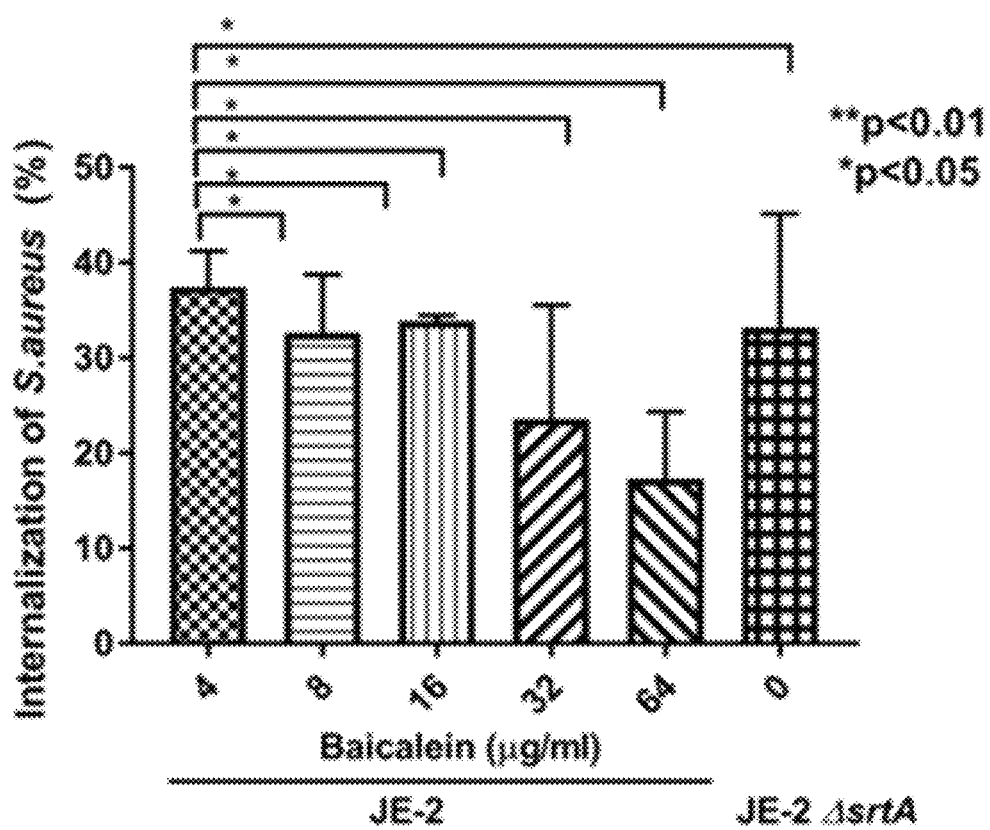
Figure 17C:
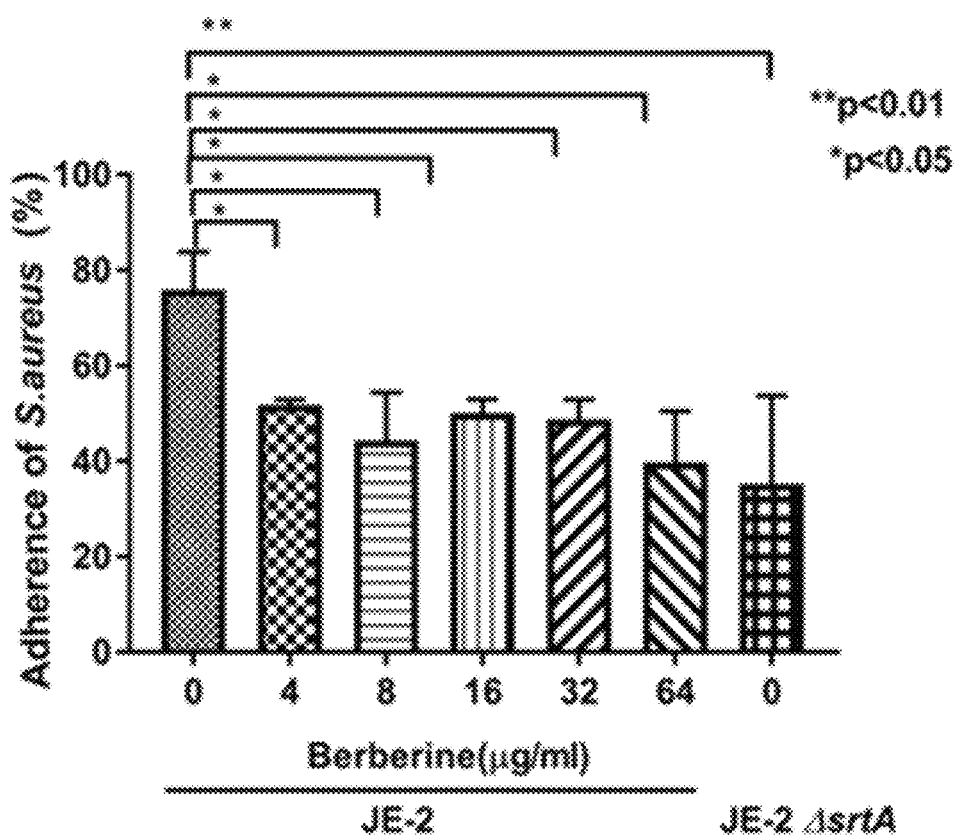
Figure 17D:
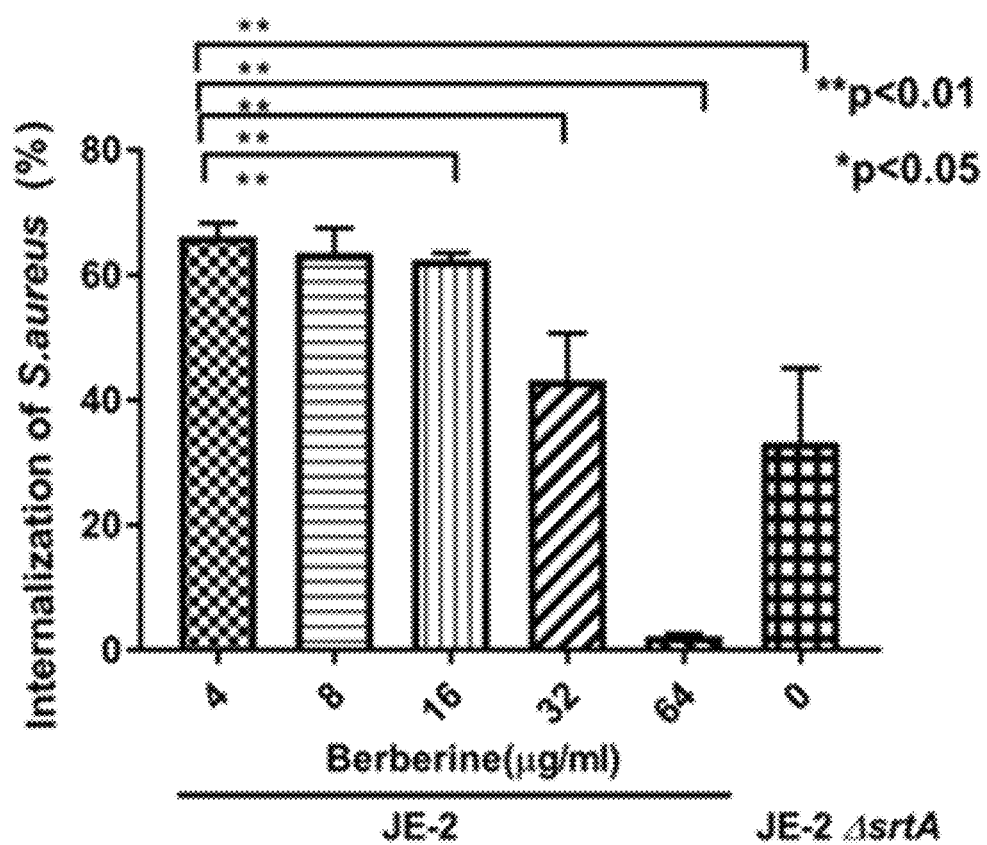
Figure 17E:
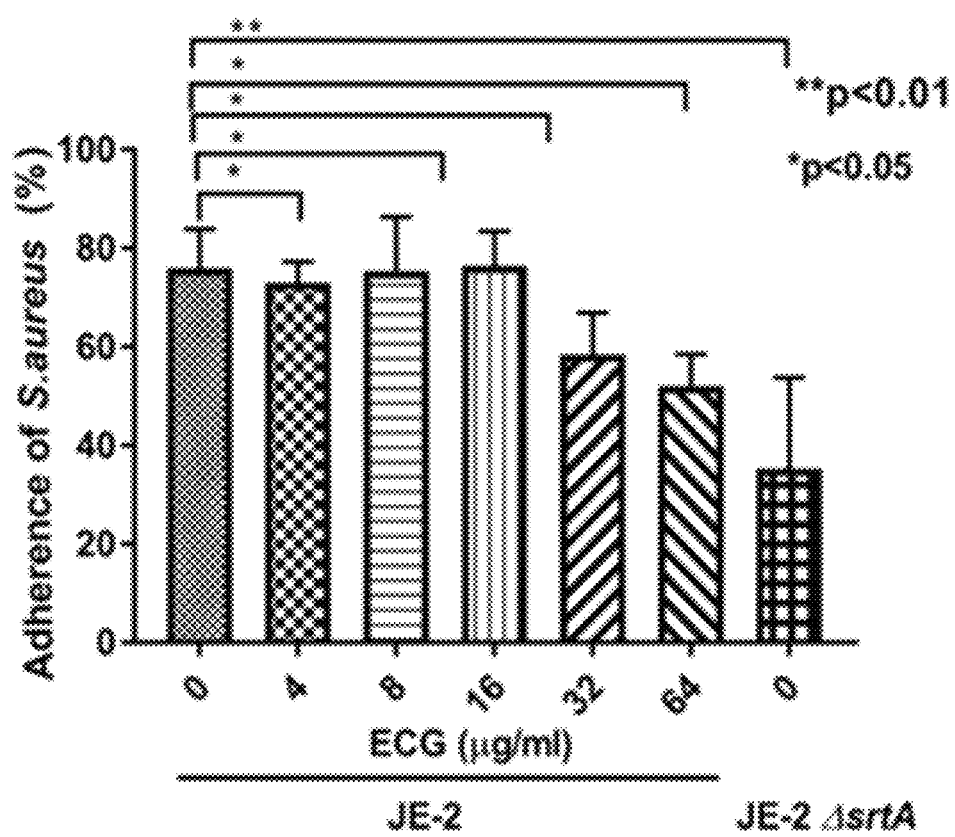
Figure 17F:
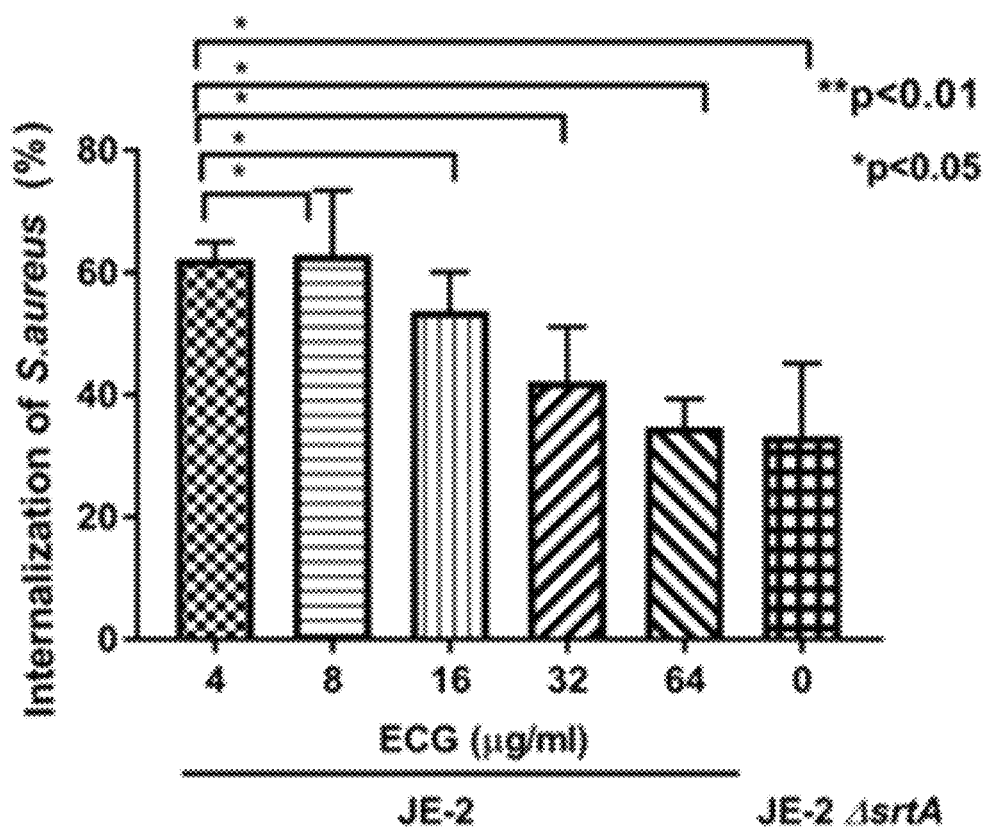
Figure 17G:
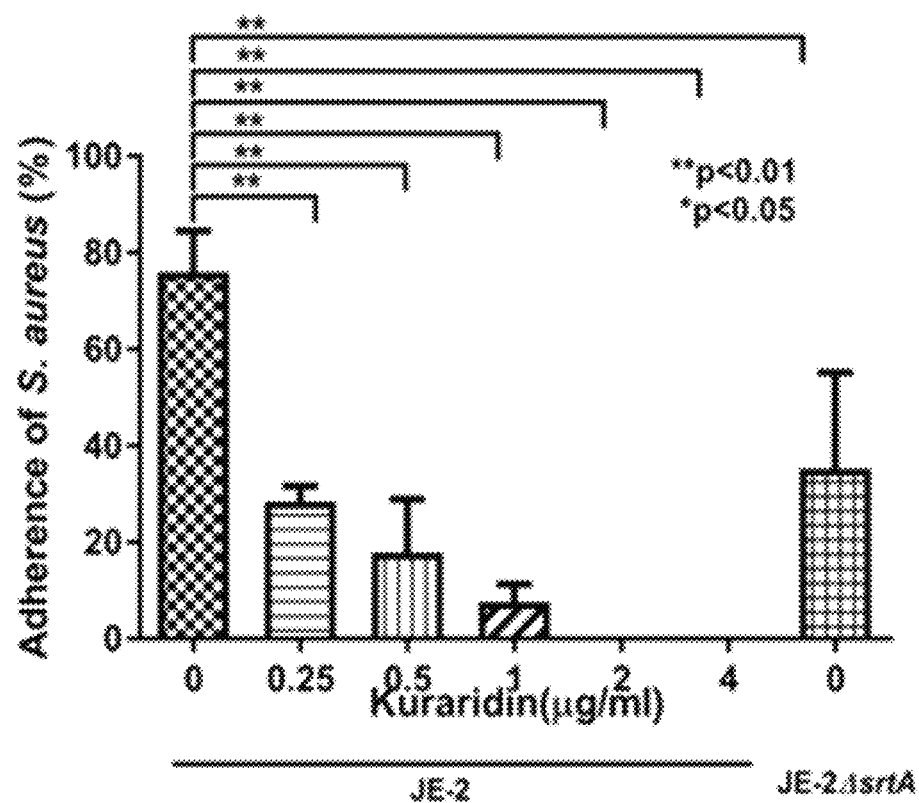
Figure 17H:
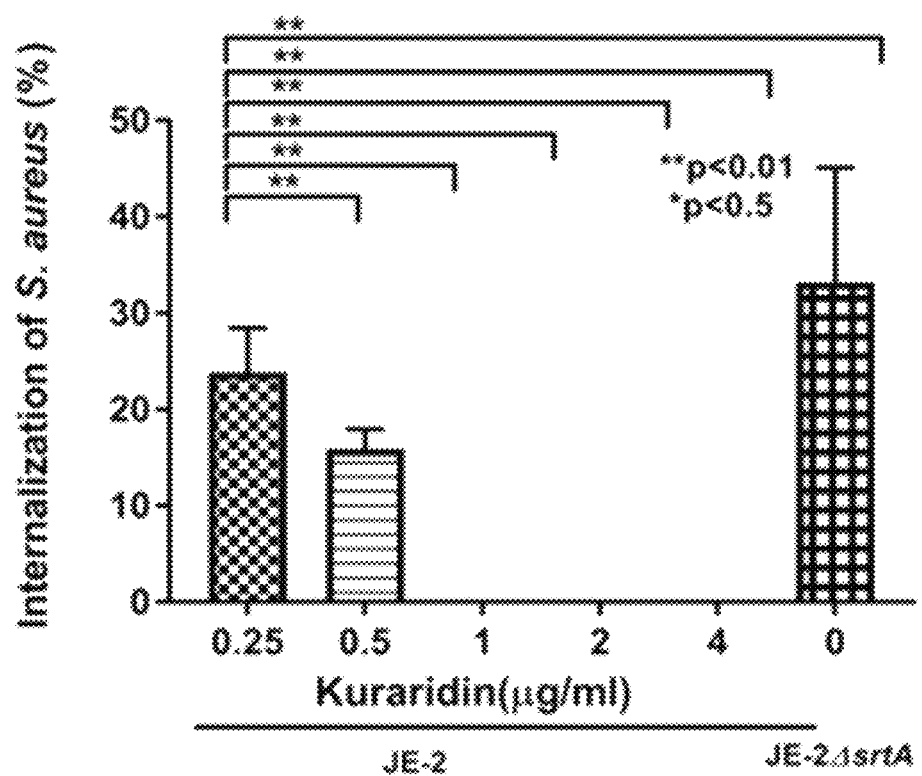
Figure 18:
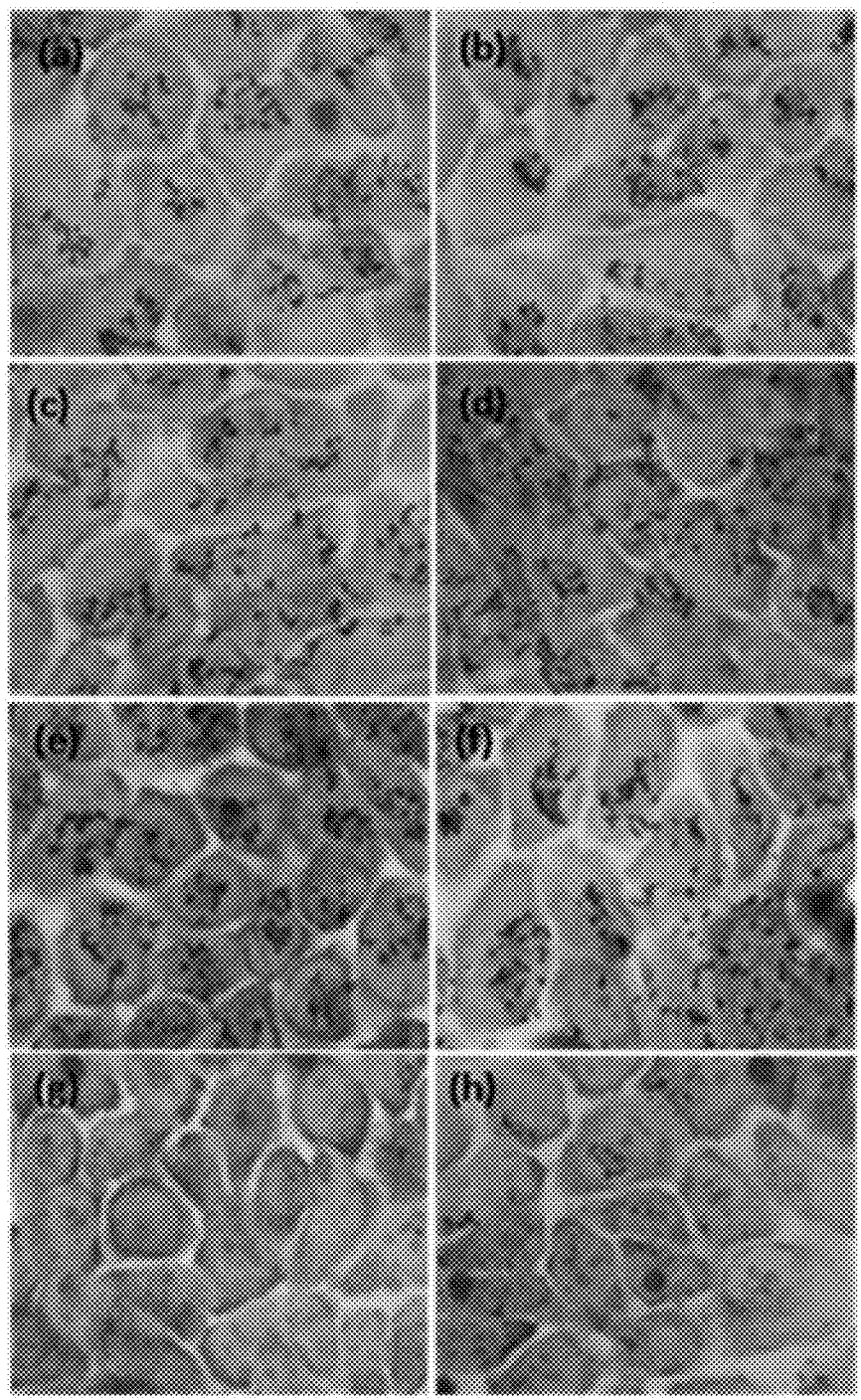
FIG. 18 Microscopic examination of adherence of *S. aureus* to Hacat keratinocytes by Giemsa staining, with and without treatment with baicalein. (a-f) Adherence of strain JE-2 to keratinocytes treated with 64, 32, 16, 8, 4 and 0 μg/ml baicalein. (g) Hacat keratinocytes without *S. aureus* infections. (h) Adherence of JE-2ΔsrtA to keratinocytes.
Figure 19:
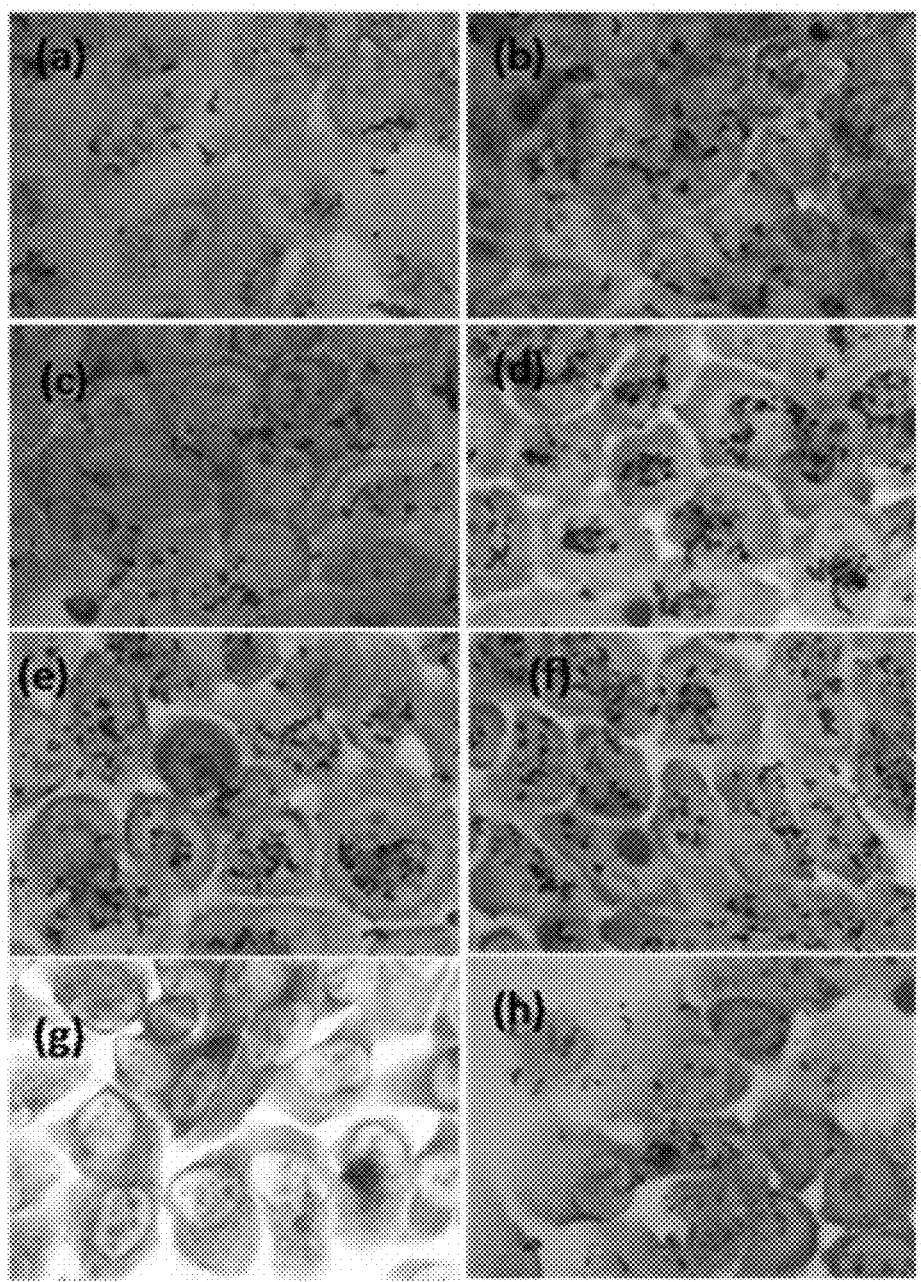
FIG. 19 Microscopic examination of adherence of *S. aureus* to Hacat keratinocytes by Giemsa staining, with and without treatment with ECG. (a-f) Adherence of strain JE-2 to keratinocytes under 64, 32, 16, 8, 4 and 0 μg/ml ECG. (g) Hacat keratinocytes without *S. aureus* infections. (h) Adherence of JE-2ΔsrtA to keratinocytes.
Figure 20:
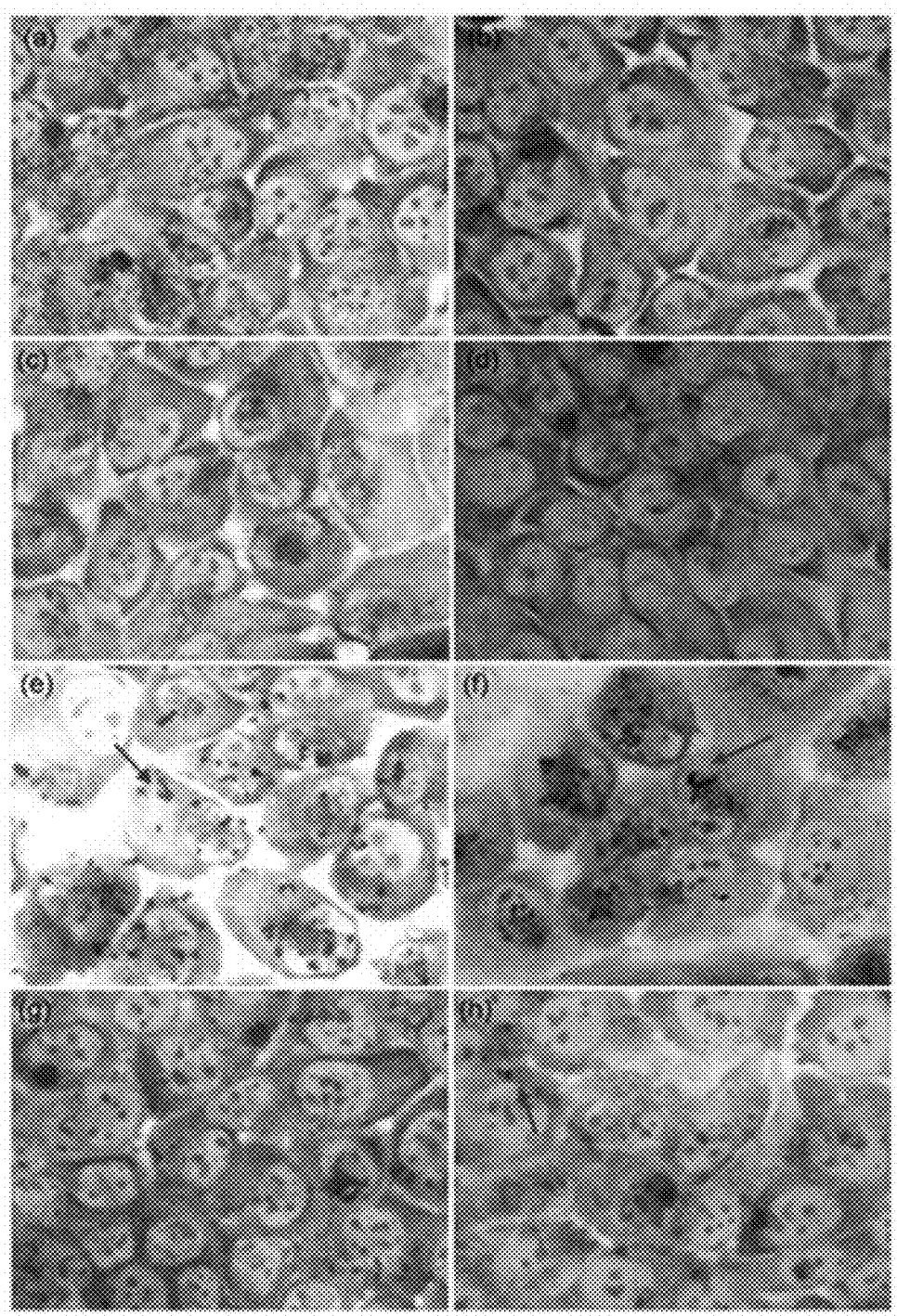
FIG. 20 Microscopic examination of adherence of *S. aureus* to Hacat keratinocytes by Giemsa staining, with and without treatment with kuraridin. (a-f) Adherence of strain JE-2 to keratinocytes under 4, 2, 1, 0.5, 0.25 and 0 μg/ml kuraridin. (g) Hacat keratinocytes without *S. aureus* infections. (h) Adherence of JE-2ΔsrtA to keratinocytes. The blue dots (red arrows) are *S. aureus*.
Figure 21A:
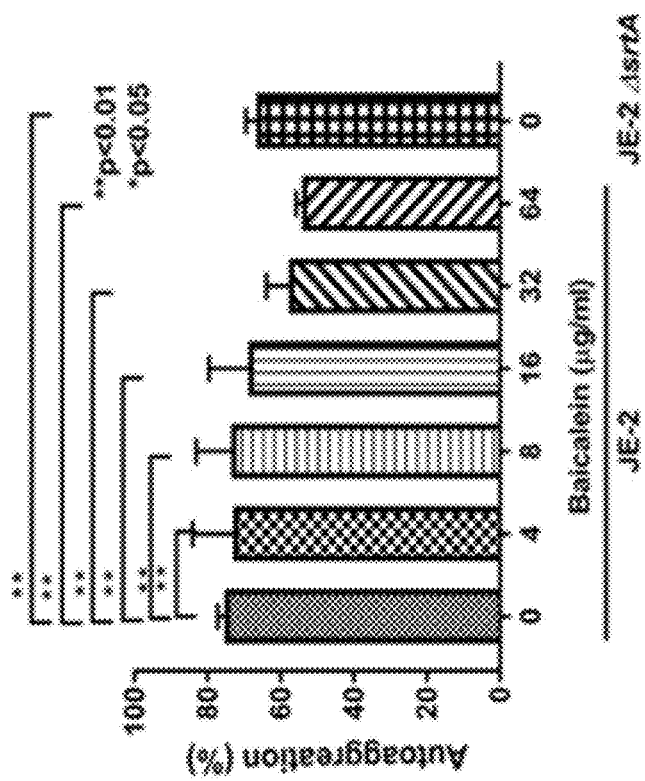
FIGS. 21A-21D Bacterial aggregation of MRSA JE-2 and its isogenic ΔSrtA under varying concentrations of baicalein (a), berberine (b), ECG (c) and kuraridin (d). Aggregation of strain JE-2 was taken as 100%. The error bars represent the standard deviation of the mean values. Significance was determined by One-way ANOVA (*$p<0.05$, **$p<0.01$). Upon treatment with kuraridin (d), the percentage of bacterial aggregation was observed to be 76.1±3.0, 78.1±1.7, 48.1±6.5, 37.3±7.3, 17.7±4.6 respectively. A 4.4-fold reduction in bacterial aggregation was observed at 4 μg/ml as compared to the wild type without drug. The aggregation was significantly lower than the mutant ΔSrtA which was measured to be 3.7 folds. No significant reduction in bacterial aggregation was observed upon treatment with ECG (p>0.05) (c). Bacterial aggregation was reduced for baicalein and berberine, but less significantly than with kuraridin (FIGS. 21A, 21B). Only a 10% reduction in aggregation was observed in ΔSrtA (66.7±2.7%) as compared to the WT strain (75.4±1.7).
Figure 21B:
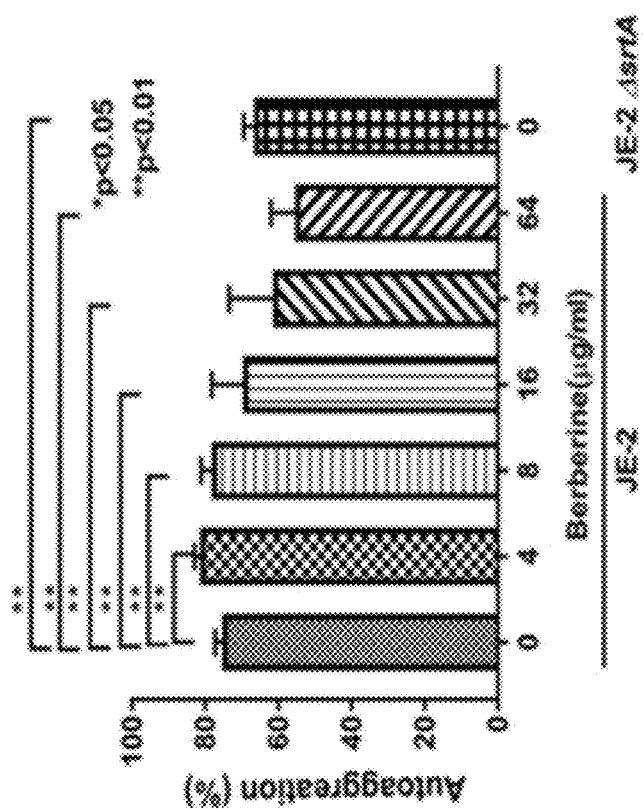
Figure 21D:
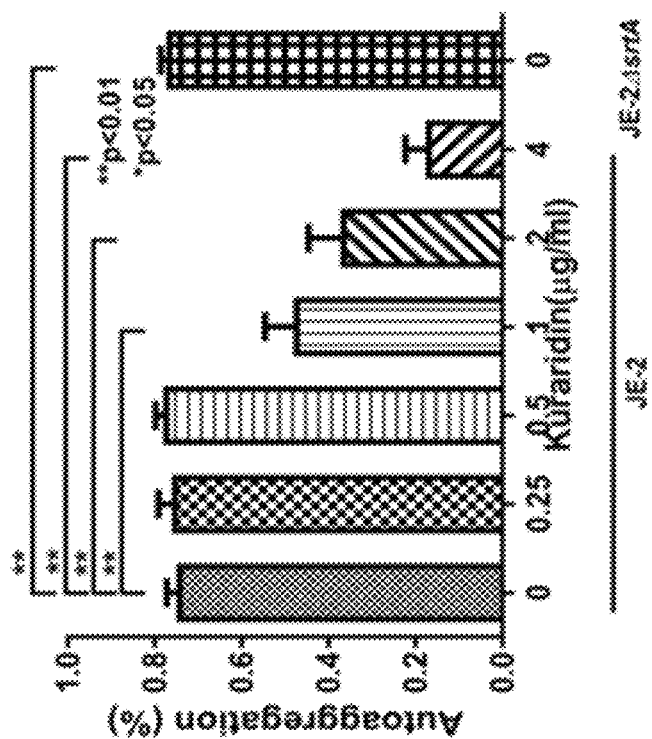
Figure 21C:
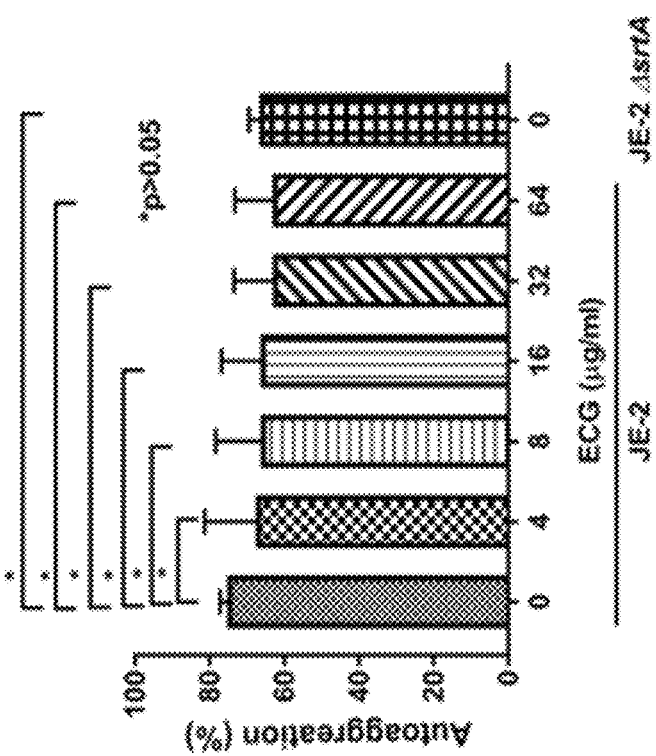
Figure 22A:
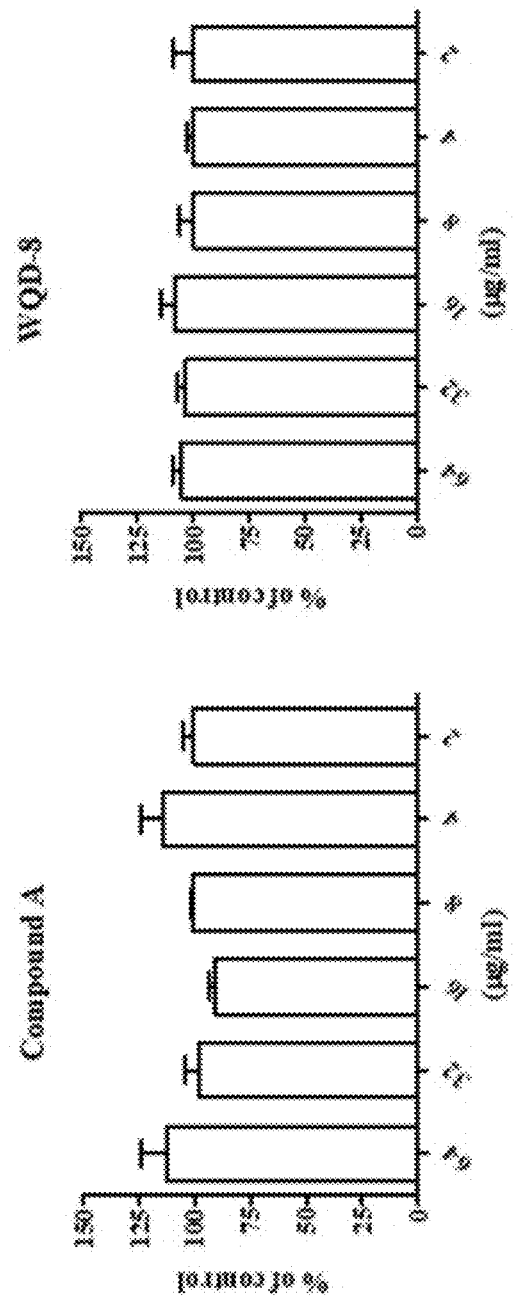
FIGS. 22A-22B FIG. 22A. Cellular toxicity (XTT assay) of kuraridin and its analogues on human peripheral blood mononuclear cells (PBMCs). The results were expressed as % growth of drug free control±standard error of mean (n=3). All compounds were non-toxic at concentrations up to 64 µg/ml, except for WQD101, WQD164.
Figure 22A:
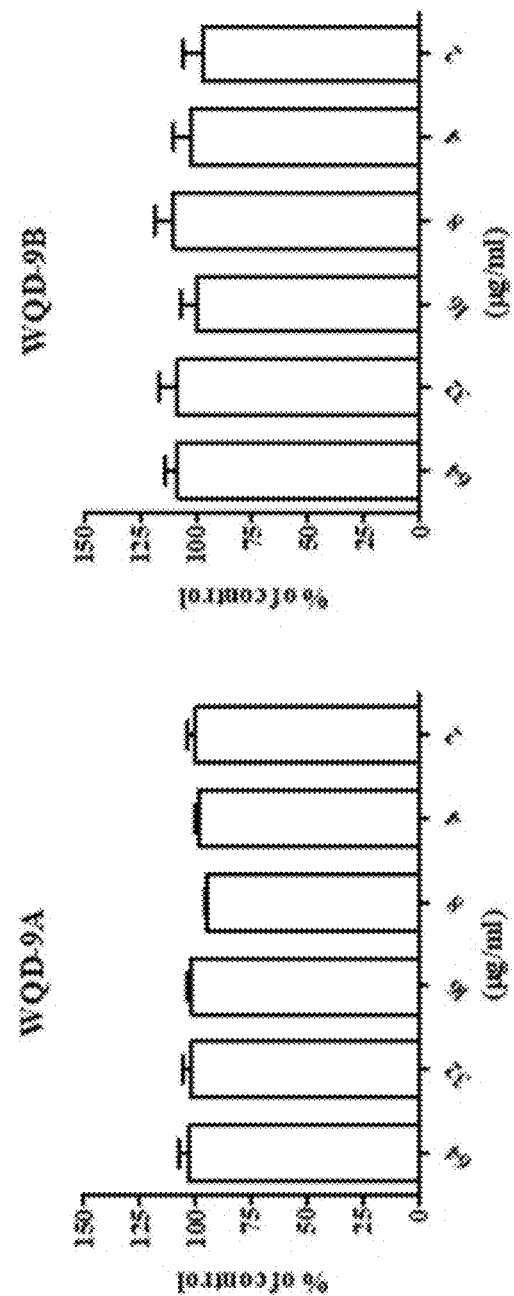
Figure 22A:
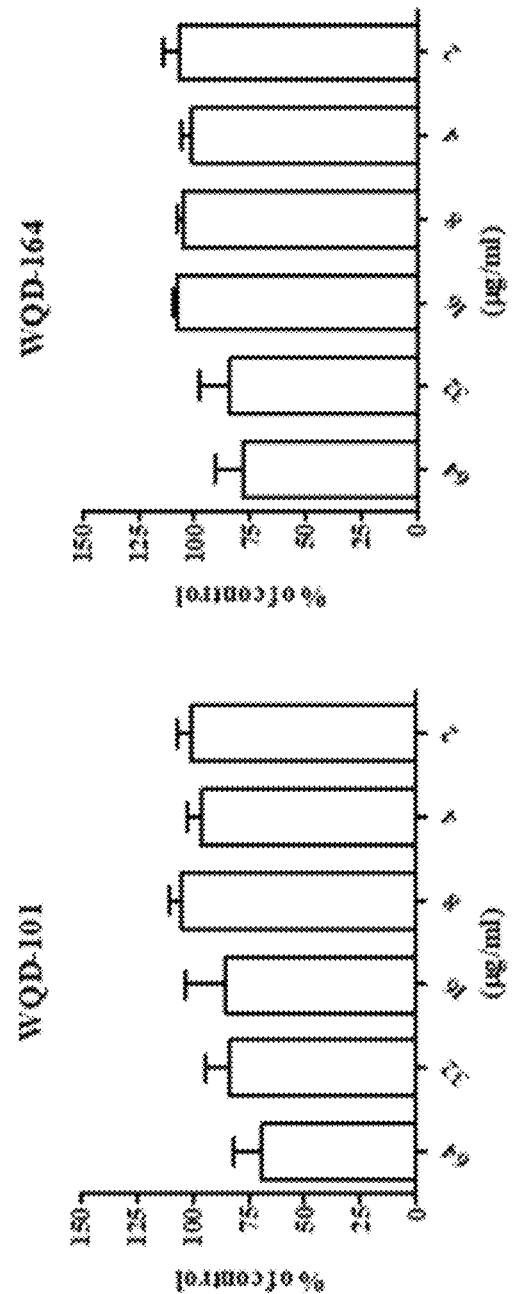
Figure 22B:
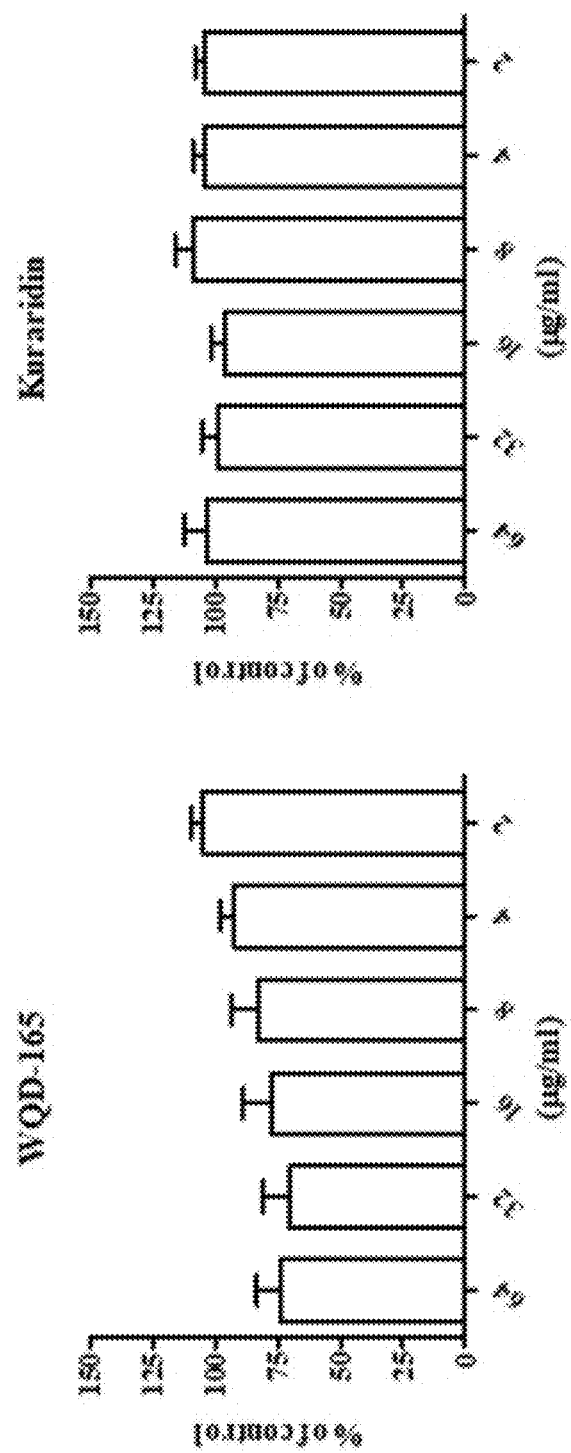
Figure 22B:
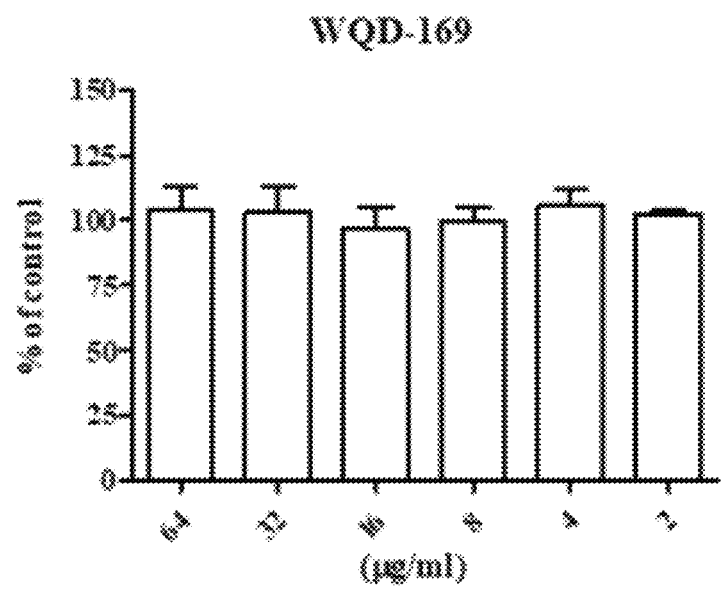
Figure 22B:
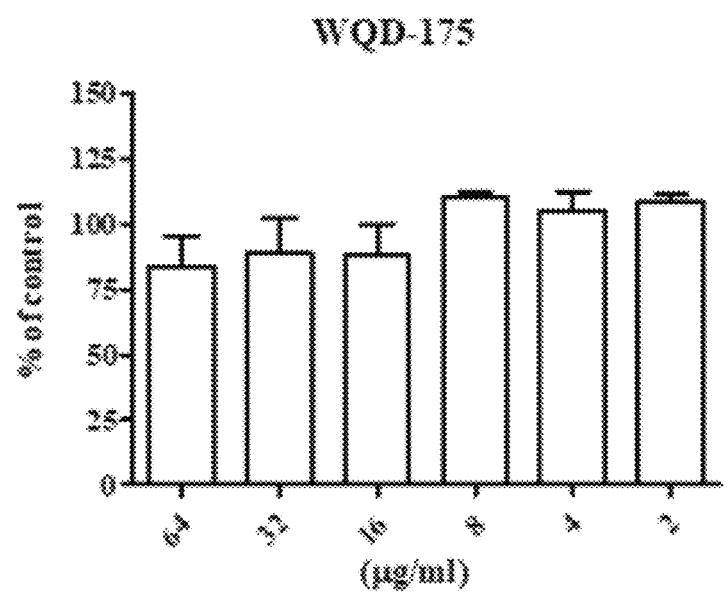
Figure 23:
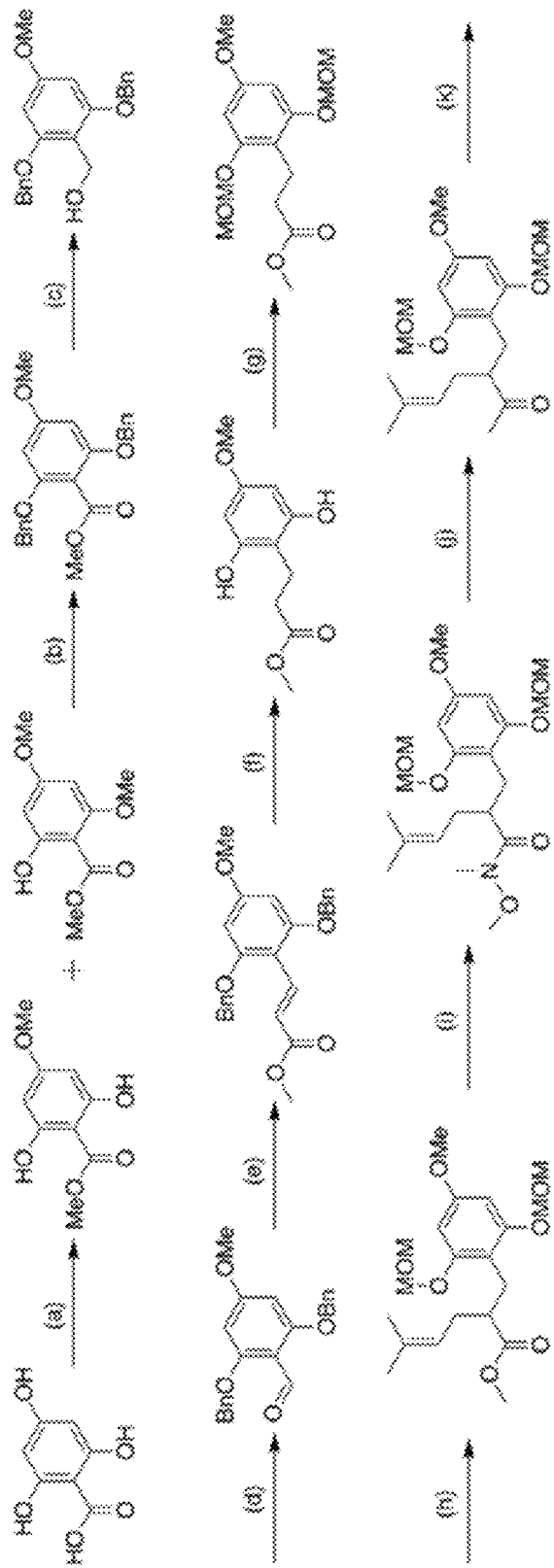
FIG. 23 Synthetic sequences of kuraridin, its analogues and intermediates.
Figure 23:
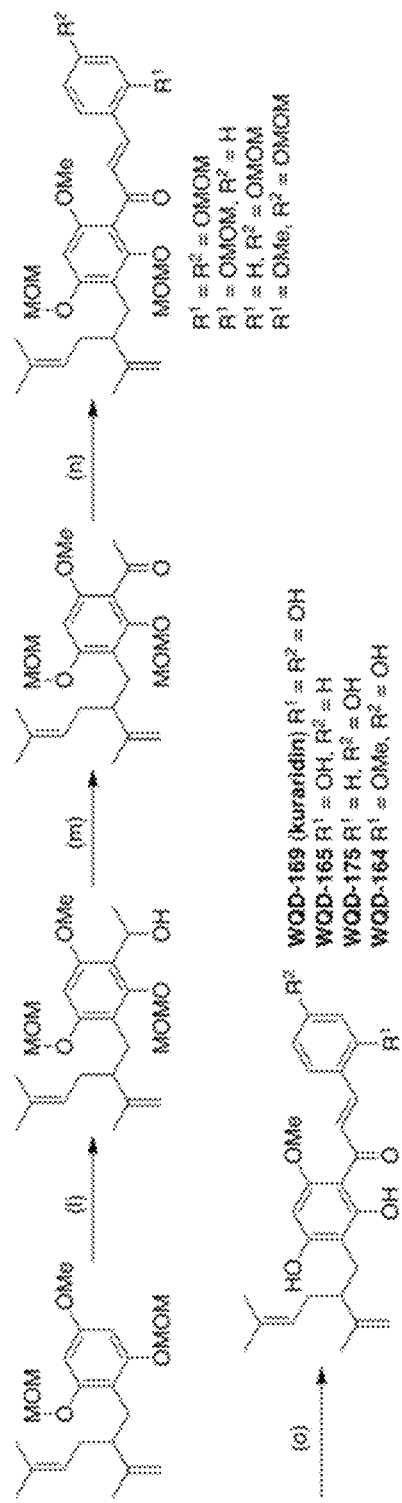
Figure 24:
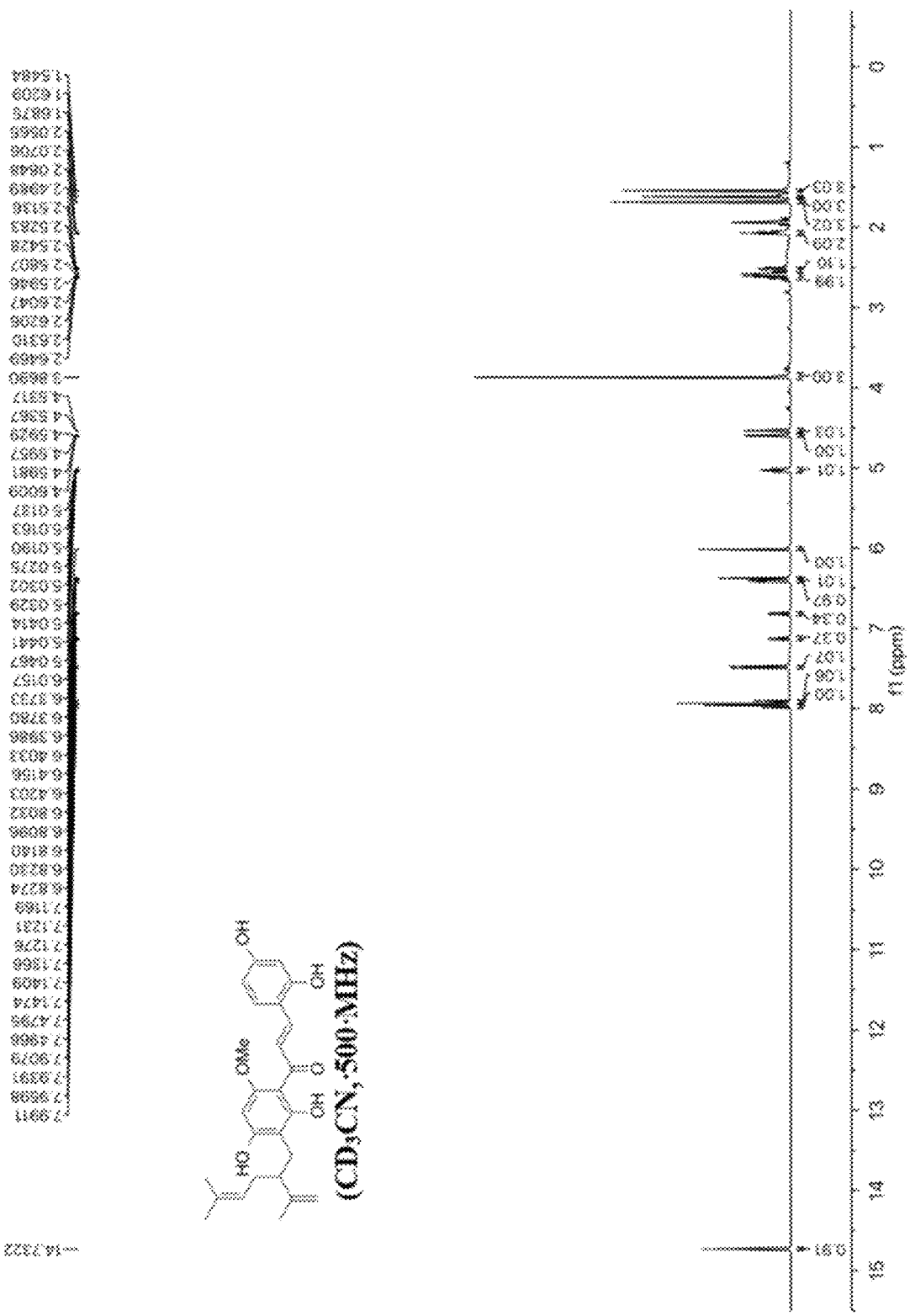
FIGS. 24-32 Spectroscopic data of kuraridin analogues
Figure 25:
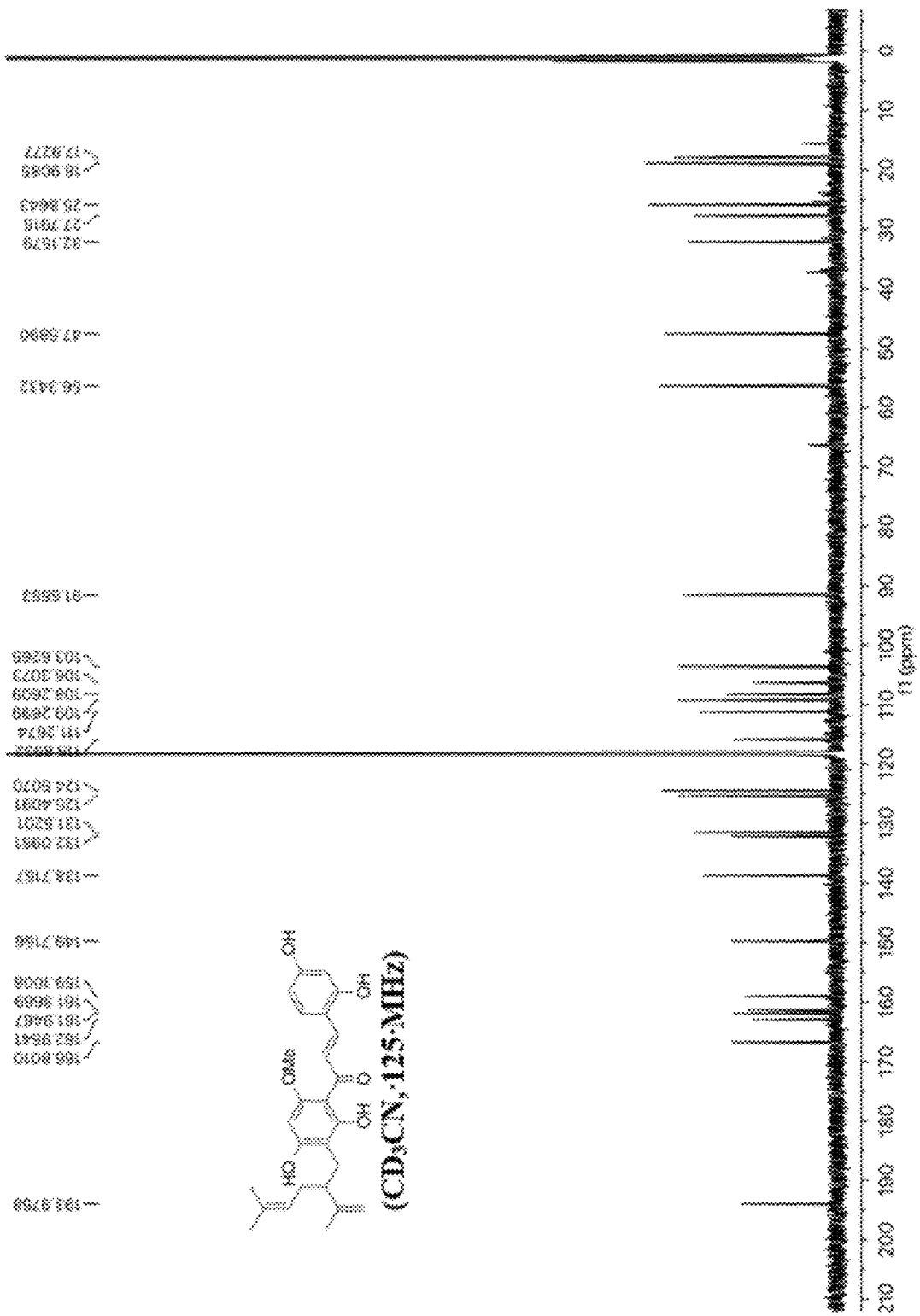
Figure 26:
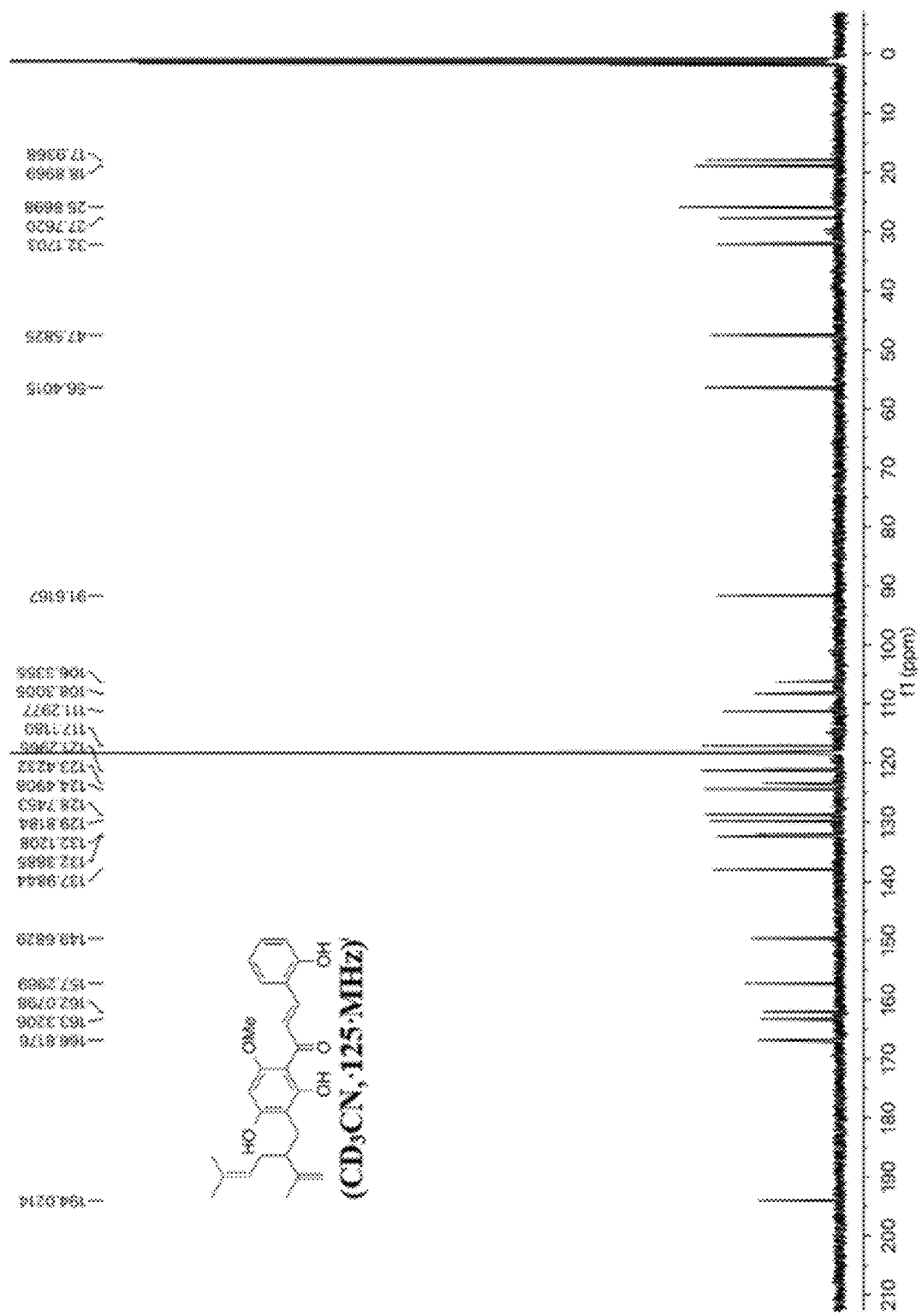
Figure 27:
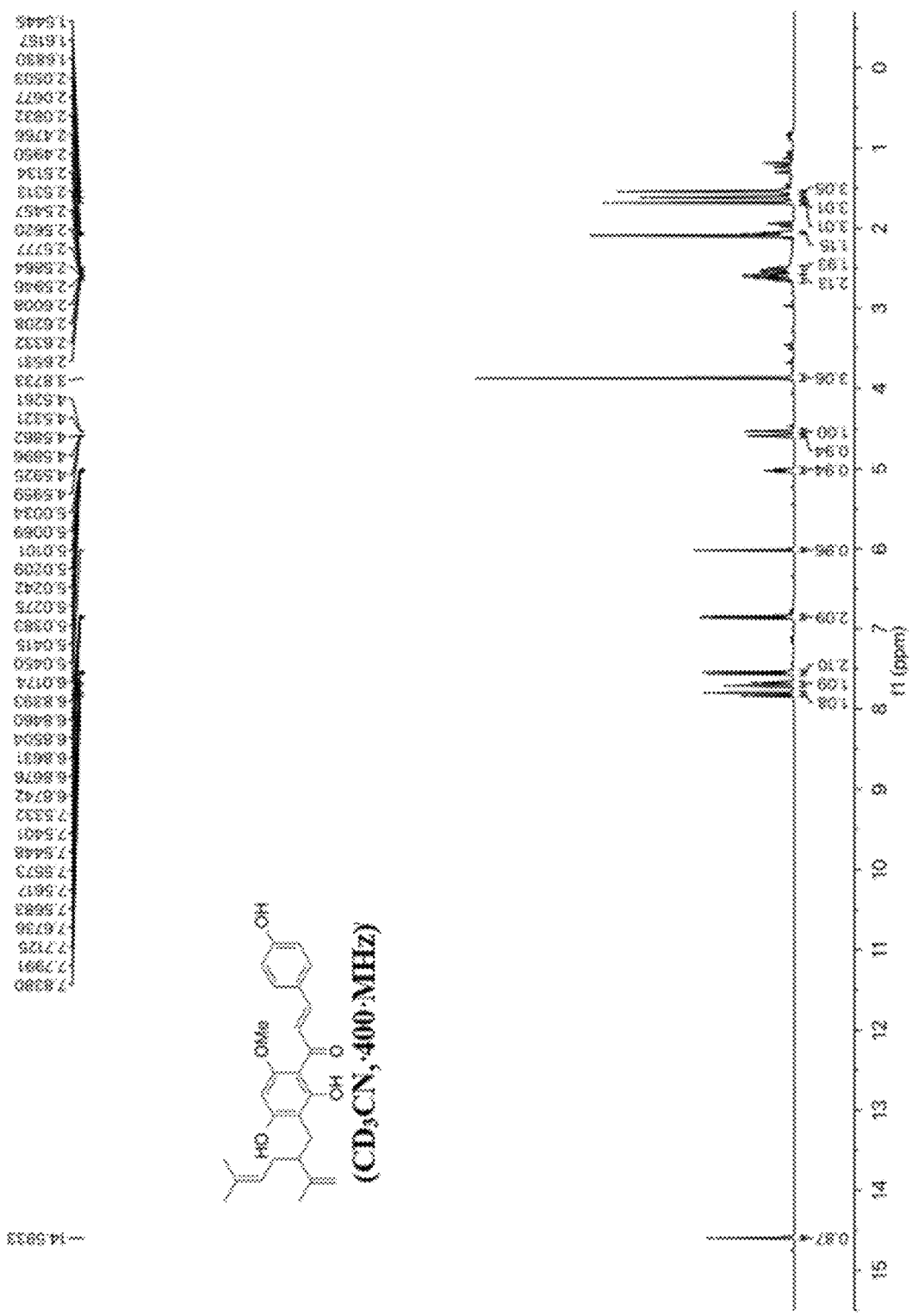
Figure 28:
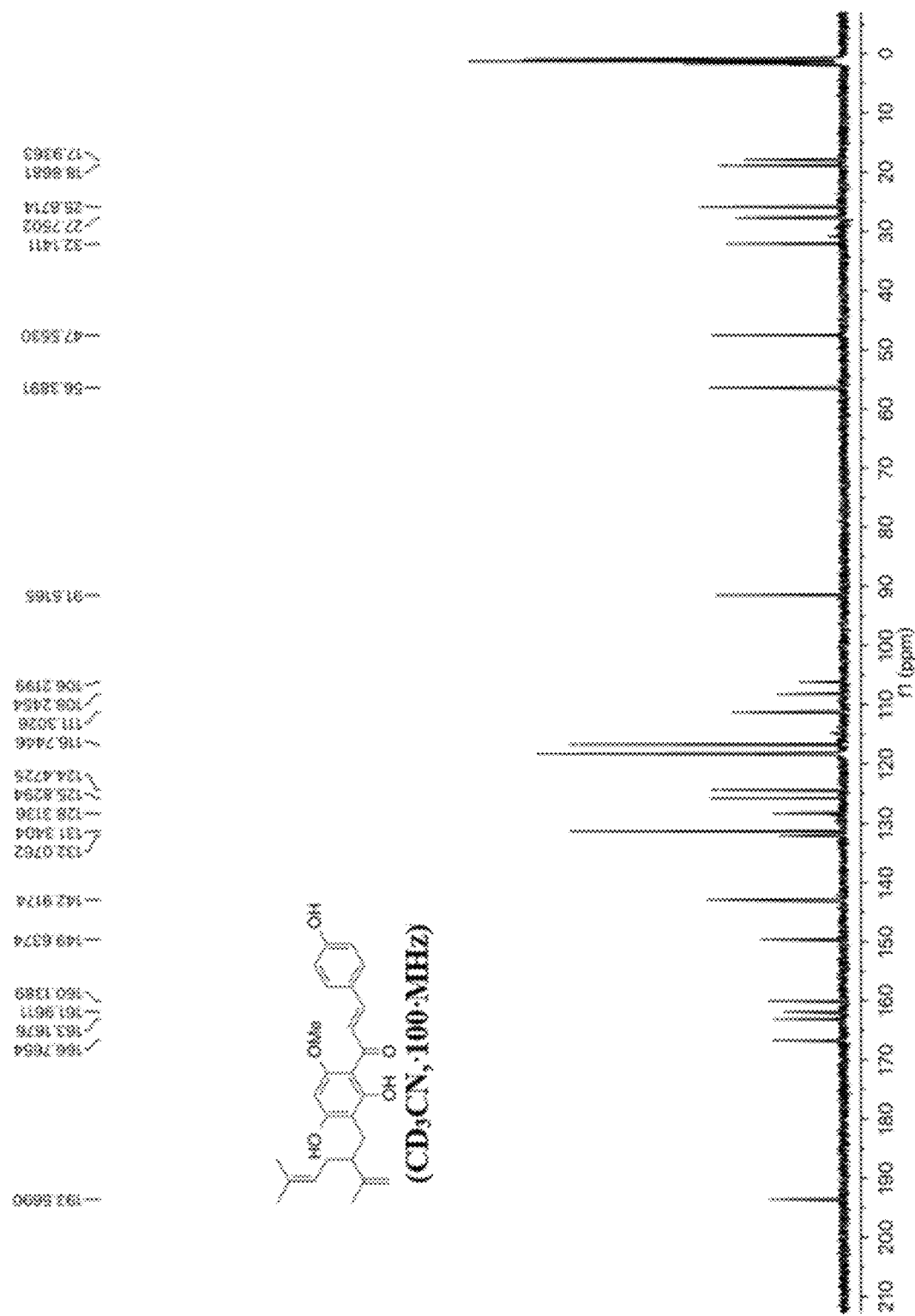
Figure 29:
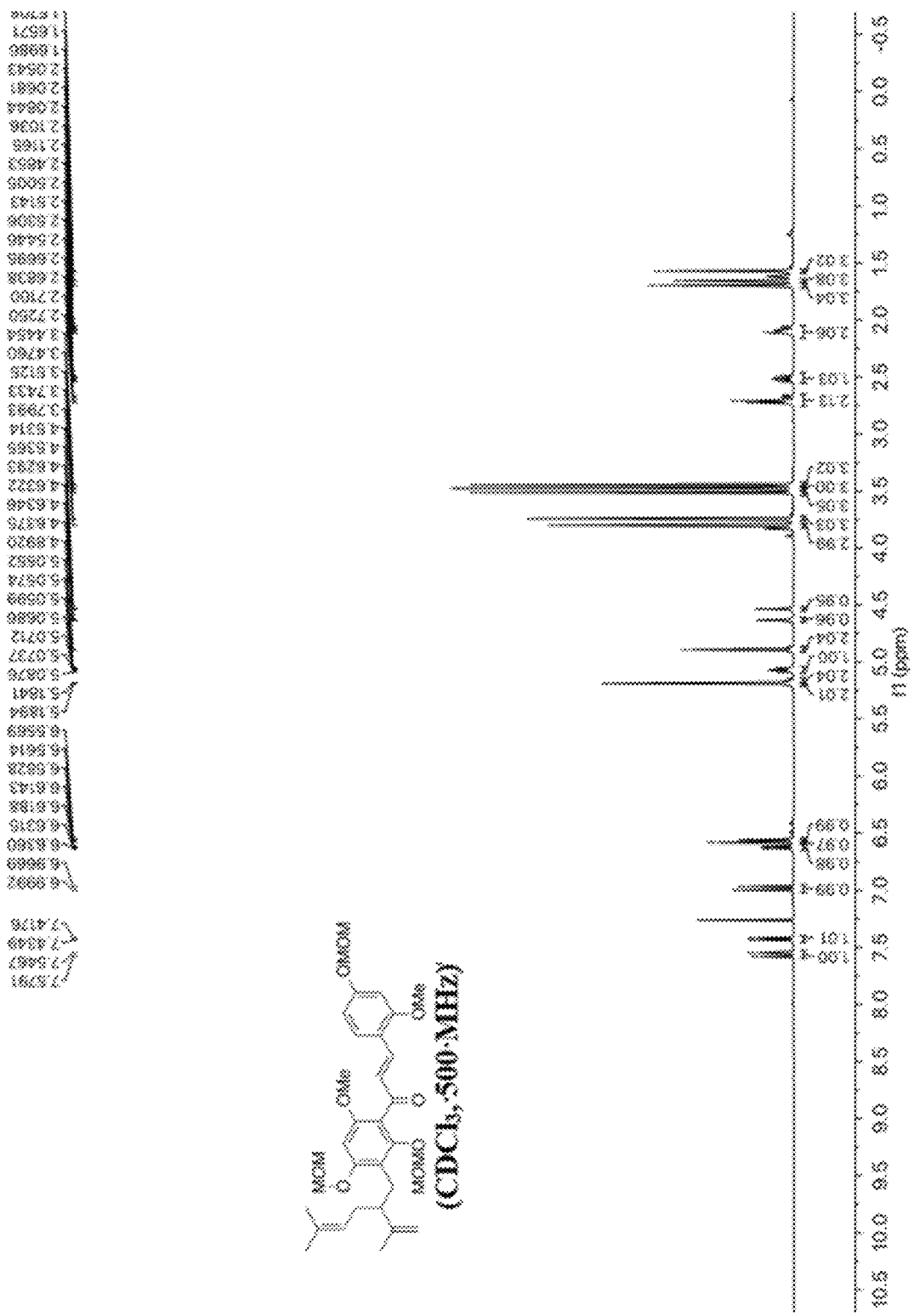
Figure 30:
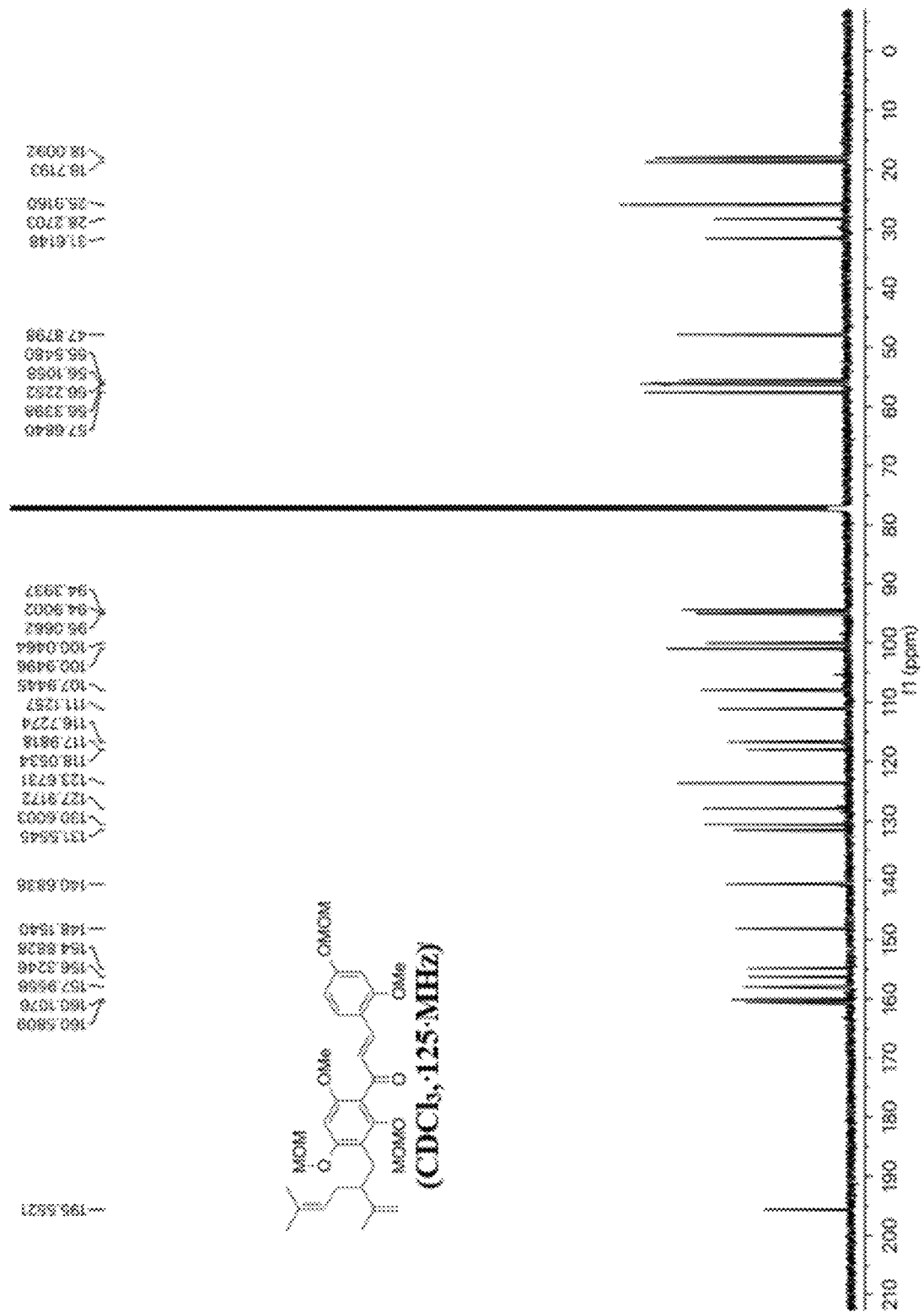
Figure 31:
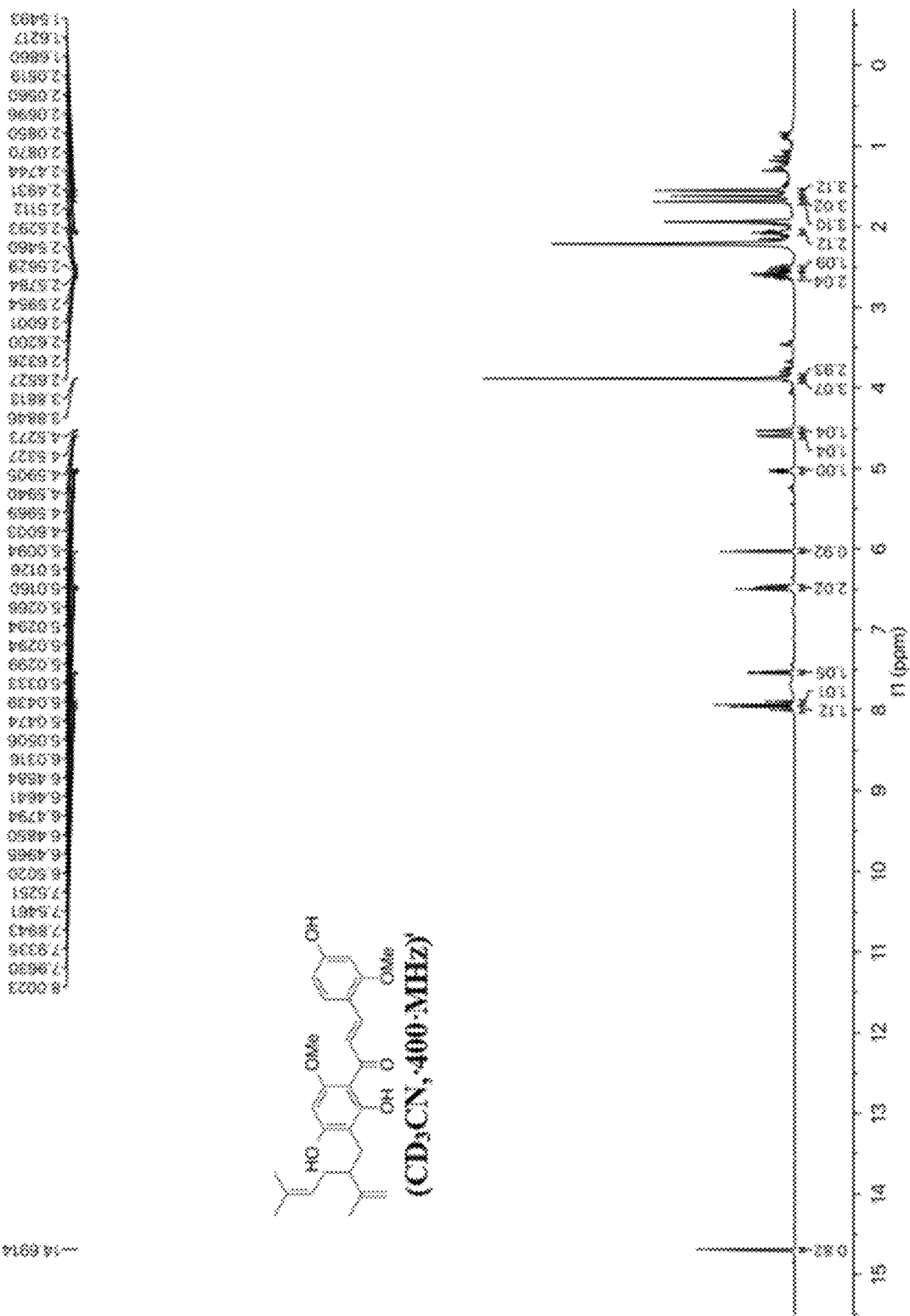
Figure 32:
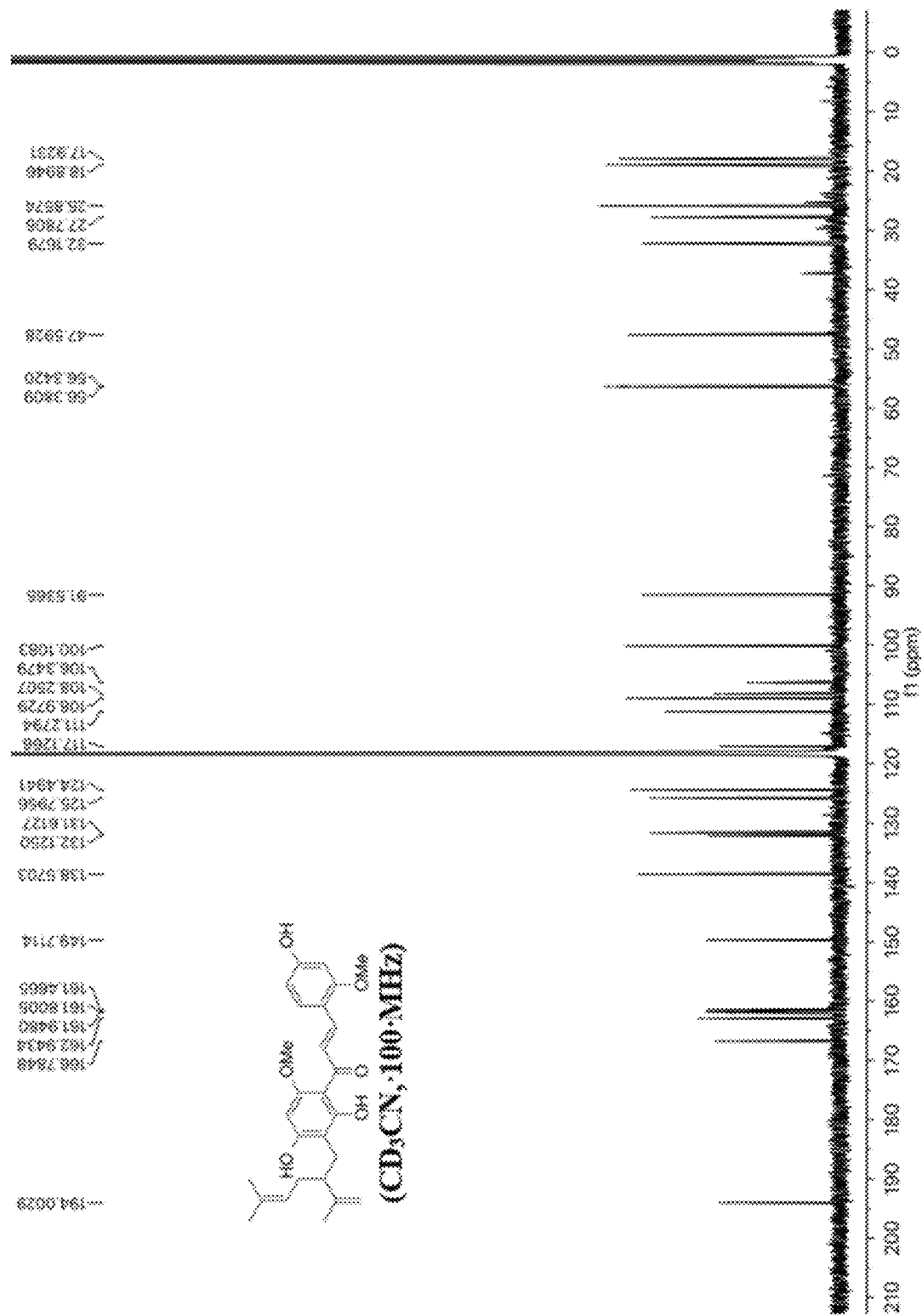

Simulation of Predicted Molecular Interactions of Natural Compounds on Targets of S. aureus Table 6 shows results of docking studies on the interaction of baicalein, berberine analogue, ECG, and kuraridin with Sortase A, expressed as free-binding energies (ΔG). The docking results of the CHARMM energies were estimated by Swiss Dock software and expressed as ΔG (kcal/mol). The three-dimensional crystal structure of Staphylococcus aureus Sortase A in Complex with a LPETG peptide (PDB ID: 1T2W) was retrieved from the Protein Databank Bank (website: www.rcsb.org). Docking was performed using default parameters and blind docking approach (no region of interest defined). Kuraridin had the maximum binding affinity to Sortase A. For berberine, an analogue of berberine (BA) was created for the docking study. FIG. 15 provides visualization of the most energetically favorable binding mode of the ligands baicalein (1a), berberine (1b), epicatechin gallate (1c) and kuraridin (1d) into Sortase A. Anti-adherence activity of natural compounds was also studied. FIG. 16 shows fibrinogen-binding adherence of MRSA strain JE-2 and its isogenic mutant ΔsrtA with baicalein, berberine, ECG and kuraridin. FIG. 17 shows adherence and internalization of S. aureus by HaCaT keratinocytes. FIG. 18 provides results of microscopic examination of adherence of S. aureus to Hacat keratinocytes by Giemsa staining, with and without treatment with baicalein. FIG. 19 shows results of microscopic examination of adherence of S. aureus to Hacat keratinocytes by Giemsa staining, with and without treatment with ECG. FIG. 20 shows results of microscopic examination of adherence of S. aureus to Hacat keratinocytes by Giemsa staining, with and without treatment with kuraridin. FIG. 21 shows bacterial aggregation of MRSA JE-2 and its isogenic ΔSrtA under varying concentrations of baicalein (a), berberine (b), ECG (c) and kuraridin (d).

Mechanisms of Action of ECG and Kuraridin, ECG and Kuraridin Derivatives Against MRSA Anti-Adherence Activity of ECG and Kuraridin-Fibrinogen-Bindin Gadherence Assay and Crystal Violet Assay Overnight cultures of MRSAJE-2 and its isogenic mutant ΔsrtA will be diluted 1:100 into fresh TSB, inhibitors are added at variable concentration, and cultures was grown at 37° C. to A600 reaching to 0.5. Every 0.5 h for 2.5 h following the A600 reaching 0.5, 800-μL cell suspensions were removed and sedimented by centrifugation (12,000×g for 5 min). Cells suspended in 200 μL PBS was added to the wells of fibrinogen-coated 96-well microtiter plates and incubated for 2 h at 37° C. Liquid was removed, wells were washed twice with 200 μL PBS, and samples were fixed with 100 pt 4% (vol/vol) glutaraldehyde. ECG and kuraridin, and in combination give final concentrations of 1, 10, and 100 μg/ml were added to the well. Staphylococci bound to fibrinogen was stained for 1 h with 100 μL Crystal Violet (CV) (Difco, Augsburg, Germany), and wells were washed extensively with PBS. Plates will then be dried and 200 pt extraction solutions (10% acetic acid) will be added to each well and incubated for 10 min on an orbital shaker. The absorbance at 570 nm was subsequently be measured. Triplicate measurements were taken for each data point p-hydroxymecuribenzoic acid (pHMB), which is a known sortase A inhibitor was used as positive control.

Bacterial Adherence to HaCa-T Keratinocytes

HaCa-T keratinocytes were washed with PBS, and adjusted to $10^4$ cells/ml. MRSA JE-2 and its isogenic mutant ΔsrtA was washed with PBS and adjusted to $10^8$ cells/ml. Equal volumes (2 ml) of bacterial cells and Haca T keratinocytes were mixed and incubated at 37° C. for 2 h with occasional shaking. The unbound bacteria was removed with 6% dextran. Finally, the samples containing HaCa T keratinocytes and bound bacteria was resuspended in 100 μl PBS, and 20-μl samples was applied to microscope slides. After Gram staining, the number of bacteria per 100 nasal epithelial cells was determined. To test for reproducibility, three batches of cells were tested in the assay. For blocking experiments, HaCa T keratinocytes ($10^4$ cells/ml) was pre-incubated with ECG and kuraridin alone, and in combination give final concentrations of 1, 10, and 100 μg/ml. ECG and kuraridin, and in combination give final concentrations of 1, 10, and 100 μg/ml. HaCa T keratinocytes were be pre-incubated for 30 min at 37° C. Bacterial cells were incubated with the treated HaCa T keratinocytes for 2 h at 37° C. with occasional shaking and the adherence assay was continued as described above. Blocking experiments were performed in triplicate p-hydroxymecuribenzoic acid (pHMB), which is a known sortase A inhibitor was used as positive control.

Aggregation Assay of MRSA JE-2 and its Isogenic ΔSrtA

Overnight culture of MRSA JE-2 or its isogenic ΔSrtA aggregation were grown in glass test tubes under constant agitation at 200 r.p.m. until OD600 of 0.9 was reached. Subsequently, the suspension was incubated in the presence of ECG and kuraridin, and in combination (final concentrations of 1, 10, and 100 μg/ml) at room temperature without shaking and the OD600 of the suspensions close to the liquidair interface were measured at 30 min intervals p-hydroxymecuribenzoic acid (pHMB), which is a known sortase A inhibitor was as positive control.

Anti-Adherence Activity of Natural Compounds

Docking studies predicted that the compounds bind to the active site of the Sortase A protein which inhibits the activity of SrtA transpeptidase. SrtA catalyses the covalent anchoring of surface proteins, e.g., fibrinogen-binding protein, to the cell wall of S. aureus. S. aureus mutants that lack a functional srtA will be defective in the establishment of infection as they will be unable to display surface proteins. Thus, these compounds would attenuate the virulence of S. aureus by inhibiting the activity of SrtA, such as interfering in fibrinogen (Fg) binding.

Evaluation of Adhesion by Giemsa Stain

HaCaT cells were cultured in Nunc Lab-Tek Chamber Slide system with DMEM supplemented with 10% FBS at 37° C., 5% $CO_2$ for 24 hrs until confluence (around $5 \times 10^5$ cells per well). Adhesion assay was performed with MRSA wild type JE-2 and isogenic mutant ΔsrtA. Slides were fixed in methanol and stained with 10% Giemsa stain.

Discussion

The current study has demonstrated that the combined use of ECG and kuraridin was efficacious in inhibiting the growth of a panel of tested MRSA strains in vitro. Kuraridin and ECG are both non-cytotoxic and possess anti-inflammatory activities. By using specific strains, the antibacterial activities of gentamicin, fusidic acid and vancomycin could be further enhanced additively by the addition of ECG and kuraridin in vitro. Time-kill studies showed that the antibacterial activities of vancomycin with ECG and kuraridin were bactericidal and the combination was better than vancomycin or ECG/kuraridin when used alone. The dosage of vancomycin could be reduced to therapeutically relevant concentrations (nanograms level). Vancomycin was associated with many side effects including vestibular and renal toxicity (26). Apart from their direct use, kuraridin and ECG may be a good choice to supplement with sub-optimal dosage of vancomycin to prevent its side effects and drug resistance in MRSA treatment. While ECG and kuraridin have not been shown to enhance vancomycin in the animal testing, it may very well be due to the fact that their concentrations were not high enough, especially at the site of infection. In this regard, the mouse pneumonia model may not be the best model for evaluating the antibacterial effects of the current study. Certain other animal models such as skin and wound infection models may be useful in further evaluating in vivo efficacy of ECG and kuraridin.

Another possibility that ECG and kuraridin have not been shown to enhance vancomycin in vivo may relate to bioavailability. Green tea extract alone or in combination with amoxicillin has been shown to weaken the antibacterial effect of amoxicillin in MRSA infected mice and tea drinking is not recommended in combination with amoxicillin treatment in one study (27). In that study (27), mice were intraperitoneally infected with MRSA. Amoxicillin and green tea extract were then administered via gastric perfusion. It was discovered that MIC of amoxicillin was greatly increased in the presence of 0.25% tea extract.

Apart from animal testing, green tea catechin and soy isoflavones administrations have also been shown to reduce the bioavailability of statins in human (29). In two open-label, single-dose, three-phase clinical pharmacokinetic studies, healthy Chinese male subjects were given a single dose of rosuvastatin 10 mg (Study A) or simvastatin 20 mg (Study B) on 3 occasions: 1. without herbs; 2. with green tea extract; 3. with soy isoflavone extract. In study A (n=20), intake of green tea extract significantly reduced the systemic exposure to rosuvastatin by nearly one third. In study B (n=18), intake of soy isoflavones was associated with reduced systemic exposure to simvastatin acid. Taken together, these study suggest that repeated green tea catechin or soy isoflavones administration can reduce the bioavailability of statins in healthy volunteers and these effects might be predicted to reduce the beneficial action of the drugs (28). In the current study, ECG or kuraridin at the tested concentrations did not significantly enhance or decrease the efficacy of vancomycin. ECG and kuraridin are natural flavonoids that may affect the bioavailability of vancomycin and hence the expected synergistic antibacterial activities were not observed.

ECG has been shown to possess a high affinity for the positively charged Staphylococcal membrane and induced changes to the biophysical properties of the bilayer that are likely to account for its capacity to disperse the cell wall biosynthetic machinery responsible for 0-lactam resistance (29). For kuraridin, the inhibitory mechanism against MRSA was not yet known, but different studies showed that kuraridin could inhibit a wide array of enzymes activities, namely protein tyrosine phosphatase 1B (30), beta-site APP cleaving enzyme 1 (BACE1 and cholinesterases (31), aldose reductase (32), tyrosinase and melanin synthesis (32), glycosidase (33), diacylglycerol acyltransferase (34) and tyrosinase (35). The antibacterial activites of kuraridin may involve inhibiting some key enzymes in MRSA for its survival. Further studies are required to investigate this issue. Ser/Thr phosphorylation/dephosphorylation is a common theme in regulation of cellular functions determining metabolic activity and virulence also in the major human pathogen *S. aureus* (36).

Apart from MRSA treatment, the combined use of Radix Sophorae Flavescentis and green tea extracts has been recently applied to the treatment of genital warts (37).

In conclusion, the present study reports for the first time that the combined use of ECG and kuraridin can enhance the anti-bacterial activities of gentamicin, fusidic acid, and vancomycin against MRSA in vitro. In mouse pneumonia infection model, the combined use of ECG and kuraridin slightly reduced bacterial counts in MRSA-infected mice. The success in MRSA treatment provides proof of concept that kuraridin and ECG combined treatment can be used in treating other bacterial drug resistance.

Example 2: Combination Treatment Using Kuraridin Analogs

Introduction

Resistance to antimicrobials such as methicillin resistant *Staphylococcus aureus* (MRSA) is a significant and growing problem, as treatment options are limited. The present inventors developed an efficacious non-toxic herbal and antibiotics combination for MRSA treatment with antibacterial and anti-inflammatory activities. In addition to the observations described in Example 1, further antibacterial testing was carried with synthetic kuraridin and its analogues. In order to study these compounds, kuraridin and eight of its analogues were newly synthesized, characterized, and further subject to antibacterial and toxicity testing. In this study, the inventors (1) used a panel of MRSA strains to work out the best combination from new synthesized kuraridin and eight analogues with conventionally used antibiotics (macrolides, vancomycin and/or aminoglycosides) against MRSA; (2) used human peripheral blood mononuclear cells and cultured macrophages to evaluate the anti-inflammatory activities of these compounds alone and in combination; (3) synthesized kuraridin and its analogues through synthetic pathway developed; and (4) characterized, for example, generated mass spectroscopies data of the new compounds.

This study demonstrates that the combined use of synthetic kuraridin and its analogues is efficacious in inhibiting the growth of a panel of tested MRSA strains in vitro. The antibacterial activities of ECG can be further enhanced by the addition of kuraridin or its analogues WQD175 and WQD165. Kuraridin and its analogues are generally non-cytotoxic. Synthetic pathways of kuraridin, its analogues and characterization of the compounds are also described.

Material and Methods

See description in Example 1.

Results

Minimal Inhibitory Concentrations of Kuraridin and Analogues Ranged 4-128 μg/ml

The list of kuraridin analogues synthesized are listed in Table 7. The minimum inhibitory concentrations (MICS) were defined as the lowest concentration of antibacterial, which resulted in either ≥99.9% inhibition of growth compared with that of the drug-free control. Table 8 lists the activities of synthesized kuraridin and analogues.

Combination of ECG and Kuraridin or its Analogues Inhibits MRSA Growth

The effects of combinations were evaluated by calculating the Fractional Inhibitory Concentration Index (FICI) for each combination using the following formula: FIC of drug A=MIC of drug A in combination/MIC of drug A alone; FIC of drug B=MIC of drug B in combination/MIC of drug B alone; hence FICI=FIC of drug A+FIC of drug B. Off-scale MICS were converted to the next highest or next lowest doubling concentration. "Synergy" was defined when FIC index was less than or equal to 0.5; while "additive" in which the FIC index was greater than 0.5 and less than or equal to 1.0; whereas "indifferent" when the FIC index was greater than 1.0 and less than or equal to 2.0; and "antagonistic" in cases which the FIC index was greater than 2.0.

Table 8 lists the activities of the active compounds and their FIC and FICI.

Kuraridin and its Analogues are Non-Toxic to Human Peripheral Mononuclear Cells (PBMCs)

The cytotoxicity of kuraridin and its analogues were determined by the sodium 3'-[1-(phenylaminocarbonyl)-3,4-tetrazolium]-bis (4-methoxy-6-nitro) benzene sulfonic acid hydrate (XTT) assay.

Cells were plated in 96-well plates at $10^5$ cells/well. Serial dilutions of the compounds ranging 2-64 µg/ml were incubated with PBMCs at 37° C. for 72 hrs. 50 µl of XTT/PMS solution (20 µM) were added to each well, and the plates further incubated at 37° C. for 4 h. The OD of the wells was determined by a spectrophotometer at 450 nm. The toxicity represents the ratio of OD of a well in the presence of compounds with the OD of control wells in the presence of medium containing DMSO. The cellular viability of at least 85% was considered to indicate a non-toxic compound.

Synthesis of Kuraridin and its Analogues: Synthetic Sequences and Characterization Methyl 2,6-dihydroxy-4-methoxybenzoate and methyl 2-hydroxy-4,6-dimethoxybenzoate

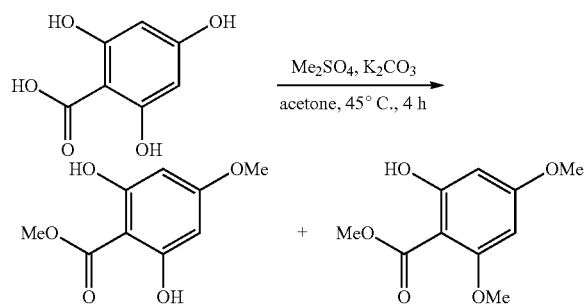

To a solution of 2,4,6-trihydroxybenzoic acid hydrate (10.2 g, 54.2 mmol), $K_2CO_3$ (16.4 g, 119.3 mmol) in acetone (300 mL) at 45° C. was added $Me_2SO_4$ (9.7 mL, 103 mmol). The reaction mixture was stirred for 3.5 h and water (120 mL) was added subsequently. The reaction mixture was stirred for another 30 min and then extracted with EtOAc, and the separated organic layer was evaporated to dryness. The crude product was purified by column chromatography on silica gel (0% to 2% EtOAc in hexanes) to afford a mixture of methyl 2,6-dihydroxy-4-methoxybenzoate and methyl 2-hydroxy-4,6-dimethoxybenzoate (8.9 g, 71% yield, 6:1 ratio) as a white solid, $R_f$=0.59 (silica gel, hexane:EtOAc=2:1). $^1$H NMR (500 MHz, $CDCl_3$): δ 6.03 (s, 2H), 4.03 (s, 3H), 3.79 (s, 3H) ppm; $^{13}$C NMR (125 MHz, $CDCl_3$): δ 169.8, 166.6, 162.6 (br), 94.6, 94.1, 55.6, 52.6 ppm; HRMS m/z (ESI) calcd. for $C_8H_5O_4$ [M-$CH_3OH$-H]$^-$: 165.0193; found: 165.0192; $C_9H_9O_5$ [M-H]$^-$: 197.0456; found: 197.0456.

Methyl 2,6-bis(benzyloxy)-4-methoxybenzoate

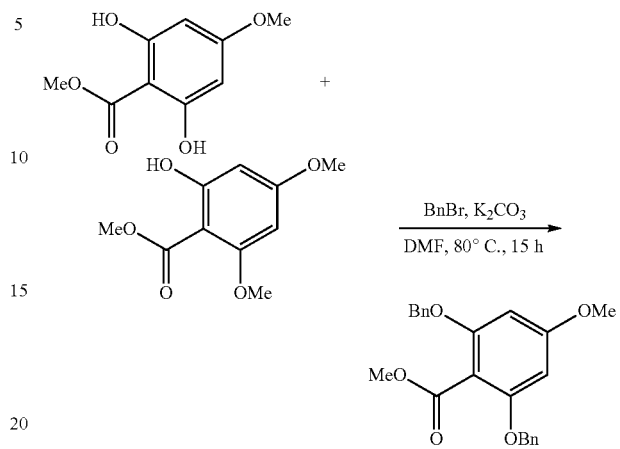

To a mixture of methyl 2,6-dihydroxy-4-methoxybenzoate and methyl 2-hydroxy-4,6-dimethoxybenzoate (6:1 ratio) (8.7 g, 44 mmol) and $K_2CO_3$ (36.4 g, 263 mmol) in anhydrous DMF (100 mL) at 80° C. was added BnBr (21 mL, 175.6 mmol). The reaction mixture was stirred at this temperature for 15 h. Water was added to the mixture and the aqueous layer was extracted with diethyl ether, the separated organic layer was evaporated to dryness. The crude product was purified by column chromatography on silica gel (0% to 3% EtOAc and 3% DCM in hexanes) to afford methyl 2,6-bis(benzyloxy)-4-methoxybenzoate (10.3 g, 71% yield) as a white solid, $R_f$=0.35 (silica gel, hexane:EtOAc=4:1). $^1$H NMR (500 MHz, $CDCl_3$): δ 7.40-7.28 (m, 10H), 6.14 (s, 2H), 5.10 (s, 4H), 3.87 (s, 3H), 3.73 (s, 3H) ppm; $^{13}$C NMR (500 MHz, $CDCl_3$): δ 166.9, 162.4, 157.8, 136.8, 128.6, 128.0, 127.0, 107.4, 92.7, 70.7, 55.6, 52.3 ppm; HRMS m/z (ESI) calcd. for $C_{23}H_{22}O_5Na$ [M+Na]$^+$: 401.1359; found: 401.1359.

(2,6-Bis(benzyloxy)-4-methoxyphenyl)methanol

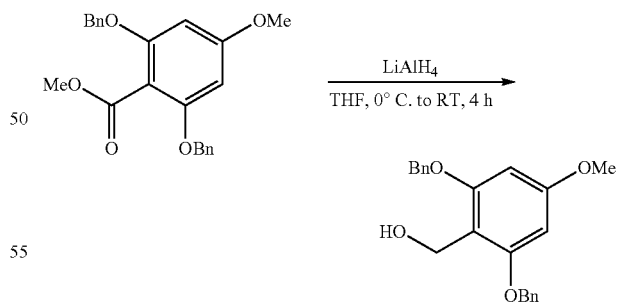

To a solution of methyl 2,6-bis(benzyloxy)-4-methoxybenzoate (10.3 g, 27.2 mmol) in anhydrous THF (200 mL) was added LiAlH$_4$ (3.1 g, 81.7 mmol) in portions at 0° C. The reaction was then slowly warmed to room temperature. After stirring for 4 h, the mixture was cooled to 0° C., and aq. sat. $Na_2SO_4$ solution was added slowly. The suspension was then filtered by filtration through a pad of celite and washed with anhydrous THF. The filtrate was concentrated in vacuo and the resulting crude was purified by column chromatography on silica gel (0% to 15% EtOAc in hexanes) to afford (2,6-bis(benzyloxy)-4-methoxyphenyl) methanol (8.0 g, 84% yield) as a white solid, $R_f$=0.21 (silica gel, hexane:EtOAc=4:1). $^1$H NMR (500 MHz, CDCl$_3$): δ 7.44-7.38 (m, 8H), 7.35-7.32 (m, 2H), 6.22 (s, 2H), 5.09 (s, 4H), 4.81 (d, J=6.7 Hz, 2H), 3.77 (s, 3H), 2.30 (t, J=6.7 Hz, 1H) ppm; $^{13}$C NMR (125 MHz, CDCl$_3$): δ 161.0, 158.5, 136.9, 128.8, 128.2, 127.4, 111.1, 92.4, 70.7, 55.5, 54.9 ppm; HRMS m/z (ESI) calcd. for C$_{22}$H$_{22}$O$_4$Na [M+Na]$^+$: 373.1410; found: 373.1411.

2,6-Bis(benzyloxy)-4-methoxybenzaldehyde

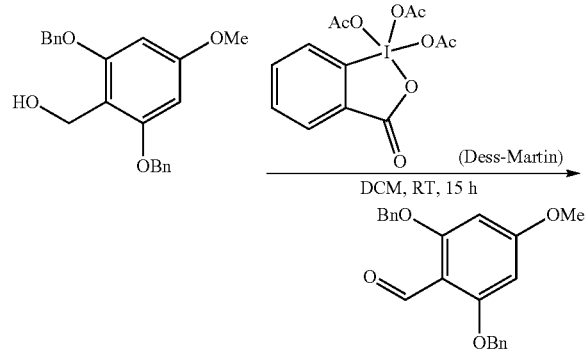

To a solution of (2,6-bis(benzyloxy)-4-methoxyphenyl) methanol (2.0 g, 5.7 mmol) in DCM (50 mL) was added Dess-Martin reagent (4.8 g, 11.4 mmol) in portions at 0° C. The reaction mixture was then slowly warmed to room temperature and stirred for 15 h. The mixture was concentrated in vacuo and the resulting crude product was purified by column chromatography on silica gel (0% to 10% EtOAc in hexanes) to give 2,6-bis(benzyloxy)-4-methoxybenzaldehyde (1.0 g, 50% yield) as a white solid. $R_f$=0.21 (silica gel, hexane:EtOAc=4:1). $^1$H NMR (500 MHz, CDCl$_3$): δ 10.51 (s, 1H), 7.49-7.47 (m, 4H), 7.41-7.38 (m, 4H), 7.34-7.30 (m, 2H), 6.14 (s, 2H), 5.17 (s, 4H), 3.79 (s, 3H) ppm; $^{13}$C NMR (125 MHz, CDCl$_3$): δ 187.6, 165.9, 163.1, 136.3, 128.8, 128.1, 127.1, 109.8, 92.3, 70.8, 55.6 ppm; HRMS m/z (ESI) calcd. for C$_{22}$H$_{20}$O$_4$Na [M+Na]$^+$:371.1254; found: 371.1253.

Methyl (E)-3-(2,6-bis(benzyloxy)-4-methoxyphenyl) acrylate

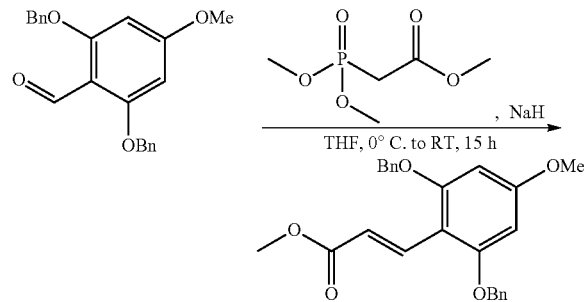

To a suspension of NaH (689 mg of a 60% dispersion in mineral oil, 17.2 mmol) in anhydrous THF (40 mL) was added trimethyl phosphonoacetate (2.6 mL, 15.8 mmol) at 0° C. After stirring for 1 h, a solution of 2,6-bis(benzyloxy)-4-methoxybenzaldehyde (5.0 g, 14.4 mmol) in THF (10 mL) was added subsequently. The reaction mixture was then warmed to room temperature and stirred for 15 h. Water was added to the mixture to quench the reaction and the aqueous layer was extracted with EtOAc. The separated organic layer was evaporated to dryness. The crude product was purified by column chromatography on silica gel (0% to 5% EtOAc in hexanes) to give methyl (E)-3-(2,6-bis(benzyloxy)-4-methoxyphenyl)acrylate (5.3 g, 91% yield) as a white solid, $R_f$=0.33 (silica gel, hexane:EtOAc=4:1). $^1$H NMR (400 MHz, CDCl$_3$): δ 8.23 (d, J=16.2 Hz, 1H), 7.45-7.37 (m, 8H), 7.35-7.31 (m, 2H), 6.84 (d, J=16.3 Hz, 1H), 6.15 (s, 2H), 5.16 (s, 4H), 3.75 (s, 3H), 3.73 (s, 3H) ppm; $^{13}$C NMR (125 MHz, CDCl$_3$): δ 169.5, 162.5, 160.3, 136.6, 135.7, 128.8, 128.2, 127.3, 117.9, 106.8, 92.4, 70.8, 55.4, 51.4 ppm; HRMS m/z (ESI) calcd. for C$_{25}$H$_{24}$O$_5$Na [M+Na]$^+$: 427.1516; found: 427.1517.

Methyl 3-(2,6-dihydroxy-4-methoxyphenyl)propanoate

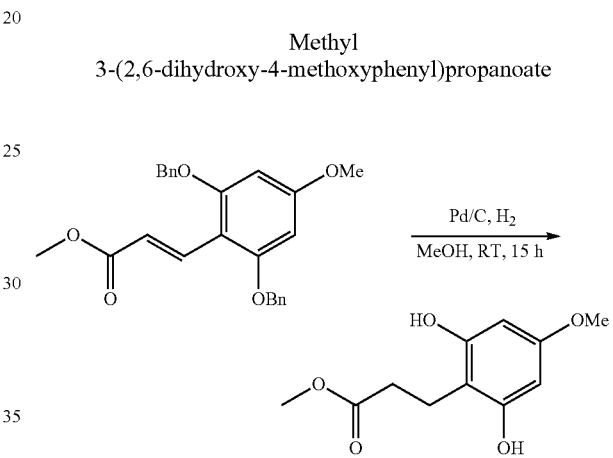

A solution of methyl (E)-3-(2,6-bis(benzyloxy)-4-methoxyphenyl)acrylate (4.6 g, 11.4 mmol) and 10% Pd on carbon (wetted with ca. 55% water) (242 mg, 22.7 mmol) in MeOH (50 mL) was stirred at room temperature under H$_2$ balloon. After stirring for 15 h, the reaction mixture was filtered through a pad of celite. The filtrate was concentrated in vacuo and the resulting crude product was purified by column chromatography on silica gel (0% to 35% EtOAc in hexanes) to give methyl 3-(2,6-dihydroxy-4-methoxyphenyl)propanoate (2.6 g, quant. yield) as a light yellow oil, $R_f$=0.30 (silica gel, hexane:EtOAc=2:1). $^1$H NMR (500 MHz, CDCl$_3$): δ 6.84 (br s, 2H), 6.06 (s, 2H), 3.70 (s, 3H), 3.69 (s, 3H), 2.84-2.82 (m, 2H), 2.73-2.71 (m, 2H) ppm; $^{13}$C NMR (125 MHz, CDCl$_3$): δ 177.9, 159.6, 156.0, 107.6, 95.3, 55.3, 52.6, 33.7, 17.8 ppm; HRMS m/z (ESI) calcd. for C$_{11}$H$_{14}$O$_5$Na [M+Na]$^+$: 249.0733; found: 249.0734.

Methyl 3-(4-methoxy-2,6-bis(methoxymethoxy) phenyl)propanoate

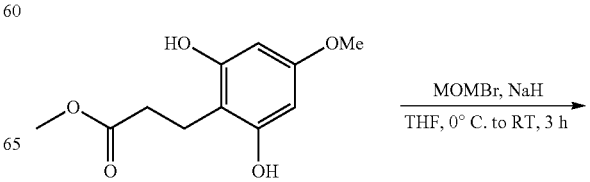

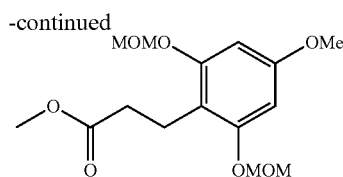

To a solution of methyl 3-(2,6-dihydroxy-4-methoxyphenyl)propanoate (2.6 g, 11.5 mmol) in anhydrous THF (50 mL) at 0° C. was added NaH (1.8 g of a 60% dispersion in mineral oil, 46.0 mmol) and MOMBr (2.8 mL, 34.5 mmol) successively. After stirring at room temperature for 3 h, the reaction mixture was quenched with water and extracted with EtOAc. The separated organic layer was evaporated to dryness and the resulting crude product was purified by column chromatography on silica gel (0% to 10% EtOAc in hexanes) to give methyl 3-(4-methoxy-2,6-bis(methoxymethoxy)phenyl)propanoate (2.05 g, 57% yield) as a light yellow oil, $R_f$=0.54 (silica gel, hexane:EtOAc=2:1). $^1$H NMR (500 MHz, CDCl$_3$): δ 6.38 (s, 2H), 5.16 (s, 4H), 3.76 (s, 3H), 3.68 (s, 3H), 3.47 (s, 3H), 2.94 (d, J=8.0 Hz, 2H), 2.49 (t, J=8.4 Hz, 2H) ppm; $^{13}$C NMR (125 MHz, CDCl$_3$): δ 174.3, 159.6, 156.6, 111.1, 94.7, 94.6, 56.2, 55.5, 51.6, 34.0, 18.9 ppm; HRMS m/z (ESI) calcd. for $C_{15}H_{22}O_7Na$ [M+Na]$^+$: 337.1258; found: 337.1255.

Methyl 2-(4-methoxy-2,6-bis(methoxymethoxy)benzyl)-5-methylhex-4-enoate

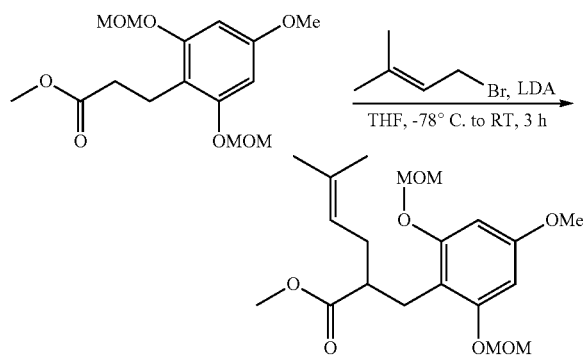

LDA solution (2 M) preparation: n-butyllithium (2.4 mL, 1.6 M solution in hexanes, 3.82 mmol) was added to a solution of freshly distilled diisopropylamine (0.59 mL, 4.2 mmol) in anhydrous THF (1.9 mL) at −78° C. under argon atmosphere. The reaction mixture was then slowly warmed to room temperature and continued stirring for 1 h. A solution of methyl 3-(4-methoxy-2,6-bis(methoxymethoxy)phenyl)propanoate (800 mg, 2.55 mmol) in anhydrous THF (10 mL) was added dropwise to the freshly prepared LDA solution at −78° C. under an argon atmosphere. The mixture was then stirred at −78° C. for 30 min. Prenyl bromide (0.35 mL, 3.05 mmol) was added at −78° C., then the reaction mixture was gradually warmed to room temperature and stirred for 3 h. The reaction mixture was quenched with aq. sat. NH$_4$Cl solution and extracted with EtOAc. The combined organic layers were evaporated in vacuo, and the resulting crude product was purified by column chromatography on silica gel (0% to 3% EtOAc in hexanes) to afford methyl 2-(4-methoxy-2,6-bis(methoxymethoxy)benzyl)-5-methylhex-4-enoate (602 mg, 62% yield) as a yellow oil, $R_f$=0.63 (silica gel, hexane:EtOAc=2:1). $^1$H NMR (500 MHz, CDCl$_3$): δ 6.38 (s, 2H), 5.14 (s, 4H), 5.09-5.06 (m, 1H), 3.76 (s, 3H), 3.59 (s, 3H), 3.47 (s, 6H), 2.93-2.82 (m, 2H), 2.70-2.67 (m, 1H), 2.33-2.30 (m, 1H), 2.15-2.12 (m, 1H), 1.65 (s, 3H), 1.55 (s, 3H) ppm; $^{13}$C NMR (125 MHz, CDCl$_3$): δ 176.6, 159.6, 156.9, 133.3, 121.9, 110.1, 94.7, 94.4, 56.2, 55.5, 51.4, 45.9, 30.4, 25.9, 25.8, 17.8 ppm; HRMS m/z (ESI) calcd. for $C_{20}H_{30}O_7Na$ [M+Na]$^+$: 405.1884; found: 405.1884.

N-methoxy-2-(4-methoxy-2,6-bis(methoxymethoxy)benzyl)-N,5-dimethylhex-4-enamide

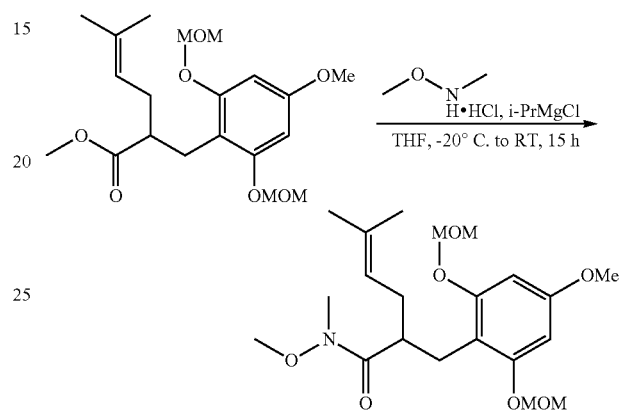

i-PrMgCl (2.6 mL, 2 M solution in THF, 5.1 mmol) was added to a solution of methyl 2-(4-methoxy-2,6-bis(methoxymethoxy)benzyl)-5-methylhex-4-enoate (650 mg, 1.7 mmol) and N,O-dimethylhydroxylamine hydrochloride (249 mg, 2.5 mmol) in anhydrous THF (10 mL) at −20° C. under an argon atmosphere. The reaction mixture was then warmed to room temperature and continued stirring for 15 h. Aq. sat. NH$_4$Cl solution was added to the mixture and the aqueous solution was extracted with EtOAc. The combined organic layers were evaporated to dryness and the resulting crude was purified by column chromatography on silica gel (0% to 20% EtOAc in hexanes) to give N-methoxy-2-(4-methoxy-2,6-bis(methoxymethoxy)benzyl)-N,5-dimethylhex-4-enamide (600 mg, 86% yield) as a yellow oil, $R_f$=0.29 (silica gel, hexane:EtOAc=2:1). $^1$H NMR (500 MHz, CDCl$_3$): δ 6.39 (s, 2H), 5.15 (s, 4H), 5.08-5.04 (m, 1H), 3.76 (s, 3H), 3.48 (s, 9H), 3.12 (s, 3H), 2.86 (d, J=7.3 Hz, 2H), 2.40-2.34 (m, 1H), 2.11-2.05 (m, 1H), 1.76-1.66 (m, 1H), 1.63 (s, 3H), 1.54 (s, 3H) ppm; $^{13}$C NMR (125 MHz, CDCl$_3$): δ 177.7, 159.5, 157.1, 132.9, 122.5, 110.8, 94.8, 94.5, 61.3, 56.2, 55.5, 41.0, 32.2, 30.4, 26.1, 25.9, 17.9 ppm; HRMS m/z (ESI) calcd. for $C_{21}H_{33}O_7Na$ [M+Na]$^+$: 434.2149; found: 434.2149.

3-(4-Methoxy-2,6-bis(methoxymethoxy)benzyl)-6-methylhept-5-en-2-one

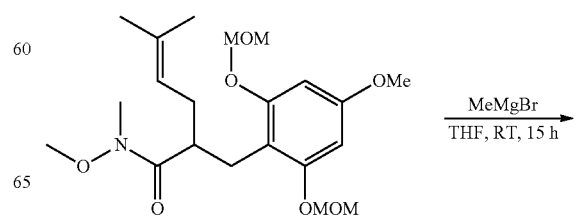

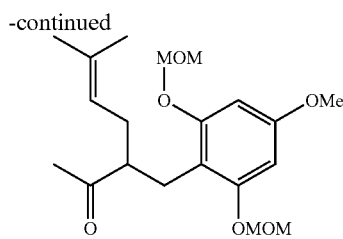

MeMgBr (1.1 mL, 3 M solution in 2-methyl-THF, 3.3 mmol) was added dropwise to a solution of N-methoxy-2-(4-methoxy-2,6-bis(methoxymethoxy)benzyl)-N,5-dimethylhex-4-enamide (1.12 g, 2.7 mmol) in anhydrous THF (10 mL) at −78° C. under argon atmosphere. The reaction was then stirred at room temperature for 15 h. The mixture was quenched with aq. sat. NH$_4$Cl solution and extracted with EtOAc. The separated organic layers were evaporated to dryness and the resulting crude was purified by column chromatography on silica gel (0% to 5% EtOAc in hexanes) to give 3-(4-methoxy-2,6-bis(methoxymethoxy)benzyl)-6-methylhept-5-en-2-one (927 mg, 93% yield) as a yellow oil, R$_f$=0.67 (silica gel, hexane:EtOAc=2:1). $^1$H NMR (500 MHz, CDCl$_3$): δ 6.38 (s, 2H), 5.15 (s, 4H), 5.05-5.02 (m, 1H), 3.76 (s, 3H), 3.47 (s, 6H), 2.84-2.74 (m, 3H), 2.34-2.28 (m, 1H), 2.14-2.09 (m, 1H), 2.04 (s, 3H), 1.65 (s, 3H), 1.56 (s, 3H) ppm; $^{13}$C NMR (125 MHz, CDCl$_3$): δ 213.0, 159.6, 156.8, 133.1, 122.1, 110.2, 94.7, 94.4, 56.2, 55.5, 53.3, 30.0, 29.8, 25.9, 25.6, 17.9 ppm; HRMS m/z (ESI) calcd. for C$_{20}$H$_{30}$O$_6$Na [M+Na]$^+$: 389.1935; found: 389.1935.

5-Methoxy-1,3-bis(methoxymethoxy)-2-(5-methyl-2-(prop-1-en-2-yl)hex-4-en-1-yl)benzene

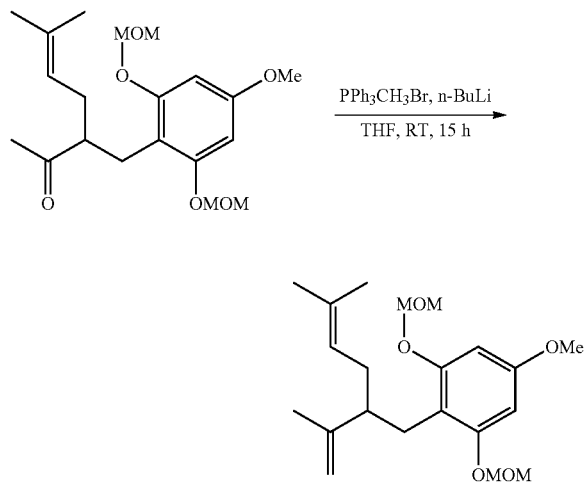

n-BuLi (2.5 mL, 1.6 M solution in hexanes, 4.0 mmol) was added to a suspension of PPh$_3$CH$_3$Br (1.38 g, 3.88 mmol) in anhydrous THF (8 mL) at room temperature. After stirring for 1 h, a solution of 3-(4-methoxy-2,6-bis(methoxymethoxy)benzyl)-6-methylhept-5-en-2-one (710 mg, 1.9 mmol) in THF (2 mL) was added and the reaction mixture was stirred at room temperature for 15 h. Water was added to the mixture and extracted with EtOAc, the combined organic layer was evaporated to dryness. The resulting crude product was purified by column chromatography on silica gel (0% to 1.5% EtOAc in hexanes) to afford 5-methoxy-1,3-bis(methoxymethoxy)-2-(5-methyl-2-(prop-1-en-2-yl)hex-4-en-1-yl)benzene (560 mg, 79% yield) as a clear oil, R$_f$=0.69 (silica gel, hexane:EtOAc=4:1). $^1$H NMR (500 MHz, CDCl$_3$): δ 6.38 (s, 2H), 5.08-5.05 (m, 1H), 4.62-4.61 (m, 1H), 4.51 (d, J=1.9 Hz, 1H), 3.76 (s, 3H), 3.48 (s, 6H), 2.69-2.63 (m, 2H), 2.42-2.36 (m, 1H), 2.12-2.02 (m, 2H), 1.71 (s, 3H), 1.66 (s, 3H), 1.56 (s, 3H) ppm; $^{13}$C NMR (125 MHz, CDCl$_3$): δ 159.1, 156.9, 148.5, 131.4, 123.8, 112.1, 110.7, 94.8, 94.4, 56.1, 55.4, 48.0, 31.5, 27.8, 25.9, 18.9, 18.0 ppm; HRMS m/z (ESI) calcd. for C$_{21}$H$_{32}$O$_5$Na [M+Na]$^+$: 387.2142; found: 387.2142.

1-(6-Methoxy-2,4-bis(methoxymethoxy)-3-(5-methyl-2-(prop-1-en-2-yl)hex-4-en-1-yl)phenyl)ethan-1-ol

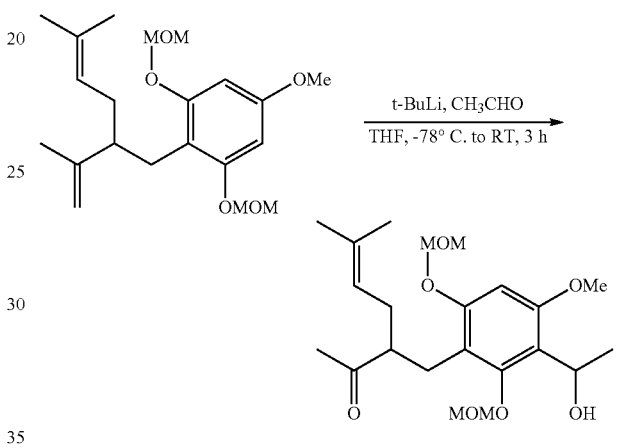

t-BuLi (1 mL, 1.3 M solution in pentane, 1.3 mmol) was added to a solution of 5-methoxy-1,3-bis(methoxymethoxy)-2-(5-methyl-2-(prop-1-en-2-yl)hex-4-en-1-yl)benzene (316 mg, 0.87 mmol) in anhydrous THF (10 mL) at −78° C. under an argon atmosphere. After stirring at room temperature for 1 h, CH$_3$CHO (2 mL) was added to the reaction mixture at −78° C. to quench the reaction, and continued stirring at room temperature for 2 h. Then, water was added and the aq. layer was extracted with EtOAc, the combined organic layer was evaporated to dryness. The resulting crude product was purified by column chromatography on silica gel (0% to 10% EtOAc in hexanes) to give 1-(6-methoxy-2,4-bis(methoxymethoxy)-3-(5-methyl-2-(prop-1-en-2-yl)hex-4-en-1-yl)phenyl)ethan-1-ol (283 mg, 80% yield) as a yellow oil, R$_f$=0.23 (silica gel, hexane:EtOAc=4:1). $^1$H NMR (500 MHz, CDCl$_3$): δ 6.58 (s, 1H), 5.13 (s, 3H), 5.05-5.01 (m, 1H), 4.96-4.95 (m, 1H), 4.90-4.87 (m, 1H), 4.62-4.60 (m, 1H), 4.50 (t, J=3.4 Hz, 1H), 3.84 (s, 3H), 3.60 (d, J=1.7 Hz, 3H), 3.48 (s, 3H), 2.67-2.58 (m, 2H), 2.46-2.40 (m, 1H), 2.05-2.02 (m, 2H), 1.67-1.65 (m, 6H), 1.55-1.53 (m, 6H) ppm; $^{13}$C NMR (125 MHz, CDCl$_3$): δ 156.90, 156.85, 156.1, 154.8, 154.7, 148.21, 148.16, 131.63, 131.57, 123.61, 123.60, 120.13, 120.09, 116.60, 116.55, 110.96, 110.95, 100.7, 95.7, 95.6, 95.1, 65.1, 65.0, 57.70, 57.66, 56.1, 55.6, 47.8, 47.7, 31.5, 31.4, 28.8, 28.7, 25.91, 25.89, 23.88, 23.85, 18.91, 18.90, 18.0 ppm; HRMS m/z (ESI) calcd. for C$_{23}$H$_{36}$O$_6$Na [M+Na]+: 431.2404; found: 431.2404.

1-(6-Methoxy-2,4-bis(methoxymethoxy)-3-(5-methyl-2-(prop-1-en-2-yl)hex-4-en-1-yl)phenyl)ethan-1-one

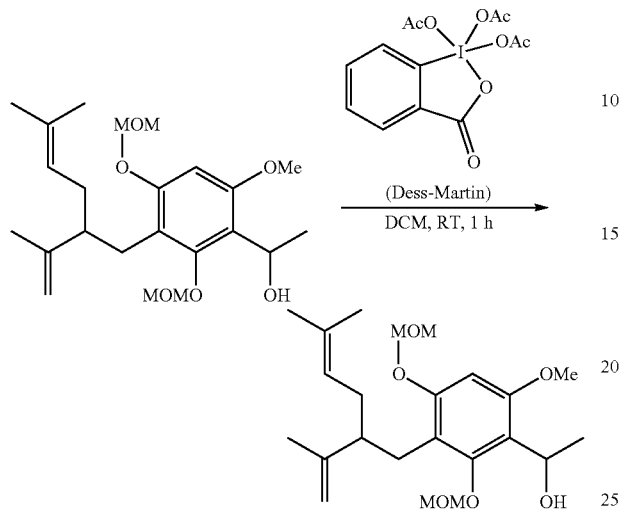

Dess-Martin reagent (441 mg, 1.0 mmol) was added to a solution of 1-(6-methoxy-2,4-bis(methoxymethoxy)-3-(5-methyl-2-(prop-1-en-2-yl)hex-4-en-1-yl)phenyl)ethan-1-ol (283 mg, 0.69 mmol) in DCM (15 mL) at room temperature. After stirring for 1 h, the reaction mixture was concentrated and the resulting crude product was purified by column chromatography on silica gel (0% to 3% EtOAc in hexanes) to give 1-(6-methoxy-2,4-bis(methoxymethoxy)-3-(5-methyl-2-(prop-1-en-2-yl)hex-4-en-1-yl)phenyl)ethan-1-one (214 mg, 50% yield) as a yellow oil, $R_f$=0.42 (silica gel, hexane:EtOAc=4:1). $^1$H NMR (500 MHz, CDCl$_3$): δ 6.55 (s, 1H), 5.16 (s, 2H), 5.06-5.03 (m, 1H), 4.89 (s, 2H), 4.63-4.62 (m, 1H), 4.52 (d, J=2.4 Hz, 1H), 3.79 (s, 3H), 3.50 (s, 3H), 3.49 (s, 3H), 2.66 (d, J=7.3 Hz, 2H), 2.48 (s, 3H), 2.46-2.42 (m, 1H), 2.07-2.02 (m, 2H), 1.69 (s, 3H), 1.65 (s, 3H), 1.56 (s, 3H) ppm; $^{13}$C NMR (125 MHz, CDCl$_3$): δ 202.3, 158.1, 155.8, 154.4, 148.1, 131.6, 123.6, 120.0, 116.8, 111.1, 101.3, 94.9, 94.7, 57.6, 56.2, 55.9, 47.7, 32.8, 31.5, 28.3, 25.9, 18.8, 18.0 ppm; HRMS m/z (ESI) calcd. for C$_{23}$H$_{34}$O$_6$Na [M+N]$^+$: 429.2248; found: 429.2248.

2,4-Bis(methoxymethoxy)benzaldehyde

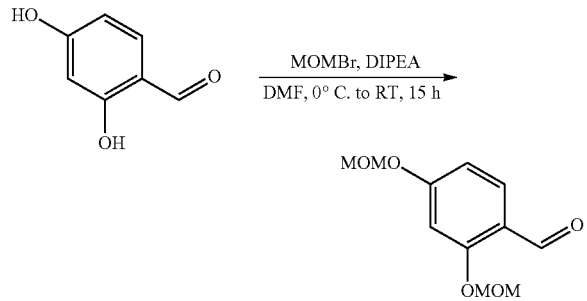

DIPEA (10.5 mL, 60 mmol) was slowly added to a solution of 2,4-dihydroxybenzaldehyde (2.07 g, 15 mmol) in anhydrous DMF (40 mL) at room temperature. After stirring for 30 mins, the solution was cooled to 0° C. and MOMBr (5.0 mL, 60 mmol) was added at this temperature. The mixture was then warmed to room temperature and stirred for 15 h. The reaction was quenched with water and the aq. layer was extracted with Et$_2$O. The combined organic layers were evaporated to dryness and the crude product was purified by column chromatography on silica gel (0% to 5% EtOAc in hexanes) to give 2,4-bis(methoxymethoxy)benzaldehyde (3.1 g, 91% yield) as a light yellow solid; $R_f$=0.35 (silica gel, hexane:EtOAc=4:1). $^1$H NMR (400 MHz, CDCl$_3$): δ 10.3 (s, 1H), 7.80 (d, J=8.7 Hz, 1H), 6.82 (d, J=2.1 Hz, 1H), 6.75-6.72 (dd, J=1.5 Hz, 8.7 Hz, 1H), 5.27 (s, 2H), 5.21 (s, 2H), 3.52 (s, 3H), 3.48 (s, 3H) ppm.

(E)-3-(2,4-bis(methoxymethoxy)phenyl)-1-(6-methoxy-2,4-bis(methoxymethoxy)-3-(5-methyl-2-(prop-1-en-2-yl)hex-4-en-1-yl)phenyl)prop-2-en-1-one

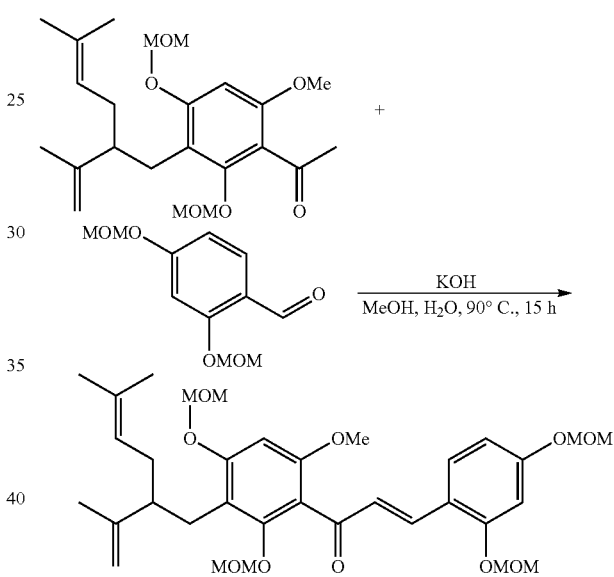

A solution of 1-(6-methoxy-2,4-bis(methoxymethoxy)-3-(5-methyl-2-(prop-1-en-2-yl)hex-4-en-1-yl)phenyl)ethan-1-one (86 mg, 0.21 mmol), 2,4-bis(methoxymethoxy)benzaldehyde (72 mg, 0.32 mmol) and KOH (356 mg, 6.3 mmol) in MeOH (10 mL) and H$_2$O (2 mL) was stirred and heated at 90° C. for 15 h. The reaction mixture was concentrated and the aqueous solution was extracted with DCM. The separated organic layers were evaporated to dryness and the resulting crude product was purified by column chromatography on silica gel (0% to 20% EtOAc in hexanes) to give (E)-3-(2,4-bis(methoxymethoxy)phenyl)-1-(6-methoxy-2,4-bis(methoxymethoxy)-3-(5-methyl-2-(prop-1-en-2-yl)hex-4-en-1-yl)phenyl)prop-2-en-1-one (90 mg, 69% yield) as a yellow oil; $R_f$=0.42 (silica gel, hexane:EtOAc=2:1). $^1$H NMR (400 MHz, CD$_3$CN): δ 7.56 (d, J=8.7 Hz, 1H), 7.51 (d, J=16.2 Hz, 1H), 6.89 (d, J=16.2 Hz, 1H), 6.76 (d, J=2.3 Hz, 1H), 6.72-6.70 (m, 1H), 6.62 (s, 1H), 5.23 (s, 2H), 5.19 (s, 2H), 5.18 (s, 2H), 5.08-5.04 (m, 1H), 4.83 (s, 2H), 4.62-4.61 (m, 1H), 4.51 (d, J=2.3 Hz, 1H), 3.71 (s, 3H), 3.48 (s, 3H), 3.41 (s, 3H), 3.39 (s, 3H), 3.35 (s, 3H), 2.71-2.65 (m, 2H), 2.53-2.46 (m, 1H), 2.10-2.07 (m, 2H, 1.69 (s, 3H), 1.63 (s, 3H), 1.55 (s, 3H) ppm; $^{13}$C NMR (100 MHz, CD$_3$CN): δ 195.3, 161.4, 158.7, 158.2, 157.1, 155.3, 149.2, 140.4, 132.4, 130.6, 128.7, 124.4, 119.0, 118.8, 117.5, 111.6, 110.6, 104.3, 101.6, 95.9, 95.8, 95.7, 95.2, 57.9, 56.74, 56.73, 56.60, 56.58, 48.7, 32.2, 28.9, 25.9, 18.9, 17.9 ppm; HRMS m/z (ESI) calcd. for $C_{34}H_{46}O_{10}Na$ [M+Na]$^+$: 637.2983; found: 637.2985.

(E)-1-(2,4-dihydroxy-6-methoxy-3-(5-methyl-2-(prop-1-en-2-yl)hex-4-en-1-yl)phenyl)-3-(2,4-dihydroxyphenyl)prop-2-en-1-one (Kuraridin)

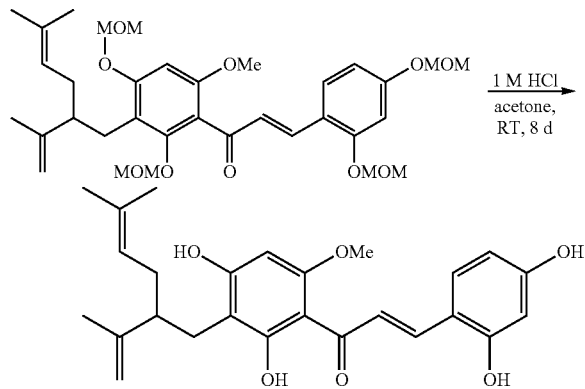

A solution of (E)-3-(2,4-bis(methoxymethoxy)phenyl)-1-(6-methoxy-2,4-bis(methoxymethoxy)-3-(5-methyl-2-(prop-1-en-2-yl)hex-4-en-1-yl)phenyl)prop-2-en-1-one (34 mg, 0.055 mmol) and 1 M HCl solution (5 mL) in acetone (5 mL) was stirred at room temperature for 8 days. The reaction mixture was concentrated and extracted with EtOAc. The separated organic layers were evaporated to dryness and the crude product was purified by column chromatography on silica gel and prep. HPLC (15% H$_2$O in acetonitrile, 5.0 mL/min) to give Kuraridin (10.5 mg, 43% yield) as an orange red solid, $R_f$=0.35 (silica gel, hexane: acetone=1:1). $^1$H NMR (500 MHz, CD$_3$CN): δ 14.73 (s, 1H), 7.98 (d, J=15.7 Hz, 1H), 7.92 (d, J=15.6 Hz, 1H), 7.49 (d, J=8.6 Hz, 1H), 7.15-7.12 (m, 0.4H), 6.83-6.80 (m, 0.3H), 6.42-6.37 (dd, J=2.4 Hz, 8.5 Hz, 1H), 6.38 (d, J=2.4 Hz, 1H), 6.02 (s, 1H), 5.05-5.01 (m, 1H), 4.60-4.59 (m, 1H), 4.53 (d, J=2.5 Hz, 1H), 3.87 (s, 3H), 2.65-2.58 (m, 2H), 2.54-2.50 (m, 1H), 2.07 (t, J=7.1 Hz, 2H), 1.69 (s, 3H), 1.62 (s, 3H), 1.55 (s, 3H) ppm; $^{13}$C NMR (125 MHz, CD$_3$CN): δ 194.0, 166.8, 163.0, 161.9, 161.4, 159.1, 149.7, 138.7, 132.1, 131.5, 125.4, 124.5, 115.9, 111.3, 109.3, 108.3, 106.3, 103.6, 91.6, 56.3, 47.6, 32.2, 27.8, 25.9, 18.9, 17.9 ppm; HRMS m/z (ESI) calcd. for $C_{26}H_{29}O_6$ [M−H]$^-$: 437.1970; found: 437.1972.

2-(Methoxymethoxy)benzaldehyde

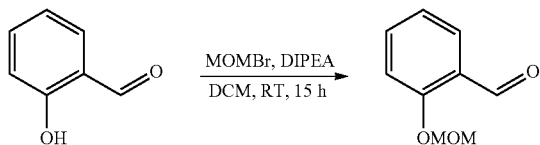

To a solution of 2-hydroxybenzaldehyde (1.0 g, 8.2 mmol) and DIPEA (2.1 mL, 12.3 mmol) in DCM (20 mL) was added MOMBr (1 mL, 12.3 mmol) at room temperature.

The mixture was stirred at room temperature for 15 h then concentrated to dryness. The resulting crude product was purified by column chromatography on silica gel (0% to 2% EtOAc in hexanes) to afford 2-(methoxymethoxy)benzaldehyde (1.29 g, 95% yield) as a light yellow oil. In NMR (400 MHz, CDCl$_3$): δ 10.51 (s, 1H), 7.85-7.82 (m, 1H), 7.55-7.51 (m, 1H), 7.21 (d, J=8.4 Hz, 1H), 7.10-7.06 (m, 1H), 5.30 (s, 2H), 3.52 (s, 3H) ppm.

(E)-1-(6-methoxy-2,4-bis(methoxymethoxy)-3-(5-methyl-2-(prop-1-en-2-yl)hex-4-en-1-yl)phenyl)-3-(2-(methoxymethoxy)phenyl)prop-2-en-1-one

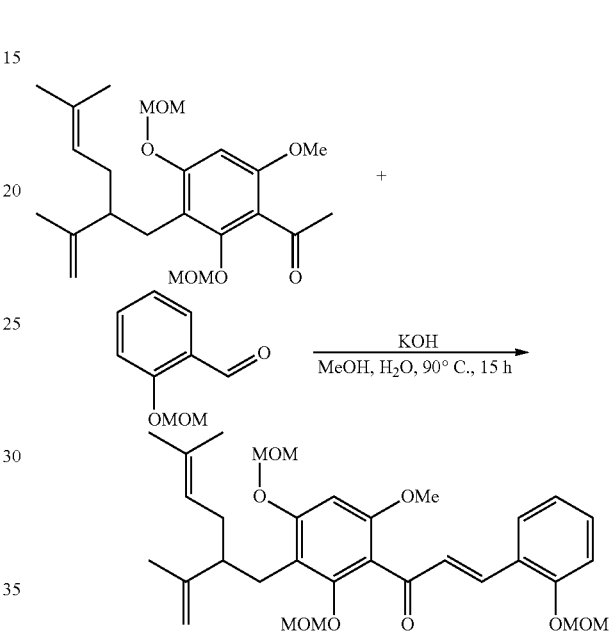

A solution of 1-(6-methoxy-2,4-bis(methoxymethoxy)-3-(5-methyl-2-(prop-1-en-2-yl)hex-4-en-1-yl)phenyl)ethan-1-one (50 mg, 0.12 mmol), 2-(methoxymethoxy)benzaldehyde (31 mg, 0.18 mmol) and KOH (207 mg, 3.69 mmol) in MeOH (5 mL) and H$_2$O (1 mL) was stirred and heated at 90° C. for 15 h. The reaction mixture was concentrated and the aqueous solution was extracted with DCM. The separated organic layers were evaporated to dryness and the resulting crude product was purified by column chromatography on silica gel (0% to 10% EtOAc in hexanes) to give (E)-1-(6-methoxy-2,4-bis(methoxymethoxy)-3-(5-methyl-2-(prop-1-en-2-yl)hex-4-en-1-yl)phenyl)-3-(2-(methoxymethoxy)phenyl)prop-2-en-1-one (47.8 mg, 70% yield) as a yellow oil, $R_f$=0.36 (silica gel, hexane:EtOAc=4:1). $^1$H NMR (500 MHz, CDCl$_3$): δ 7.72 (d, J=16.2 Hz, 1H), 7.53 (d, J=6.8 Hz, 1H), 7.31 (t, J=8.4 Hz, 1H), 7.13 (d, J=8.3 Hz, 1H), 7.06 (d, J=16.2 Hz, 1H), 7.00 (t, J=7.5 Hz, 1H), 6.59 (s, 1H), 5.20 (s, 2H), 5.19 (s, 2H), 5.06 (t, J=5.4 Hz, 1H), 4.90 (s, 2H), 4.64-4.63 (m, 1H), 4.53 (d, J=2.6 Hz, 1H), 3.75 (s, 3H), 3.51 (s, 3H), 3.45 (s, 3H), 3.44 (s, 3H), 2.72 (d, J=7.4 Hz, 2H), 2.54-2.48 (m, 1H), 2.14-2.06 (m, 2H), 1.70 (s, 3H), 1.66 (s, 3H), 1.57 (s, 3H) ppm; $^{13}$C NMR (125 MHz, CDCl$_3$): δ 194.9, 158.2, 156.44, 156.37, 155.1, 148.1, 139.8, 131.60, 131.58, 129.8, 128.9, 124.8, 123.6, 122.0, 118.0, 116.8, 115.0, 111.2, 101.0, 95.0, 94.8, 94.6, 57.6, 56.3, 56.2, 56.1, 47.9, 31.6, 28.2, 25.9, 18.7, 18.0 ppm; HRMS m/z (ESI) calcd. for $C_{32}H_{42}O_8Na$ [M+Na]$^+$: 577.2772; found: 577.2771.

(E)-1-(2,4-dihydroxy-6-methoxy-3-(5-methyl-2-(prop-1-en-2-yl)hex-4-en-1-yl)phenyl)-3-(2-hydroxyphenyl)prop-2-en-1-one

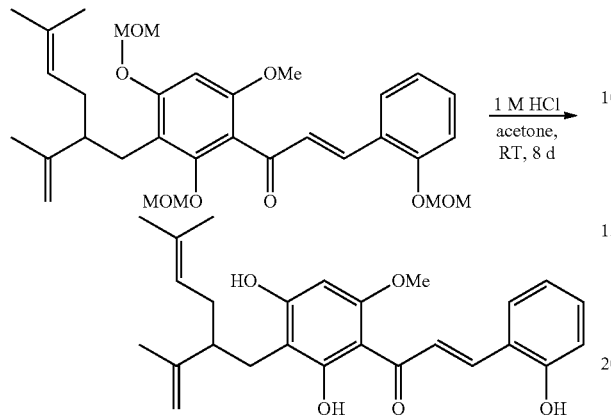

A solution of (E)-1-(6-methoxy-2,4-bis(methoxymethoxy)-3-(5-methyl-2-(prop-1-en-2-yl)hex-4-en-1-yl)phenyl)-3-(2-(methoxymethoxy)phenyl)prop-2-en-1-one (25 mg, 0.045 mmol) and 1 M HCl solution (3 mL) in acetone (3 mL) was stirred at room temperature for 8 days. The reaction mixture was concentrated and extracted with DCM. The separated organic layers were evaporated to dryness and the crude product was purified by column chromatography on silica gel (0% to 25% EtOAc in hexanes) to give (E)-1-(2,4-dihydroxy-6-methoxy-3-(5-methyl-2-(prop-1-en-2-yl)hex-4-en-1-yl)phenyl)-3-(2-hydroxyphenyl)prop-2-en-1-one (9.6 mg, 51% yield) as a yellow solid, $R_f$=0.33 (silica gel, hexane:EtOAc=2:1). $^1$H NMR (500 MHz, CD$_3$CN): δ 14.57 (s, 1H), 8.05 (d, J=15.8 Hz, 1H), 7.99 (d, J=15.8 Hz, 1H), 7.63-7.61 (dd, J=1.7 Hz, 7.8 Hz, 1H), 7.27-7.24 (m, 1H), 6.94-6.90 (m, 2H), 5.05-5.02 (m, 1H), 4.61-4.59 (m, 1H), 4.54-4.53 (m, 1H), 3.88 (m, 3H), 2.65-2.56 (m, 2H), 2.55-2.49 (m, 1H), 2.08 (t, J=6.8 Hz, 2H), 1.69 (s, 3H), 1.62 (s, 3H), 1.55 (s, 3H) ppm; $^{13}$C NMR (125 MHz, CD$_3$CN): δ 194.0, 156.8, 163.3, 162.1, 157.3, 149.7, 138.0, 132.4, 132.1, 129.8, 128.7, 124.5, 123.4, 121.3, 117.1, 111.3, 108.3, 106.3, 91.6, 56.4, 47.6, 32.2, 27.8, 25.9, 18.9, 17.9 ppm; HRMS m/z (ESI) calcd. for C$_{26}$H$_{29}$O$_5$ [M−H]$^-$: 421.2021; found: 421.2023.

4-(Methoxymethoxy)benzaldehyde

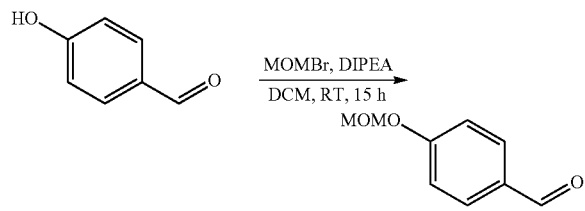

To a solution of 4-hydroxybenzaldehyde (1.0 g, 8.2 mmol) and DIPEA (2.1 mL, 12.3 mmol) in DCM (20 mL) was added MOMBr (1 mL, 12.3 mmol) at room temperature. The mixture was stirred at room temperature for 15 h then concentrated to dryness. The resulting crude product was purified by column chromatography on silica gel (0% to 2% EtOAc in hexanes) to afford 4-(methoxymethoxy)benzaldehyde (1.34 g, 99% yield) as a light yellow oil. $^1$H NMR (400 MHz, CDCl$_3$): δ 9.89 (s, 1H), 7.84-7.81 (m, 2H), 7.15-7.12 (m, 2H), 5.24 (s, 2H), 3.48 (s, 3H) ppm.

(E)-1-(6-methoxy-2,4-bis(methoxymethoxy)-3-(5-methyl-2-(prop-1-en-2-yl)hex-4-en-1-yl)phenyl)-3-(4-(methoxymethoxy)phenyl)prop-2-en-1-one

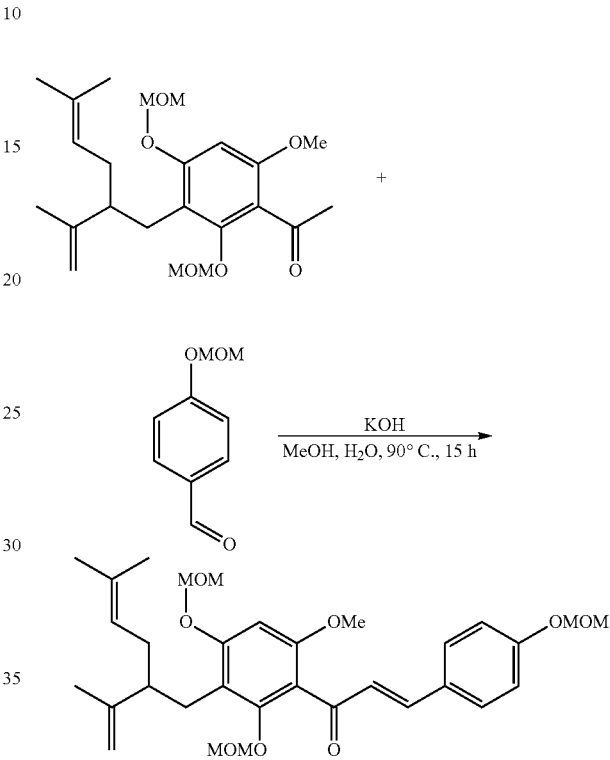

A solution of 1-(6-methoxy-2,4-bis(methoxymethoxy)-3-(5-methyl-2-(prop-1-en-2-yl)hex-4-en-1-yl)phenyl)ethan-1-one (50 mg, 0.12 mmol), 4-(methoxymethoxy)benzaldehyde (31 mg, 0.18 mmol) and KOH (207 mg, 3.69 mmol) in MeOH (10 mL) and H$_2$O (2 mL) was stirred and heated at 90° C. for 15 h. The reaction mixture was concentrated and the aqueous solution was extracted with DCM. The separated organic layers were evaporated to dryness and the resulting crude product was purified by column chromatography on silica gel (0% to 15% EtOAc in hexanes) to give (E)-1-(6-methoxy-2,4-bis(methoxymethoxy)-3-(5-methyl-2-(prop-1-en-2-yl)hex-4-en-1-yl)phenyl)-3-(4-(methoxymethoxy)phenyl)prop-2-en-1-one (38 mg, 56% yield) as a light yellow oil, $R_f$=0.18 (silica gel, hexane:EtOAc=4:1). $^1$H NMR (400 MHz, CD$_3$CN): δ 7.50 (d, J=8.8 Hz, 2H), 7.17 (d, J=16.1 Hz, 1H), 7.03 (d, J=8.8 Hz, 2H), 6.83 (d, J=16.1 Hz, 1H), 6.62 (s, 1H), 5.24 (s, 2H), 5.20 (s, 2H), 5.09-5.06 (m, 1H), 4.82 (s, 2H), 4.64-4.63 (m, 1H), 4.52 (d, J=2.6 Hz, 1H), 3.71 (s, 3H), 3.49 (s, 3H), 3.41 (s, 3H), 3.38 (s, 3H), 2.72-2.70 (m, 2H), 2.56-2.49 (m, 1H), 2.09 (t, J=7.1 Hz, 2H), 1.69 (s, 3H), 1.64 (s, 3H), 1.56 (s, 3H) ppm; $^{13}$C NMR (100 MHz, CD$_3$CN): δ 195.0, 160.1, 158.7, 157.1, 155.4, 149.3, 145.3, 132.5, 131.0, 129.2, 128.3, 124.3, 118.5, 117.5, 111.6, 101.6, 95.9, 95.8, 95.0, 57.9, 56.8, 56.6, 56.5, 48.7, 32.3, 28.9, 25.9, 18.8, 18.0 ppm; HRMS m/z (ESI) calcd. for C$_{32}$H$_{42}$O$_8$Na [M+Na]$^+$: 577.2772; found: 577.2772.

(E)-1-(2,4-dihydroxy-6-methoxy-3-(5-methyl-2-(prop-1-en-2-yl)hex-4-en-1-yl)phenyl)-3-(4-hydroxyphenyl)prop-2-en-1-one

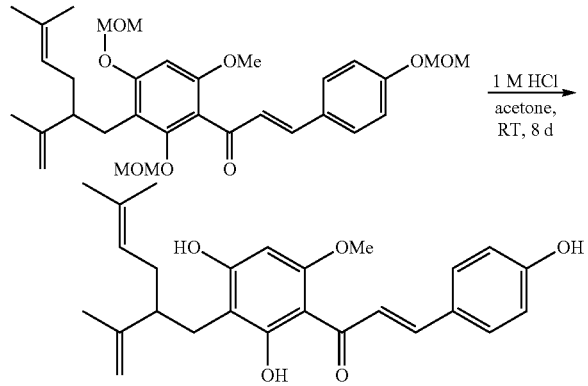

A solution of (E)-1-(6-methoxy-2,4-bis(methoxymethoxy)-3-(5-methyl-2-(prop-1-en-2-yl)hex-4-en-1-yl)phenyl)-3-(4-(methoxymethoxy)phenyl)prop-2-en-1-one (38 mg, 0.069 mmol) and 1 M HCl solution (5 mL) in acetone (5 mL) was stirred at room temperature for 8 days. The reaction mixture was concentrated and extracted with DCM. The separated organic layers were evaporated to dryness and the crude product was purified by column chromatography on silica gel (0% to 25% EtOAc in hexanes) to give (E)-1-(2,4-dihydroxy-6-methoxy-3-(5-methyl-2-(prop-1-en-2-yl)hex-4-en-1-yl)phenyl)-3-(4-hydroxyphenyl)prop-2-en-1-one (15 mg, 52% yield) as a yellow solid, $R_f$=0.22 (silica gel, hexane:EtOAc=2:1). $^1$H NMR (400 MHz, CD$_3$CN): δ 14.59 (s, 1H), 7.82 (d, J=15.6 Hz, 1H), 7.69 (d, J=15.6 Hz, 1H), 7.57-7.53 (m, 2H), 6.87-6.84 (m, 2H), 6.02 (s, 1H), 5.05-5.00 (m, 1H), 4.60-4.59 (m, 1H), 4.53 (d, J=2.4 Hz, 1H), 3.87 (s, 3H), 2.65-2.58 (m, 2H), 2.56-2.48 (m, 1H), 2.07 (t, J=6.2 Hz, 2H), 1.68 (s, 3H), 1.62 (s, 3H), 1.54 (s, 3H) ppm; $^{13}$C NMR (100 MHz, CD$_3$CN): δ 193.6, 166.8, 163.2, 162.0, 160.1, 149.6, 142.9, 132.1, 131.3, 128.3, 125.8, 124.5, 116.7, 111.3, 108.2, 106.2, 91.5, 56.4, 47.6, 32.1, 27.8, 25.9, 18.9, 17.9 ppm; HRMS m/z (ESI) calcd. for C$_{26}$H$_{29}$O$_5$ [M−H]$^−$: 421.2021; found: 421.2024.

(E)-1-(6-methoxy-2,4-bis(methoxymethoxy)-3-(5-methyl-2-(prop-1-en-2-yl)hex-4-en-1-yl)phenyl)-3-(2-methoxy-4-(methoxymethoxy)phenyl)prop-2-en-1-one

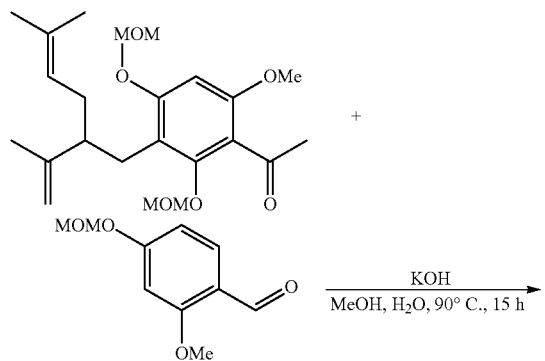

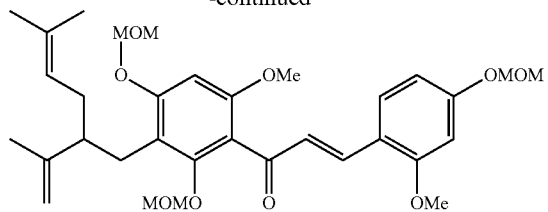

A solution of 1-(6-methoxy-2,4-bis(methoxymethoxy)-3-(5-methyl-2-(prop-1-en-2-yl)hex-4-en-1-yl)phenyl)ethan-1-one (50 mg, 0.12 mmol), 2-methoxy-4-(methoxymethoxy)benzaldehyde (36 mg, 0.18 mmol) and KOH (207 mg, 3.69 mmol) in MeOH (5 mL) and H$_2$O (1 mL) was stirred and heated at 90° C. for 15 h. The reaction mixture was concentrated and the aqueous solution was extracted with DCM. The separated organic layers were evaporated to dryness and the resulting crude product was purified by column chromatography on silica gel (0% to 17% EtOAc in hexanes) to give (E)-1-(6-methoxy-2,4-bis(methoxymethoxy)-3-(5-methyl-2-(prop-1-en-2-yl)hex-4-en-1-yl)phenyl)-3-(2-methoxy-4-(methoxymethoxy)phenyl)prop-2-en-1-one (41.5 mg, 58% yield) as a yellow oil, $R_f$=0.09 (silica gel, hexane:EtOAc=4:1). $^1$H NMR (500 MHz, CDCl$_3$): δ 7.56 (d, J=16.2 Hz, 1H), 7.43 (d, J=8.7 Hz, 1H), 6.98 (d, J=16.2 Hz, 1H), 6.64-6.61 (dd, J=2.3 Hz, 8.6 Hz, 1H), 6.58 (s, 1H), 6.56 (d, J=2.3 Hz, 1H), 5.19 (s, 2H), 5.18 (s, 2H), 5.09-5.06 (m, 1H), 4.89 (s, 2H), 4.64-4.63 (m, 1H), 4.53 (d, J=2.6 Hz, 1H), 3.80 (s, 3H), 3.74 (s, 3H), 3.51 (s, 3H), 3.48 (s, 3H), 3.45 (s, 3H), 2.73-2.67 (m, 2H), 2.54-2.49 (m, 1H), 2.12-2.05 (m, 2H), 1.70 (s, 3H), 1.66 (s, 3H), 1.57 (s, 3H) ppm; $^{13}$C NMR (100 MHz, CDCl$_3$): δ 195.6, 160.6, 160.1, 158.0, 156.3, 154.9, 148.2, 140.7, 131.6, 130.6, 127.9, 123.7, 118.1, 118.0, 116.7, 111.1, 107.9, 100.9, 100.0, 95.1, 94.9, 94.4, 57.7, 56.3, 56.2, 56.1, 55.5, 47.9, 31.6, 28.3, 25.9, 18.7, 18.0 ppm; HRMS m/z (ESI) calcd. for C$_{33}$H$_{44}$O$_9$Na [M+Na]$^+$: 607.2878; found: 607.2877.

(E)-1-(2,4-dihydroxy-6-methoxy-3-(5-methyl-2-(prop-1-en-2-yl)hex-4-en-1-yl)phenyl)-3-(4-hydroxy-2-methoxyphenyl)prop-2-en-1-one (rac-Kushenol D)

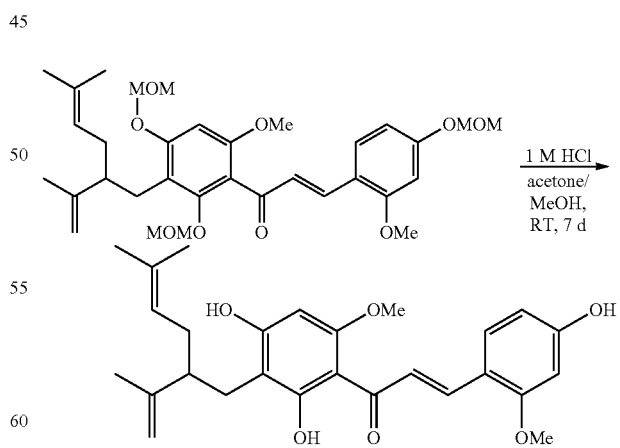

A solution of (E)-1-(6-methoxy-2,4-bis(methoxymethoxy)-3-(5-methyl-2-(prop-1-en-2-yl)hex-4-en-1-yl)phenyl)-3-(2-methoxy-4-(methoxymethoxy)phenyl)prop-2-en-1-one (20 mg, 0.03 mmol) and 1 M HCl solution (2 mL) in acetone (2 mL) and MeOH (2 mL) was stirred at room temperature for 7 days. The reaction mixture was concentrated and extracted with DCM. The separated organic layers were evaporated to dryness and the crude product was purified by column chromatography on silica gel (0% to 25% EtOAc in hexanes) to give (E)-1-(2,4-dihydroxy-6-methoxy-3-(5-methyl-2-(prop-1-en-2-yl)hex-4-en-1-yl)phenyl)-3-(4-hydroxy-2-methoxyphenyl)prop-2-en-1-one (6.3 mg, 41% yield) as a yellow solid, $R_f$=0.15 (silica gel, hexane:EtOAc=2:1). $^1$H NMR (400 MHz, CD$_3$CN): δ 14.69 (s, 1H), 7.98 (d, J=15.7 Hz, 1H), 7.91 (d, J=15.7 Hz, 1H), 7.54 (d, J=8.4 Hz, 1H), 6.50-6.46 (m, 2H), 6.03 (s, 1H), 5.05-5.01 (m, 1H), 4.60-4.59 (m, 1H), 4.53 (d, J=2.2 Hz, 1H), 3.884 (s, 3H), 3.881 (s, 3H), 2.65-2.56 (m, 2H), 2.55-2.47 (m, 1H), 2.09-2.05 (t, 2H), 1.69 (s, 3H), 1.62 (s, 3H), 1.55 (s, 3H) ppm; $^{13}$C NMR (125 MHz, CD$_3$CN): δ 194.0, 166.8, 162.9, 161.9, 161.8, 161.5, 149.7, 138.6, 132.1, 131.6, 125.8, 124.5, 117.1, 111.3, 109.0, 108.3, 106.3, 100.1, 91.5, 56.4, 56.3, 47.6, 32.2, 27.8, 25.9, 18.9, 17.9 ppm; HRMS m/z (ESI) calcd. for $C_{27}H_{31}O_6$ [M–H]$^-$: 451.2126; found: 451.2126.

All patents, patent applications, and other publications, including GenBank Accession Numbers and other sequence identification numbers, cited in this application are incorporated by reference in the entirety for all purposes.

REFERENCES

1. Hilliard, J. J., J. Fernandez, J. Melton, M. J. Macielag, R. Goldschmidt, K. Bush, and D. Abbanat. 2009. In vivo activity of the Pyrrolopyrazolyl-Substituted Oxazolidinone RWJ-416457. *Antimicrobial agents and chemotherapy*.
2. Leung, Y. H., R. W. Lai, A. C. Chan, J. Y. Lo, P. L. Ho, M. M. Wong, S. K. Chuang, and T. H. Tsang. 2012. Risk factors for community-associated methicillin-resistant *Staphylococcus aureus* infection in Hong Kong. *The Journal of infection* 64:494-499.
3. Fung, J. 2009. Current challenges in viral hepatitis, antimicrobial resistance and the influenza pandemic. *Expert review of anti-infective therapy* 7:945-949.
4. Tan, C. M., A. G. Therien, J. Lu, S. H. Lee, A. Caron, C. J. Gill, C. Lebeau-Jacob, L. Benton-Perdomo, J. M. Monteiro, P. M. Pereira, M. L. Elsen, J. Wu, K. Deschamps, M. Petcu, S. Wong, E. Daigneault, S. Kramer, L. Liang, E. Maxwell, D. Claveau, J. Vaillancourt, K. Skorey, J. Tam, H. Wang, T. C. Meredith, S. Sillaots, L. Wang-Jarantow, Y. Ramtohul, E. Langlois, F. Landry, J. C. Reid, G. Parthasarathy, S. Sharma, A. Baryshnikova, K. J. Lumb, M. G. Pinho, S. M. Soisson, and T. Roemer. 2012. Restoring methicillin-resistant *Staphylococcus aureus* susceptibility to beta-lactam antibiotics. *Science translational medicine* 4:126ra135.
5. Cheng, V. C., I. W. Li, A. K. Wu, B. S. Tang, K. H. Ng, K. K. To, H. Tse, T. L. Que, P. L. Ho, and K. Y. Yuen. 2008. Effect of antibiotics on the bacterial load of meticillin-resistant *Staphylococcus aureus* colonisation in anterior nares. *J Hosp Infect* 70:27-34.
6. Ho, P. L., E. L. Lai, K. H. Chow, L. S. Chow, K. Y. Yuen, and R. W. Yung. 2008. Molecular epidemiology of methicillin-resistant *Staphylococcus aureus* in residential care homes for the elderly in Hong Kong. *Diagn Microbiol Infect Dis* 61:135-142.
7. Ho, P. L., S. K. Chuang, Y. F. Choi, R. A. Lee, A. C. Lit, T. K. Ng, T. L. Que, K. C. Shek, H. K. Tong, C. W. Tse, W. K. Tung, and R. W. Yung. 2008. Community-associated methicillin-resistant and methicillin-sensitive *Staphylococcus aureus*: skin and soft tissue infections in Hong Kong. *Diagn Microbiol Infect Dis* 61:245-250.
8. Spentzas, T., R. Kudumula, C. Acuna, A. J. Talati, K. C. Ingram, F. Savorgnan, E. A. Meals, and B. K. English. 2011. Role of bacterial components in macrophage activation by the LAC and MW2 strains of community-associated, methicillin-resistant *Staphylococcus aureus*. *Cellular immunology* 269:46-53.
9. Sakoulas, G., and R. C. Moellering, Jr. 2008. Increasing antibiotic resistance among methicillin-resistant *Staphylococcus aureus* strains. *Clin Infect Dis* 46 Suppl 5:S360-367.
10. Dixon, R. A. 2001. Natural products and plant disease resistance. *Nature* 411:843-847.
11. Chan, B. C., M. Ip, C. B. Lau, Q. B. Han, C. Jolivalt, J. Paris, N. E. Rainer, R. H. See, K. P. Fung, and P. C. Leung. 2012. Role of medicinal herbs in treatment against Methicillin resistant *Staphylococcus aureus* MRSA infections. Studium Press, New Delhi.
12. Chan, B. C., H. Yu, C. W. Wong, S. L. Lui, C. Jolivalt, C. Ganem-Elbaz, J. M. Paris, B. Morleo, M. Litaudon, C. B. Lau, M. Ip, K. P. Fung, P. C. Leung, and Q. B. Han. 2012. Quick identification of kuraridin, a noncytotoxic anti-MRSA (methicillin-resistant *Staphylococcus aureus*) agent from *Sophora flavescens* using high-speed countercurrent chromatography. *Journal of chromatography* 880:157-162.
13. Chan, B. C.-L., C. B.-S. Lau, C. Jolivalt, S.-L. Lui, C. Ganem-, Elbaz, J.-M. Paris, M. Litaudon, K.-P. Fung, P.-C. Leung, and M. Ip. 2011. Chinese medicinal herbs against antibiotic-resistant bacterial pathogens. FORMATEX, Badaj oz.
14. Chan, B. C., M. Ip, C. B. Lau, S. L. Lui, C. Jolivalt, C. Ganem-Elbaz, M. Litaudon, N. E. Reiner, H. Gong, R. H. See, K. P. Fung, and P. C. Leung. 2011. Synergistic effects of baicalein with ciprofloxacin against NorA over-expressed methicillin-resistant *Staphylococcus aureus* (MRSA) and inhibition of MRSA pyruvate kinase. *Journal of ethnopharmacology* 137:767-773.
15. Shibata, H., T. Nakano, M. A. Parvez, Y. Furukawa, A. Tomoishi, S. Niimi, N. Arakaki, and T. Higuti. 2009. Triple combinations of lower and longer alkyl gallates and oxacillin improve antibiotic synergy against methicillin-resistant *Staphylococcus aureus*. *Antimicrobial agents and chemotherapy* 53:2218-2220.
16. Gibbons, S., E. Moser, and G. W. Kaatz. 2004. Catechin gallates inhibit multidrug resistance (MDR) in *Staphylococcus aureus*. *Planta medica* 70:1240-1242.
17. Tegos, G., F. R. Stermitz, O. Lomovskaya, and K. Lewis. 2002. Multidrug pump inhibitors uncover remarkable activity of plant antimicrobials. *Antimicrobial agents and chemotherapy* 46:3133-3141.
18. Hagihara, M., J. L. Crandon, and D. P. Nicolau. 2012. The efficacy and safety of antibiotic combination therapy for infections caused by Gram-positive and Gram-negative organisms. *Expert opinion on drug safety* 11:221-233.
19. Steenbergen, J. N., J. F. Mohr, and G. M. Thorne. 2009. Effects of daptomycin in combination with other antimicrobial agents: a review of in vitro and animal model studies. *The Journal of antimicrobial chemotherapy* 64:1130-1138.
20. Snydman, D. R., L. A. McDermott, and N. V. Jacobus. 2005. Evaluation of in vitro interaction of daptomycin with gentamicin or beta-lactam antibiotics against *Staphylococcus aureus* and Enterococci by FIC index and timed-kill curves. *J. Chemother* 17:614-621.

21. Roehm, N. W., G. H. Rodgers, S. M. Hatfield, and A. L. Glasebrook. 1991. An improved colorimetric assay for cell proliferation and viability utilizing the tetrazolium salt XTT. *J Immunol Methods* 142:257-265.
22. Labandeira-Rey, M., F. Couzon, S. Boisset, E. L. Brown, M. Bes, Y. Benito, E. M. Barbu, V. Vazquez, M. Hook, J. Etienne, F. Vandenesch, and M. G. Bowden. 2007. *Staphylococcus aureus* Panton-Valentine leukocidin causes necrotizing pneumonia. *Science* (New York, N.Y 315:1130-1133.
23. Azoulay-Dupuis, E., J. Mohler, J. P. Bedos, C. Barau, and B. Fantin. 2006. Efficacy of cethromycin, a new ketolide, against *Streptococcus pneumoniae* susceptible or resistant to erythromycin in a murine pneumonia model. *Antimicrobial agents and chemotherapy* 50:3033-3038.
24. Beigelman, A., S. Gunsten, C. L. Mikols, I. Vidaysky, C. L. Cannon, S. L. Brody, and M. J. Walter. 2009. Azithromycin attenuates airway inflammation in a noninfectious mouse model of allergic asthma. *Chest* 136:498-506.
25. Zuluaga, A. F., B. E. Salazar, C. A. Rodriguez, A. X. Zapata, M. Agudelo, and O. Vesga. 2006. Neutropenia induced in outbred mice by a simplified low-dose cyclophosphamide regimen: characterization and applicability to diverse experimental models of infectious diseases. *BMC infectious diseases* 6:55.
26. Rubinstein, E., and Y. Keynan. 2014. Vancomycin revisited—60 years later. *Frontiers in public health* 2:217.
27. Peng, Q., Y. Huang, B. Hou, D. Hua, F. Yao, and Y. Qian. 2010. Green tea extract weakens the antibacterial effect of amoxicillin in methicillin-resistant *Staphylococcus aureus* infected mice. *Phytother Res* 24:141-145.
28. Hu, M., H. K. Lee, E. Wat, C. B. S. Lau, C. S. Ho, C. K. Wong, and B. Tomlinson. 2014. Effect of green tea extract and soy isoflavones on the pharmacokinetics of simvastatin in Healthy Chinese male volunteers. In *9th Congress of the Asian-Pacific Society of Atherosclerosis and Vascular Diseases & 16th Diabetes and Cardiovascular Risk Factors—East Meets West Symposium. Journal of Atherosclerosis and Thrombosis*, Hong Kong. S20.
29. Palacios, L., H. Rosado, V. Micol, A. E. Rosato, P. Bernal, R. Arroyo, H. Grounds, J. C. Anderson, R. A. Stabler, and P. W. Taylor. 2014. Staphylococcal phenotypes induced by naturally occurring and synthetic membrane-interactive polyphenolic beta-lactam resistance modifiers. *PloS one* 9:e93830.
30. Sasaki, T., W. Li, K. Higai, T. H. Quang, Y. H. Kim, and K. Koike. 2014. Protein tyrosine phosphatase 1B inhibitory activity of lavandulyl flavonoids from roots of *Sophora flavescens*. *Planta medica* 80:557-560.
31. Jung, H. A., T. Yokozawa, B. W. Kim, J. H. Jung, and J. S. Choi. 2010. Selective inhibition of prenylated flavonoids from *Sophora flavescens* against BACE1 and cholinesterases. *The American journal of Chinese medicine* 38:415-429.
32. Jung, H. A., N. Y. Yoon, S. S. Kang, Y. S. Kim, and J. S. Choi. 2008. Inhibitory activities of prenylated flavonoids from *Sophora flavescens* against aldose reductase and generation of advanced glycation endproducts. *The Journal of pharmacy and pharmacology* 60:1227-1236.
33. Kim, J. H., Y. B. Ryu, N. S. Kang, B. W. Lee, J. S. Heo, I. Y. Jeong, and K. H. Park. 2006. Glycosidase inhibitory flavonoids from *Sophora flavescens*. *Biological & pharmaceutical bulletin* 29:302-305.
34. Chung, M. Y., M. C. Rho, J. S. Ko, S. Y. Ryu, K. H. Jeune, K. Kim, H. S. Lee, and Y. K. Kim. 2004. In vitro inhibition of diacylglycerol acyltransferase by prenylflavonoids from *Sophora flavescens*. *Planta medica* 70:258-260.
35. Kim, S. J., K. H. Son, H. W. Chang, S. S. Kang, and H. P. Kim. 2003. Tyrosinase inhibitory prenylated flavonoids from *Sophora flavescens*. *Biological & pharmaceutical bulletin* 26:1348-1350.
36. Ohlsen, K., and S. Donat. 2010. The impact of serine/threonine phosphorylation in *Staphylococcus aureus*. *Int J Med Microbiol* 300:137-141.
37. 程书钧 穆秀珍, and 王德昌, 2012. 苦参绿茶组合物及其在治疗湿疣中的应用 中華人民共和國國家知識產權局, ed, China.

TABLE 1

Minimum inhibitory concentrations (MIC) of baicalein, berberine, epicatechin gallate (ECG), gallic acid, kuraridin and tanshinone against different methicillin-resistant *Staphylococcus aureus* (MRSA) strains.

| Strains | Baicalein | | Berberine | | ECG | | Gallic acid | | Kuraridin | | Tanshinone | |
| | | | | | MIC | | | | | | | |
| --- | --- | --- | --- | --- | --- | --- | --- | --- | --- | --- | --- | --- |
| | 99.9 | 90 | 99.9 | 90 | 99.9 | 90 | 99.9 | 90 | 99.9 | 90 | 99.9 | 90 |
| APH2''-AAC6' | >512 | 128 | >512 | 256 | >512 | 8 | >512 | 512 | 8 | 8 | >128 | >128 |
| APH3' | >512 | 64 | >512 | 128 | >512 | 4 | >512 | 512 | 8 | 8 | >128 | >128 |
| ANT4 | >512 | 128 | >512 | 256 | >512 | 8 | >512 | 512 | 8 | 4 | >128 | >128 |
| RN4220 | >512 | 64 | >512 | 256 | >512 | 8 | >512 | 512 | 8 | 8 | >128 | >128 |
| 1199B' | >512 | 128 | >512 | 256 | >512 | 8 | >512 | 512 | 16 | 16 | >128 | >128 |
| ST239 | >512 | 128 | >512 | 256 | >512 | 16 | >512 | 256 | 8 | 8 | >128 | >128 |
| ATCC25923 | >512 | 128 | >512 | 256 | >512 | 128 | >512 | 256 | 8 | 8 | >128 | >128 |

Minimum inhibitory concentrations (MICs) were defined as the lowest concentration of antibacterial, which resulted in either ≥99.9% or ≥90% inhibition of growth compared with that of the drug-free control.

TABLE 2

Combinations of tested compounds with enhanced antibacterial activities.

| | MIC alone | MIC combine | FIC | FICI |
|---|---|---|---|---|
| (a) Baicalein and epicatechin gallate (ECG) | | | | |
| 1199B | | | | |
| Baicalein | 512 | 8 | 0.0625 | 0.31 |
| ECG | 32 | 8 | 0.25 | |
| Kuraridin and epicatechin gallate (ECG) | | | | |
| ECG | 512 | 32 | 0.06 | 0.31 |
| Kuraridin | 16 | 4 | 0.25 | |
| RN4220 | | | | |
| ECG | 512 | 8 | 0.01 | 0.26 |
| Kuraridin | 8 | 2 | 0.25 | |
| APH2 | | | | |
| ECG | 512 | 0.5 | 0.0009 | 0.25 |
| Kuraridin | 8 | 2 | 0.25 | |
| APH3 | | | | |
| ECG | 512 | 0.5 | 0.0009 | 0.25 |
| Kuraridin | 8 | 2 | 0.25 | |
| ANT4 | | | | |
| ECG | 512 | 16 | 0.03 | 0.38 |
| Kuraridin | 8 | 2 | 0.25 | |

Minimum inhibitory concentrations (MIC) were defined as the lowest concentration of antibacterial, which resulted in ≥99.9% inhibition of growth compared with that of the drug-free control. The effects of combinations were evaluated by calculating the Fractional Inhibitory Concentration Index (FICI) for each combination using the following formula: FIC of drug A = MIC of drug A in combination/MIC of drug A alone; FIC of drug B = MIC of drug B in combination/MIC of drug B alone; hence FICI = FIC of drug A + FIC of drug B. Off-scale MICs were converted to the next highest or next lowest doubling concentration. "Synergy" was defined when FIC index was less than or equal to 0.5; while "additive" in which the FIC index was greater than 0.5 and less than or equal to 1.0; whereas "indifferent" when the FIC index was greater than 1.0 and less than or equal to 2.0; and "antagonistic" in cases which the FIC index was greater than 2.0.

TABLE 3

Minimum inhibitory concentrations (MIC) and fractional inhibitory concentration indices (FICI) of kuraridin (Kur) and epicatechin gallate (ECG) against (a) community-associated (CA) and (b) hospital-associated (HA) MRSA strains.

| | MIC alone | | MIC combine | | FIC | | |
|---|---|---|---|---|---|---|---|
| | ECG | Kur | ECG | Kur | ECG | Kur | FICI |
| (a) CA MRSA | | | | | | | |
| W44 | 512 | 8 | 2 | 2 | 0.004 | 0.25 | 0.25 |
| W45 | 512 | 8 | 1 | 4 | 0.002 | 0.5 | 0.50 |
| W46 | 512 | 8 | 8 | 4 | 0.015 | 0.5 | 0.52 |
| W47 | 512 | 8 | 2 | 4 | 0.004 | 0.5 | 0.50 |
| W48 | 512 | 8 | 1 | 4 | 0.002 | 0.5 | 0.50 |
| W101 | 512 | 8 | 1 | 4 | 0.002 | 0.5 | 0.50 |
| W103 | 512 | 8 | 1 | 4 | 0.002 | 0.5 | 0.50 |
| W106 | 512 | 8 | 1 | 2 | 0.002 | 0.25 | 0.25 |
| W113 | 512 | 8 | 1 | 4 | 0.002 | 0.5 | 0.50 |
| W114 | 512 | 8 | 1 | 4 | 0.002 | 0.5 | 0.50 |
| ST30 | 512 | 8 | 0.25 | 4 | 0.0004 | 0.5 | 0.50 |
| ATCC 25293 | 512 | 8 | 4 | 4 | 0.008 | 0.5 | 0.51 |
| (b) HA MRSA | | | | | | | |
| W231 | 512 | 4 | 8 | 1 | 0.016 | 0.25 | 0.27 |
| W232 | 512 | 8 | 4 | 2 | 0.008 | 0.25 | 0.26 |
| W233 | 512 | 4 | 2 | 2 | 0.004 | 0.5 | 0.50 |
| W234 | 512 | 8 | 1 | 4 | 0.002 | 0.5 | 0.50 |
| W235 | 512 | 8 | 1 | 4 | 0.002 | 0.5 | 0.50 |
| W238 | 512 | 8 | 1 | 4 | 0.002 | 0.5 | 0.50 |
| W239 | 512 | 8 | 1 | 4 | 0.002 | 0.5 | 0.50 |
| W240 | 512 | 8 | 4 | 4 | 0.008 | 0.5 | 0.51 |
| ST239 | 512 | 8 | 2 | 4 | 0.004 | 0.5 | 0.50 |

TABLE 4

Minimum inhibitory concentrations (MIC) and fractional inhibitory concentration indices (FICI) of kuraridin and epicatechin gallate (ECG) with antibiotics against (a) gentamicin (Gen) and (b) fusidic acid (Fus) resistant MRSA strains.

(a)

| Strains | MIC alone | | | MIC combine | | | FIC | | | FICI |
|---|---|---|---|---|---|---|---|---|---|---|
| | ECG | Kur | Gen | ECG | Kur | Gen | ECG | Kur | Gen | |
| W231 | 512 | 8 | 64 | 0.25 | 2 | 1 | 0.0004 | 0.25 | 0.015 | 0.27 |
| | 512 | 8 | — | 4 | 2 | — | 0.008 | 0.25 | — | 0.26 |
| W233 | 512 | 8 | 512 | 0.25 | 4 | 16 | 0.0005 | 0.5 | 0.03 | 0.53 |
| | 512 | 8 | — | 16 | 8 | — | 0.03 | 1 | — | 1.03 |
| W238 | 512 | 8 | 512 | 0.25 | 2 | 16 | 0.0004 | 0.25 | 0.03 | 0.28 |
| | 512 | 8 | — | 0.5 | 4 | — | 0.0004 | 0.5 | — | 0.50 |
| APH2 | 512 | 8 | 512 | 0.25 | 2 | 16 | 0.0005 | 0.25 | 0.0312 | 0.28 |
| | 512 | 8 | — | 0.5 | 2 | — | 0.0009 | 0.25 | — | 0.25 |

(b)

| Strains | MIC alone | | | MIC combine | | | FIC | | | FICI |
|---|---|---|---|---|---|---|---|---|---|---|
| | ECG | Kur | Fus | ECG | Kur | Fus | ECG | Kur | Fus | |
| 82356 | 512 | 8 | 32 | 0.25 | 4 | 1 | 0.008 | 0.25 | 0.03 | 0.53 |
| | 512 | 8 | — | 8 | 4 | — | 0.016 | 0.5 | — | 0.52 |
| 73621 | 512 | 8 | 32 | 0.25 | 4 | 1 | 0.004 | 0.5 | 0.03 | 0.53 |
| | 512 | 8 | — | 16 | 4 | — | 0.003 | 0.5 | — | 0.53 |
| 96591 | 512 | 4 | 32 | 0.25 | 2 | 1 | 0.002 | 0.5 | 0.03 | 0.53 |
| | 512 | 8 | — | 16 | 4 | — | 0.003 | 0.5 | — | 0.53 |

TABLE 4-continued

Minimum inhibitory concentrations (MIC) and fractional inhibitory concentration indices (FICI) of kuraridin and epicatechin gallate (ECG) with antibiotics against (a) gentamicin (Gen) and (b) fusidic acid (Fus) resistant MRSA strains.

| ANT4 | 512 | 8 | 64 | 4  | 2 | 8 | 0.0007 | 0.25 | 0.125 | 0.38 |
|------|-----|---|----|----|---|---|--------|------|-------|------|
|      | 512 | 8 | —  | 16 | 2 | — | 0.03   | 0.25 | —     | 0.28 |

Minimum inhibitory concentrations (MIC) were defined as the lowest concentration of antibacterial, which resulted in ≥99.9% inhibition of growth compared with that of the drug-free control. Fractional inhibitory concentration indices (FICI) for triple combinations were calculated as follows: FIC index (FICI) = FICdrug A + FICdrug B + FICdrug C = (Ccombdrug A/MICdrug A) + (Ccombdrug B/MICdrug B) + (Ccombdrug C/MICdrug C), where Ccombdrug A, Ccombdrug B and Ccombdrug C are the concentrations of drugs tested; and MICdrug A, MICdrug B, and MICdrug C are the MICs of the compounds when used alone.

TABLE 5

Minimum inhibitory concentrations (MIC) and fractional inhibitory concentration indices (FICI) of kuraridin (Kur) and epicatechin gallate (ECG) with vancomycin (Van) against clinical MRSA strains.

| | MIC alone | | | MIC combine | | | FIC | | | |
|---|---|---|---|---|---|---|---|---|---|---|
| Strains | ECG | Kur | Van | ECG | Kur | Van | ECG | Kur | Van | FICI |
| W44   | 512 | 8 | 1 | 0.25 | 2 | 0.5  | 0.0004 | 0.25  | 0.5  | 0.75 |
| W45   | 512 | 8 | 1 | 0.25 | 2 | 0.5  | 0.0004 | 0.25  | 0.5  | 0.75 |
| W46   | 512 | 8 | 1 | 1    | 4 | 0.5  | 0.002  | 0.5   | 0.5  | 1.00 |
| W47   | 512 | 8 | 1 | 0.25 | 2 | 0.25 | 0.0004 | 0.25  | 0.25 | 0.50 |
| W48   | 512 | 8 | 1 | 1    | 2 | 0.5  | 0.002  | 0.25  | 0.5  | 0.75 |
| W231  | 512 | 8 | 1 | 0.25 | 1 | 0.5  | 0.0004 | 0.125 | 05   | 0.62 |
| W232  | 512 | 8 | 1 | 8    | 2 | 0.5  | 0.03   | 0.25  | 0.5  | 0.75 |
| W233  | 512 | 8 | 1 | 8    | 2 | 0.5  | 0.03   | 0.25  | 0.5  | 0.75 |
| W238  | 512 | 8 | 1 | 0.25 | 2 | 0.5  | 0.0004 | 0.25  | 0.5  | 0.75 |
| W239  | 512 | 8 | 1 | 0.5  | 2 | 0.5  | 0.0009 | 0.25  | 0.5  | 0.75 |
| ST30  | 512 | 8 | 1 | 0.25 | 1 | 0.5  | 0.0004 | 0.125 | 0.5  | 0.62 |
| ST239 | 512 | 8 | 1 | 0.25 | 1 | 0.5  | 0.0004 | 0.125 | 0.5  | 0.62 |

TABLE 6

Results of docking studies on the interaction of baicalein, berberine analogue, ECG, and kuraridin with SortaseA, expressed as free-binding energies (ΔG).

| Si. No. | Compound | 2D structure | ΔG (kcal/mol) |
|---|---|---|---|
| 1 | Baicalein | 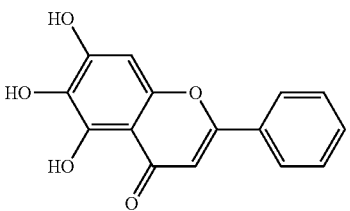 [SMILES: O=c1cc(-c2ccccc2)oc2cc(O)c(O)c(O)c12] | −6.438344 |
| 2 | Berberine analogue | 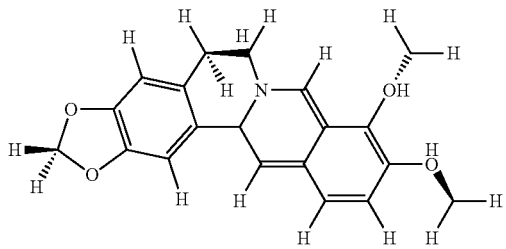 | −7.125368 |

TABLE 6-continued

Results of docking studies on the interaction of baicalein, berberine analogue, ECG, and kuraridin with SortaseA, expressed as free-binding energies (ΔG).

| Sl. No. | Compound | 2D structure | ΔG (kcal/mol) |
|---|---|---|---|
| 3 | Epicatechin gallate | 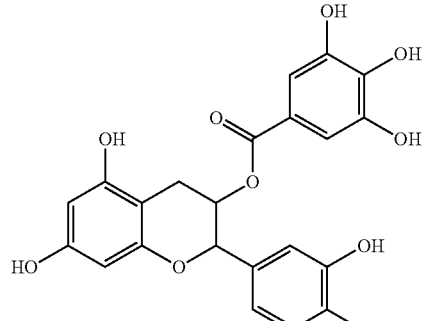 | −8.034483 |
| 4 | Kuraridin | 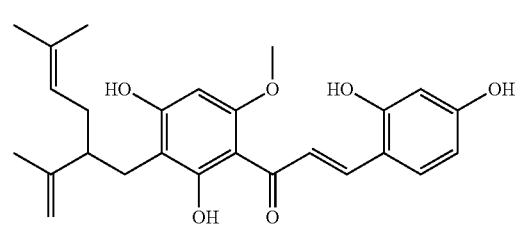 [SMILES: C=C(C)C(CC=C(C)C)Cc1c(O)cc(OC)c(C(=O)/C=C/c2ccc(O)cc2O)c1O] | −8.639615 |

TABLE 7

List of compounds synthesized and tested

| Compound structure | Compound code | Date prepared/ MW (kDal) | Activity (MIC, μg/ml) |
|---|---|---|---|
| 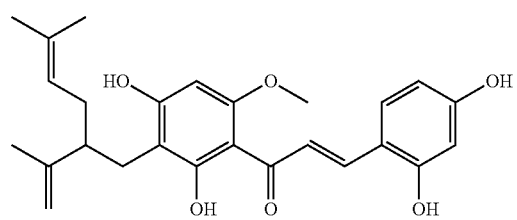 [SMILES: C=C(C)C(CC=C(C)C)Cc1c(O)cc(OC)c(C(=O)/C=C/c2ccc(O)cc2O)c1O] | Kuraridin | Previous/438.52 | 8 μg/mL to RN4220 |
| 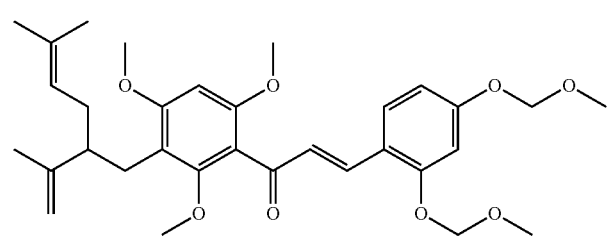 [SMILES: C=C(C)C(CC=C(C)C)Cc1c(OC)cc(OC)c(C(=O)/C=C/c2ccc(OCOC)cc2OCOC)c1OC] | Compound A (also 9A) | May 2018/554.68 | >256 μg/mL to RN4220 |
| 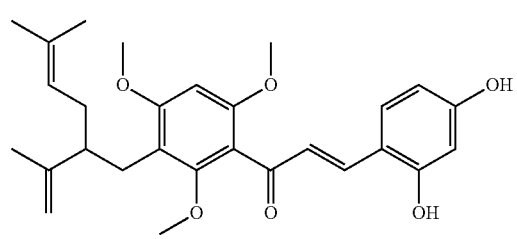 [SMILES: C=C(C)C(CC=C(C)C)Cc1c(OC)cc(OC)c(C(=O)/C=C/c2ccc(O)cc2O)c1OC] | Compound B (also 9B) | May 2018/466.57 | 64 μg/mL to RN4220 |

TABLE 7-continued

List of compounds synthesized and tested

| Compound structure | Compound code | Date prepared/ MW (kDal) | Activity (MIC, µg/ml) |
|---|---|---|---|
| [structure] | WQD-8 | May 2018/646.824 | >256 µg/mL to RN4220/ST30/ST239 |
| [structure] | WQD-101 | Dec 2018/450.575 | >256 µg/ml to RN4220/ST30/ST239 |
| [structure] | WQD-98 | Dec 2018/ 50.575 | >256 µg/ml to RN4220/ST30/ST239 |
| [structure] | WQD-165 | Apr 2019/422.52 | 32 µg/mL (MIC of ST30)<br>4 µg/mL (MIC of ST239) |
| [structure] | WQD-164 (racemic kushenol D) | Apr 2019/452.55 | 128 µg/mL (MIC of ST30)<br>32 µg/mL (MIC of ST239) |
| [structure] | WQD-169 (Kuraridin) | Apr 2019/438.52 | 8 µg/mL (ST30)<br>8 µg/mL (ST239)<br>Kuraridin: |

TABLE 7-continued

List of compounds synthesized and tested

| Compound structure | Compound code | Date prepared/ MW (kDal) | Activity (MIC, μg/ml) |
|---|---|---|---|
| (structure) | WQD-175 | Apr 2019/422.52 | 16 μg/mL (ST30)<br>4 μg/mL (ST239) |

TABLE 8

Minimum in inhibitory concentrations of tested compounds with antibacterial activities Minimum inhibitory concentration to compound (MIC, μg/ml)

| Strain tested | WQD164 | WQD165 | WQD169 (synthesized kuraridin) | WQD175 | Kuraridin (original) |
|---|---|---|---|---|---|
| APH2″-AAC6′ | 16 | 4 | 8 | 4 | 8 |
| APH3′ | 32 | 4 | 8 | 4 | 8 |
| ANT4 | 32 | 8 | 8 | 8 | 8 |
| RN4220 | 64 | 8 | 8 | 8 | 8 |
| 1199B′ | 64 | 8 | 8 | 8 | 8 |
| ST239 | 32 | 4 | 8 | 4 | 8 |
| ST30 | 128 | 32 | 8 | 16 | 8 |

TABLE 9

Combinations of tested compounds with enhanced antibacterial activities

| Compound | Concentration (μg/ml) | | | |
|---|---|---|---|---|
| | MIC alone | MIC combine | FIC | FICI |
| (a) Strain APH2″-AAC6′ | | | | |
| ECG | 512 | 1 | 0.001 | 0.50 |
| WQD-164 | 16 | 8 | 0.50 | |
| ECG | 512 | 0.5 | 0.0009 | 1.00 |
| WQD-165 | 4 | 4 | 1 | |
| ECG | 512 | 4 | 0.007 | 0.25 |
| WQD-169 (Kuraridin) | 8 | 2 | 0.25 | |
| ECG | 512 | 0.5 | 0.0009 | 1.00 |
| WQD-175 | 4 | 4 | 1 | |
| (b) Strain ST239 | | | | |
| ECG | 512 | 2 | 0.001 | 0.50 |
| WQD-164 | 32 | 4 | 0.50 | |
| ECG | 512 | 0.5 | 0.0009 | 1.00 |
| WQD-165 | 4 | 4 | 1 | |
| ECG | 512 | 4 | 0.007 | 0.50 |
| WQD-169 (Kuraridin) | 8 | 4 | 0.5 | |
| ECG | 512 | 0.5 | 0.0009 | 1.00 |
| WQD-175 | 4 | 4 | 1 | |

What is claimed is:

1. A method for suppressing growth of methicillin-resistant *Staphylococcus aureus* (MRSA), comprising contacting the MRSA with kuraridin in a concentration of about 1-4 μg/ml and epicatechin gallate (ECG) in a concentration of about 0.25-8 μg/ml, optionally further with an antibiotic in an effective amount.

2. The method of claim 1, wherein the antibiotic is fusidic acid.

3. The method of claim 1, wherein the antibiotic is gentamicin. antibiotic or a bacteriostatic antibiotic.

4. The method of claim 1, wherein the antibiotic is vancomycin.

5. The method of claim 4, wherein ECG concentration is about 2 μg/ml, the kuraridin concentration is about 2 μg/ml, and the vancomycin concentration is about 0.5 μg/ml.

6. The method of claim 1, wherein the MRSA is within a living organism.

7. The method of claim 6, wherein the living organism is a human.

8. The method of claim 7, comprising administering to the human kuraridin, ECG, and vancomycin, each at a concentration of about 30-120 mg/kg human bodyweight.

9. The method of claim 8, comprising administering to the human kuraridin at about 30 mg/kg, ECG at about 60 mg/kg, and vancomycin at about 120 mg/kg once every 12 hours for at least two days.

10. A composition for suppressing MRSA growth, comprising kuraridin in a concentration of about 1-4 μg/ml and epicatechin gallate (ECG) in a concentration of about 0.25-8 μg/ml, optionally further comprising an antibiotic in an effective amount.

11. The composition of claim 10, wherein the antibiotic is fusidic acid.

12. The composition of claim 10, wherein the antibiotic is gentamicin.

13. The composition of claim 10, wherein the antibiotic is vancomycin.

14. The composition of claim 13, wherein the ECG concentration is about 2 µg/ml, the kuraridin concentration is about 2 µg/ml, and the vancomycin concentration is about 0.5 µg/ml.

15. A kit for suppressing MRSA growth, comprising (1) a first composition comprising epicatechin gallate (ECG) in a concentration of about 0.25-8 µg/ml; and (2) a second composition comprising kuraridin in a concentration of about 1-4 µg/ml.

16. The kit of claim 15, further comprising a third composition comprising an effective amount of an antibiotic.

17. The kit of claim 16, wherein the antibiotic is fusidic acid.

18. The kit of claim 16, wherein the antibiotic is gentamicin.

19. The kit of claim 16, wherein the antibiotic is vancomycin.

20. The kit of claim 15, wherein the first composition is an aqueous solution comprising ECG and vancomycin, and the second composition is an aqueous solution comprising kuraridin and an organic solvent.

* * * * *